US009668690B1

(12) United States Patent
Imran et al.

(10) Patent No.: US 9,668,690 B1
(45) Date of Patent: *Jun. 6, 2017

(54) SUBMUCOSAL GASTRIC IMPLANT DEVICE AND METHOD

(75) Inventors: Mir A. Imran, Menlo Park, CA (US); Olivier K. Colliou, Menlo Park, CA (US); Harm TenHoff, Mountain View, CA (US); Kevin Nason, Menlo Park, CA (US); Ted W. Layman, Park City, UT (US)

(73) Assignee: IntraPace, Inc., San Jose, CA (US)

( * ) Notice: Subject to any disclaimer, the term of this patent is extended or adjusted under 35 U.S.C. 154(b) by 1085 days.

This patent is subject to a terminal disclaimer.

(21) Appl. No.: 10/109,296

(22) Filed: Mar. 26, 2002

Related U.S. Application Data

(63) Continuation-in-part of application No. 09/847,884, filed on May 1, 2001, now Pat. No. 6,535,764.
(Continued)

(51) Int. Cl.
*A61B 5/05* (2006.01)
*A61B 5/00* (2006.01)
(Continued)

(52) U.S. Cl.
CPC .......... *A61B 5/4238* (2013.01); *A61B 5/6882* (2013.01); *A61N 1/0509* (2013.01);
(Continued)

(58) Field of Classification Search
CPC .. A61N 1/36007; A61N 1/05; A61N 1/36071; A61N 1/3605; A61N 1/36
(Continued)

(56) References Cited

U.S. PATENT DOCUMENTS

| 30,366 A | 10/1860 | Rasor et al. ................ 128/419 |
| 3,411,507 A | 11/1968 | Wingrove .................... 128/422 |

(Continued)

FOREIGN PATENT DOCUMENTS

| EP | 0129483 | 12/1984 | ......................... 1/36 |
| EP | 0571938 | 4/1999 | ......................... 1/36 |

(Continued)

OTHER PUBLICATIONS

H. Geldof, et al., Electrogastrogmphic Study of Gastric Myoelectrical Activity in Patients With Unexplained Nausea and Vomiting, *Gut*, 27:799-808, (1986).

(Continued)

*Primary Examiner* — Rex R Holmes
(74) *Attorney, Agent, or Firm* — Kilpatrick Townsend and Stockton LLP

(57) ABSTRACT

A device, system and method for diagnosing and treating gastric disorders is provided. A submucosal gastric implant device is placed within the submucosal layer of a patient's stomach wall. The device in one embodiment provides electrical stimulation of the stomach wall and may use multiple electrode pairs for sequential stimulation. The device may also have other functional aspects such as a sensor for sensing various parameters of the stomach or stomach environment, or a therapeutic delivery device. The implant may be programmed to respond to sensed information or signals. The device may be modular with a portion of the device accessible outside the stomach wall for removal and replacement. An endoscopic delivery system prepares and delivers the functional device through the esophagus and into the stomach where it is placed through an opening in the mucosa into the submucosal layer of the stomach wall. The endoscopic instruments may be used to prepare a cavity in the submucosal layer of the stomach wall and deliver the (Continued)

device to the prepared cavity and if appropriate close the opening in the mucosa.

9 Claims, 41 Drawing Sheets

Related U.S. Application Data

(60) Provisional application No. 60/337,194, filed on Dec. 6, 2001.

(51) Int. Cl.
| | |
|---|---|
| *A61N 1/05* | (2006.01) |
| *A61N 1/36* | (2006.01) |
| *A61B 17/30* | (2006.01) |
| *A61B 17/00* | (2006.01) |
| *A61F 5/00* | (2006.01) |

(52) U.S. Cl.
CPC ....... *A61N 1/0517* (2013.01); *A61N 1/36007* (2013.01); *A61B 2017/00084* (2013.01); *A61B 2017/306* (2013.01); *A61F 5/0003* (2013.01)

(58) Field of Classification Search
USPC .......... 607/40, 133, 41; 606/192; 604/891.1; 600/377
See application file for complete search history.

(56) References Cited

U.S. PATENT DOCUMENTS

| | | | |
|---|---|---|---|
| 3,646,940 A | 3/1972 | Timm et al. .................. 128/421 |
| 3,662,758 A | 5/1972 | Glover .......................... 128/419 |
| 3,677,251 A | 7/1972 | Bowers ......................... 128/419 |
| 3,735,766 A | 5/1973 | Bowers et al. ............... 128/419 |
| 3,796,221 A | 3/1974 | Hagfors ........................ 128/421 |
| 3,815,611 A | 6/1974 | Denniston, III ............. 128/419 |
| 3,835,865 A | 9/1974 | Bowers ......................... 128/419 |
| 4,102,344 A | 7/1978 | Conway ........................ 128/419 |
| RE30,366 E | 8/1980 | Rasor et al. .................. 128/419 |
| 4,628,928 A | 12/1986 | Lowell .......................... 128/303 |
| 4,823,808 A | 4/1989 | Clegg ............................ 128/773 |
| 4,921,481 A | 5/1990 | Danis et al. .................... 604/67 |
| 4,925,446 A | 5/1990 | Garay ............................. 604/96 |
| 5,188,104 A | 2/1993 | Wernicke et al. ........... 128/419 |
| 5,193,540 A * | 3/1993 | Schulman et al. ............ 607/61 |
| 5,197,491 A | 3/1993 | Anderson et al. ........... 128/786 |
| 5,217,449 A | 6/1993 | Yuda et al. ................... 604/890 |
| 5,292,344 A | 3/1994 | Douglas ......................... 607/40 |
| 5,415,181 A | 5/1995 | Hogrefe et al. ............. 128/734 |
| 5,423,872 A | 6/1995 | Cigaina .......................... 607/40 |
| 5,540,730 A | 7/1996 | Terry et al. .................... 607/40 |
| 5,558,640 A | 9/1996 | Pfeiler et al. .................. 604/67 |
| 5,690,691 A | 11/1997 | Chen et al. ..................... 607/40 |
| 5,716,392 A | 2/1998 | Bourgeois et al. .......... 607/132 |
| 5,792,048 A | 8/1998 | Schaefer ...................... 600/302 |
| 5,800,445 A | 9/1998 | Ratcliff ........................ 606/116 |
| 5,836,994 A | 11/1998 | Bourgeois ...................... 607/40 |
| 5,861,014 A | 1/1999 | Familoni ........................ 607/40 |
| 5,928,195 A | 7/1999 | Malamud et al. ............ 604/141 |
| 5,993,473 A | 11/1999 | Chan et al. ................... 606/192 |
| 5,995,872 A | 11/1999 | Bourgeois ...................... 607/40 |
| 6,026,326 A | 2/2000 | Bardy ............................. 607/40 |
| 6,041,258 A | 3/2000 | Cigaina et al. ................ 607/40 |
| 6,083,249 A | 7/2000 | Familoni ........................ 607/40 |
| 6,091,992 A | 7/2000 | Bourgeois ...................... 607/40 |
| 6,097,984 A | 8/2000 | Douglas ......................... 607/40 |
| 6,098,629 A | 8/2000 | Johnson et al. .............. 128/897 |
| 6,104,955 A | 8/2000 | Bourgeois ...................... 607/40 |
| 6,115,635 A | 9/2000 | Bourgeois ...................... 607/40 |
| 6,205,359 B1 | 3/2001 | Boveja ............................ 607/45 |
| 6,214,032 B1 * | 4/2001 | Loeb et al. ...................... 607/1 |
| 6,216,039 B1 | 4/2001 | Bourgeois ...................... 607/40 |
| 6,243,607 B1 * | 6/2001 | Mintchev et al. ............. 607/40 |
| 6,285,897 B1 | 9/2001 | Kilcoyne et al. |
| 6,321,124 B1 | 11/2001 | Cigaina .......................... 607/133 |
| 6,327,503 B1 | 12/2001 | Familoni ........................ 607/40 |
| 6,366,814 B1 | 4/2002 | Boveja et al. .................. 607/45 |
| 6,381,495 B1 | 4/2002 | Jenkins .......................... 607/40 |
| 6,427,089 B1 | 7/2002 | Knowlton |
| 6,449,511 B1 | 9/2002 | Mintchev et al. ............. 607/40 |
| 6,453,199 B1 | 9/2002 | Kobozev ........................ 607/40 |
| 6,454,785 B2 * | 9/2002 | De Hoyos Garza .......... 606/192 |
| 6,477,423 B1 | 11/2002 | Jenkins .......................... 607/40 |
| 6,510,332 B1 | 1/2003 | Greenstein .................... 600/377 |
| 6,529,778 B2 | 3/2003 | Prutchi ......................... 607/119 |
| 6,535,764 B2 * | 3/2003 | Imran et al. .................... 607/40 |
| 6,540,789 B1 | 4/2003 | Silverman et al. ........ 623/23.65 |
| 6,542,776 B1 | 4/2003 | Gordon et al. ................. 607/40 |
| 6,564,101 B1 | 5/2003 | Zikria ............................. 607/40 |
| 6,571,127 B1 | 5/2003 | Ben-Haim et al. ............ 607/40 |
| 6,591,137 B1 * | 7/2003 | Fischell et al. ................ 607/40 |
| 6,600,953 B2 | 7/2003 | Flesler et al. .................. 607/40 |
| 6,606,518 B1 | 8/2003 | Cigaina .......................... 607/41 |
| 6,606,523 B1 | 8/2003 | Jenkins ......................... 607/133 |
| 6,609,025 B2 | 8/2003 | Barrett et al. .................. 607/2 |
| 6,611,715 B1 | 8/2003 | Boveja ............................ 607/40 |
| 6,615,084 B1 | 9/2003 | Cigaina .......................... 607/40 |
| 6,684,104 B2 | 1/2004 | Gordon et al. ................. 607/40 |
| 6,826,428 B1 | 11/2004 | Chen et al. ..................... 607/40 |
| 6,879,859 B1 | 4/2005 | Boveja ............................ 607/45 |
| 6,895,278 B1 | 5/2005 | Gordon .......................... 607/40 |
| 6,895,279 B2 | 5/2005 | Loeb et al. ..................... 607/40 |
| 6,941,171 B2 * | 9/2005 | Mann et al. .................... 607/39 |
| 7,054,692 B1 | 5/2006 | Whitehurst et al. |
| 7,096,070 B1 * | 8/2006 | Jenkins et al. ............... 607/116 |
| 7,558,629 B2 | 7/2009 | Keimel et al. |
| 2002/0072780 A1 | 6/2002 | Foley .............................. 607/40 |
| 2002/0103424 A1 | 8/2002 | Swoyer et al. ............... 600/350 |
| 2002/0103521 A1 | 8/2002 | Swoyer et al. ............... 607/116 |
| 2002/0103522 A1 | 8/2002 | Swoyer et al. ............... 607/116 |
| 2002/0161414 A1 * | 10/2002 | Flesler et al. .................. 607/40 |
| 2002/0198570 A1 | 12/2002 | Puskas ............................ 607/40 |
| 2002/0198571 A1 | 12/2002 | Puskas ............................ 604/2 |
| 2003/0055463 A1 | 3/2003 | Gordon et al. ................. 607/40 |
| 2003/0120328 A1 | 6/2003 | Jenkins ........................... 607/2 |
| 2003/0144708 A1 | 7/2003 | Starkebaum ................. 607/116 |
| 2003/0212439 A1 | 11/2003 | Schuler et al. ................. 607/40 |
| 2004/0059393 A1 | 3/2004 | Policker et al. ............... 607/40 |
| 2004/0133089 A1 | 7/2004 | Kilcoyne et al. ............. 600/350 |
| 2004/0147816 A1 | 7/2004 | Policker et al. ............. 600/300 |
| 2004/0162595 A1 | 8/2004 | Foley .............................. 607/40 |
| 2004/0172095 A1 | 9/2004 | Jenkins ......................... 607/116 |
| 2005/0021101 A1 | 1/2005 | Chen et al. ..................... 607/40 |
| 2005/0113880 A1 | 5/2005 | Gordon et al. ............... 436/106 |
| 2006/0116736 A1 | 6/2006 | DiLorenzo |

FOREIGN PATENT DOCUMENTS

| | | | |
|---|---|---|---|
| WO | WO 98/43700 A1 | 10/1998 | |
| WO | 9853878 | 12/1998 | ............................ 1/5 |
| WO | WO 00/30534 A1 | 6/2000 | |
| WO | 0158389 | 8/2001 | ............................ 2/48 |
| WO | 0176690 | 10/2001 | ............................ 1/18 |
| WO | WO 02/26101 | 4/2002 | |

OTHER PUBLICATIONS

Bader-Eddine Bellabsene, et al., Evaluation of a Portable Gastric Stimulator, Ninth Annual Conference of the Engineering in Medicine and Biology Society, (1987).
S. K. Santa, et al., Electrical Stimulation of Gastric Electrical Control Activity, *Am. J. of Physiology*, 225/1:125-131, (Jul. 1973).
Valerio Cigaina, Gastric Myo-Electrical Pacing a Therapy for Morbid Obesity: Preliminary Results.
Eagon, et al., Gastrointestinal Pacing, *Gastrointestinal Tract*, 73/6:1161-1172 (Dec. 1993).
Kelly, et al., Pacing the Canine Stomach With Electric Stimulation, *Am. J. of Physiology*, 222/3:588-594, (Mar. 1972).
Swain, et al., An Endoscopically Deliverable Tissue-Transfixing Device for Securing Biosensors in the Gastrointestinal Tract, *Gastrointestinal Endoscopy*, 40/6:730-734, (1994).

(56) References Cited

OTHER PUBLICATIONS

C. Paul Swain, et al., An Endoscopically Deliverable Tissue-Transfixing Device for Securing Biosensors In the Gastrointestinal Tract, *Gastrointestinal Endoscopy*, 40/6:730-734 (1994).

Keith E. Kelly, et al., Pacing the Canine Stomach With Electric Stimulation, *Am. J. of Physiology*, 222/3:588-594 (Mar. 1972).

J. Chris Eagon et al., Gastrointestinal Pacing, *Surgical Clinics of North America*, 73/6:1161-1172 (Dec. 1993).

Valerio Cigaina, et al., Gastric Myo-Electrical Pacing as Therapy for Morbid Obesity: Preliminary Results.

H. Geldof, et al., Electrogastrographic Study of Gastric Myoelectrical Activity In Patients With Unexplained Nausea and Vomiting, *Gut*, 27:799-808, (1986).

Brent W. Miedema, et al., Pacing the Human Stomach, *Surgery*, 143-150, (Feb. 1992).

Keith A. Kelly, Differential Responses of the Canine Gastric Corpus and Antrum to Electric Stimulation, *Am. J. of Physiology*, 226/1:230-234, (Jan. 1974).

Electric Stimulation of the Gastrointestinal Tract, GP, p. 151 (Apr. 1964).

Michael P. Hocking, Postoperative Gastroparesis and Tachygastria-Response to Electric Stimulation and Erythromycin, *Surgery*, 114/3:538-542 (Sep. 1993).

Keith A. Kelly et al., Role of the Gastric Pacesetter Potential Defined by Electrical Pacing, *Canadian J. of Physiology and Pharmacology*, 50:1017-1019, (1972).

Babajide O. Familoni, Efficacy of Electrical Stimulation at Frequencies Higher Than Basal Rate in Canine Stomach, *Digestive Diseases and Sciences*, 42/5:892-897, (May 1997).

Bader-Eddine Bellahsene, et al., Evaluation of a Portable Gastric Stimulator, Ninth Annual Conference of the Engineering in Medicine and Biology Society, (1987).

J. Chris Eagon, et al., Effects of Gastric Pacing on Canine Gastric Motility and Emptying, *The American Physiological Society*, 265/4:G767-G774, (Oct. 1993).

Babajide O. Familoni, et al., Electrical Pacing of the Stomach in Dogs.

S. K. Sarna, et al., Electrical Stimulation of Gastric Electrical Control Activity, *Am. J. of Physiology*, 225/1:125-131, (Jul. 1973).

S. K. Sarna, et al., Gastric Pacemakers, *Gastroenterology*, 70:226-231, (1976).

Edwin E. Daniel, et al., Electrical Activity of the Gastrointestinal Tract as an Indication of Mechanical Activity, *Am. J. of Digestive Diseases*, 8/1:54-102, (1963).

M. Kubota, ert al., Manometric Evaluation of Children With Chronic Constipation Using a Suction-Stimulation Electrode, *Eu. J. Pediari.Surg.*, 2:287-290, (1992).

\* cited by examiner

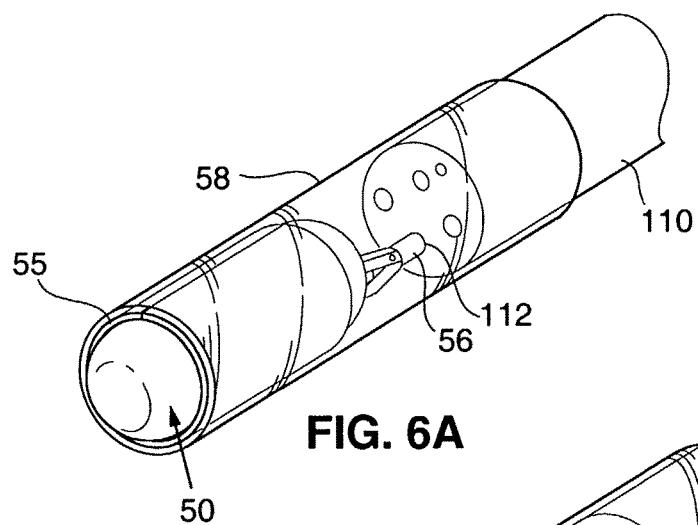
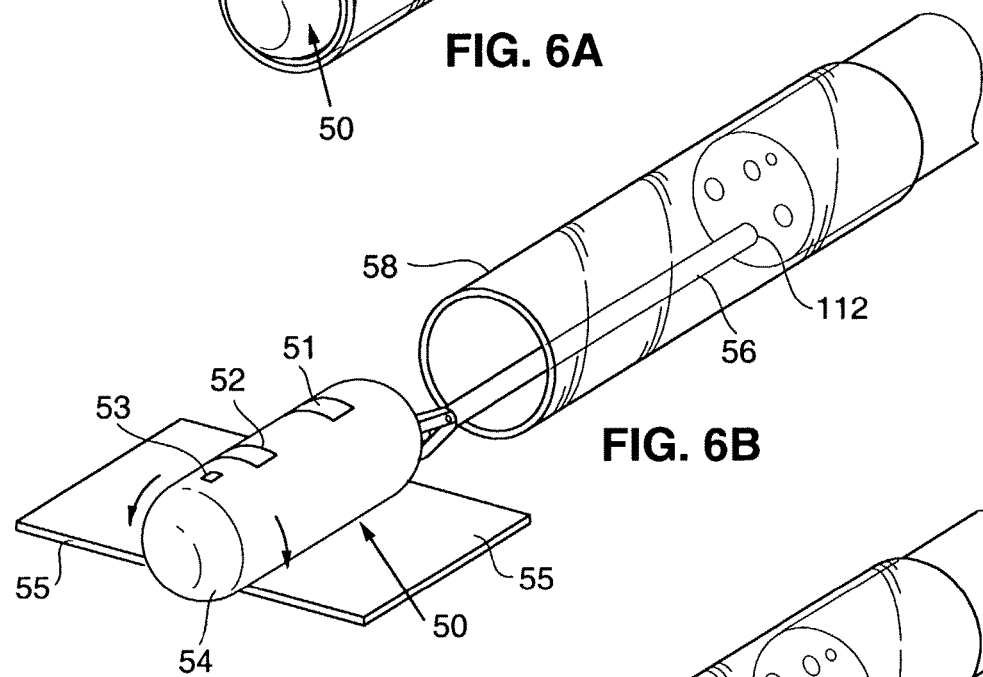
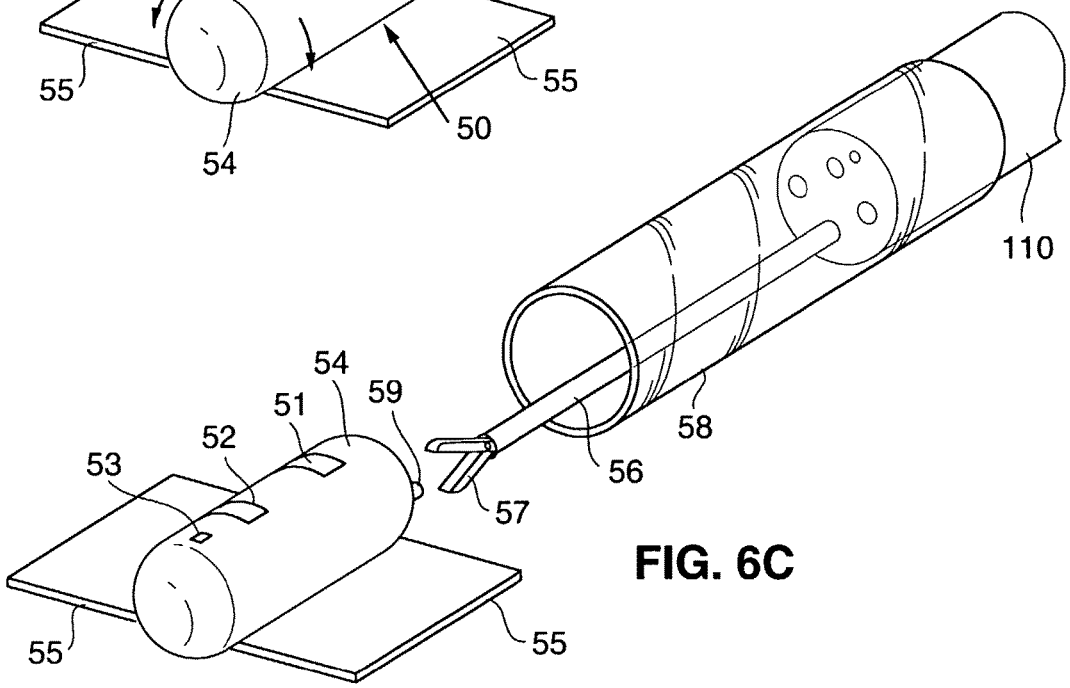

SUBMUCOSAL GASTRIC IMPLANT DEVICE AND METHOD

FIELD OF THE INVENTION

This invention relates to an implantable device, a system and a method for electrically stimulating the stomach wall to effect gastric motility or otherwise treat gastrointestinal related disorders. One aspect in particular relates to a device and method for implanting a gastric stimulator in the submucosal layer of the stomach wall. This invention also relates to treating or diagnosing stomach conditions or disorders by implanting a functional device in a submucosal layer of the stomach wall.

BACKGROUND OF THE INVENTION

Various organs of the gastrointestinal tract such as the stomach, small intestine and colon contain cells that are believed to govern the organs' periodic contractile behavior. In healthy humans, in certain regions of the organs, these cells generate and propagate rhythmic electrical signals. In general, several types of electrical potential activities have been observed in the gastrointestinal tract. Consistent slow wave or pacesetter potentials have been observed and higher frequency spike activity has been observed. The pacesetter potentials are continuously propagating, relatively low frequency, cyclic depolarizations of the smooth muscle cell lining. The higher frequency spike bursts generally correspond with smooth muscle contractile activity and peristalsis. In general, when the spike burst activity occurs, it appears to be at a fixed time delay with respect to the slow wave potentials. It is believed that when the pacesetter potentials are combined with a chemical or neural excitation of the cells, smooth muscle contractile activity occurs. Also it is believed that the pacesetter potentials control and coordinate the frequency and direction of the contractions.

Electrical stimulation of the gastrointestinal tract has been proposed to treat motility related disorders and other gastrointestinal diseases or conditions. The electrical stimulation has been proposed in a number of forms, such as, e.g., pacing, electrical contractile stimulation or other stimulation, e.g., to treat nausea or obesity. Electrical pacing of the gastrointestinal tract is generally defined as a periodic electrical stimulation that captures and/or controls the frequency of the pacesetter potential or slow wave activity of the gastrointestinal organ (including in a retrograde direction). Electrical contractile stimulation generally refers to stimulation that directly causes or results in muscular contraction associated with the gastrointestinal tract. In some disease states, dysrhythmias of the gastric pacesetter potentials may be present. The result of the abnormal pacesetter potentials may be gastric retention of food. Electrical stimulation of gastric tissue has been proposed to induce peristalsis. Electrical stimulation has also been proposed to treat obesity by altering gastric motility, or by stimulating neural pathways. For example, one treatment method causes the stomach to retain food for a greater duration. Electrical stimulation has also been proposed to slow the gastric emptying to treat a disorder known as dumping syndrome where the stomach empties at an abnormally high rate into the small intestine causing various gastrointestinal disorders. In particular, electrical pacing of gastric pacesetter potentials has been proposed to induce regular rhythms for the pacesetter potentials with the intent of inducing regular or controlled gastric contractions.

Within the stomach, at least one pacemaker region has been identified near the interface of the fundus and the corpus along the greater curvature. This region has been one target for gastric pacing. Peristalsis controlled by this region is believed to serve to mix and break down food and propel small particles through the pylorus into the duodenum. It is believed that gastric emptying of liquids is controlled by the fundus. This region is believed to create with characteristic contractions, a pressure gradient between the fundus, pylorus and duodenum that relates to the rate of gastric emptying.

An early attempt at a gastric stimulation device included an electrode at the end of a nasogastric tube or catheter. The nasogastric tube was passed into the stomach transnasally. Electrical stimulation was applied through the electrode on the end of the tube using an external stimulator unit. The return electrode was placed on the abdomen. This device required a transnasal procedure whenever stimulation was required.

Other devices used to pace the stomach have generally been implanted by accessing the outside of the stomach through an opening in the abdomen, either through open surgery or laparoscopic surgery. Electrodes have been attached to the stomach wall with attached leads extending through the abdomen.

These procedures involve implanting a pacemaker device in a subcutaneous or sub-muscular pocket. The devices are anchored into the subcutaneous or sub-muscular pocket initially by a suture anchor and eventually by fibrous tissue ingrowth around the unit. The pacemaker device housing is typically constructed of a titanium or stainless steel material with connectors molded into an epoxy header. The devices are thin in one dimension so that they are less visible when implanted directly under the skin or muscle layer. Therefore, in order to accommodate the necessary battery capacity, the devices are widely shaped, e.g. round or kidney shaped in the other two dimensions. The leads extend from the unit's epoxy header to a stimulation site remote from the pacemaker unit.

A gastrointestinal pacemaker having phased multi-point stimulation has been proposed with electrodes placed in multiple points around the GI tract including on the inner or outer surface of the stomach. As described, the device could be preprogrammed or include an implantable pacemaker detachably coupled to the multiple electrodes in their various locations, and including an electronic controller that may be programmed by using an external programmer to set stimulation parameters. The implantable pacemaker is located remote from the stimulation sites.

Some gastric stimulation procedures have proposed electrical stimulation in response to sensing electrical pulses within the stomach within a particular range. Additionally, a device has been proposed to sense electrical parameters to determine the fullness of an organ and the absence of muscular contraction, and to deliver electrical muscular contraction stimulation to the organ in response. In general, the currently proposed gastric electrical stimulation procedures are relatively invasive and require accessing the stomach through the abdomen, e.g., in an open or a laparoscopic procedure. The units have relatively wide dimensions in one plane. Accordingly, it would be desirable to provide a less invasive procedure and device for electrically stimulating the stomach. It would also be desirable to provide a device in which various components are accessible for removal or replacement, particularly in a less invasive procedure.

A machine that places a nylon tag has been proposed for attaching a "payload" to the inner wall of a stomach. The machine places the tag through the stomach wall and back into the stomach in a manner that causes folding of the stomach wall and may cause tissue damage when the smooth muscle of the stomach wall contracts.

It would therefore be desirable to provide a means and method for implanting, a functional device having therapeutic or diagnostic functions, within the stomach wall, so that the stomach wall is protected from damage from mechanical stresses and forces due to the attachment of the stimulator device. It would further be desirable to employ such a device and method that at the same time protect the functional device from the stomach's corrosive environment, or churning or grinding forces, and peristaltic movement, typical when food is digested and passed out of the stomach into the intestinal tract.

SUMMARY OF THE INVENTION

The present invention provides a device, system and method for diagnosing and treating gastric conditions or disorders. According to one embodiment of the invention, a functional device is implanted in the submucosal layer of the stomach wall. The functional device may have one or more therapeutic or diagnostic functions. For example, therapeutic functions may include delivering medication or gene therapy treatment, electrical stimulation of a muscle layer of the stomach wall or associated nerves of the stomach; and diagnostic functions may include sensing electrical parameters, pressure, movement, temperature, utilizing diagnostic ultrasound with an acoustic transducer, or measuring other parameters to determine conditions of the stomach or effectiveness of treatment such as electrical stimulation.

An externally transmitted telemetric signal may be used to actuate treatment. For example, the release of the medication or other substance may be actuated by an external RF signal received by electronics in the device housing. Sensed diagnostic information may also be transmitted from the implanted device to an external receiver/controller that may record or evaluate the sensed information.

The present invention further provides a method of implanting such a device in the stomach wall. According to one embodiment, at least a portion of the functional device is implanted into the submucosal layer of the stomach wall. The stomach wall may be accessed in an endoscopic, laparoscopic or open surgical procedure wherein an opening is made in the stomach wall and the implant is placed through the opening into the submucosal layer. In one variation, a pocket is formed in the stomach wall and the submucosal layer is dissected. The implant is then placed within the submucosal layer. In one embodiment, endoscopic instruments are used to access the stomach wall through the patient's esophagus.

The present invention further provides a device, system and method for gastric electrical stimulation. Electrical stimulation is generally defined herein to mean any application of an electrical signal or of an electromagnetic field to tissue of the stomach for a therapeutic or diagnostic purpose. In one embodiment, an electrical stimulation signal entrains a slow wave signal of the stomach smooth muscle that is clinically absent, weak or of an undesirable frequency or repetition rate, is sporadic or otherwise not optimal. Also the stimulator may be designed to trigger the spike burst electrical activity of the smooth muscle associated with smooth muscle contractions. The signals may also be designed to inhibit smooth muscle pacing potentials to reduce smooth muscle contractions. The signals may also be designed to disrupt the natural waveform and effectively alter the existing or inherent pacing. The stimulator may also be designed to affect nerves associated with the stomach. In one variation, the device is designed to facilitate or expedite mixing or breaking down of food matter or liquids in the stomach. In another variation, the device is designed to control, facilitate or expedite movement of food matter or liquids through the stomach and into the small intestine. In another variation, the device is designed to stimulate the stomach to delay passage of food from the stomach and into the small intestine. Other stimulation effects are also contemplated, including but not limited to using stimulation to treat nausea, obesity or pain symptoms. The stimulation may affect the smooth muscle contractions and/or nerves associated with the stomach.

The stimulation electrodes provide stimulation either by way of a preprogrammed pulse generator or one that is programmed or revised when the device is implanted in the stomach, e.g. based on sensed parameters or response to stimulation and/or to optimize various parameters, e.g., impedance, current density, etc. The stimulator is preferably provided with RF or other signal transmission and reception capabilities. The signal transmission capabilities may be used for telemetric communication between the stimulator and an external device, e.g. to communicate data to the external device or to receive additional programming information, command signals or stimulation signals from the external device. The stimulator may also combine the electrical stimulation feature with other therapeutic or diagnostic functions such as, e.g., drug delivery.

The stimulating device of the present invention resides within the submucosal layer, between the muscle layer (comprising several muscle layers, i.e., the oblique, circular and longitudinal layers) and mucosal layer of a patient's stomach wall. One embodiment of the device includes: an electronics unit containing the electronic circuitry of the device with at least one stimulating electrode that when implanted is in electrical contact with a muscle layer of the stomach wall. One or more stimulating electrodes may be located on the electronics unit housing or may be otherwise coupled to the housing and located within the submucosal layer. The housing may be implanted in the submucosa and electrodes coupled to the housing may be deployed from within the submucosa into contact with the muscle layer. Alternatively a housing may be removably attached to the stomach wall and removably connected to an electrode portion implanted in the stomach wall. The housing thus may be exchanged while the electrode portion remains implanted in the stomach wall, e.g. when the batteries need replacement. The stimulation is provided through at least one stimulating electrode and preferably through at least one pair of bipolar electrodes. Alternatively a remote return electrode may be provided in a monopolar device. The stimulator device may be powered by a battery included with the device or may be inductively powered, e.g. by an external source.

Various means for maintaining the electrodes in position, i.e., with respect to the muscle layer may be provided as well. Such other means may include for example, anchors, sutures, anti-rotation mechanisms and device shape design.

The stimulation device is constructed of a size and shape such that it can be deployed through the mouth and esophagus with the aid of an endoscope. As such, the stimulator is of a generally small profile when delivered to the implant site. It is preferred that the implant be constructed and/or implanted so that the electrode predictably maintains electrical contact with a muscle layer of the stomach wall. Accordingly, the device may be constructed of a configuration or shape that prevents device rotation, or may be constructed so that device rotation or movement does not interfere with the electrode/muscle layer contact.

One aspect of the invention may include a means for maintaining the device in proper orientation so that the electrodes, sensors or other transducers on the device maintain contact with a preferred area or layer of the stomach wall, i.e., so that the electrodes, sensors or other transducers are preferentially facing a desired wall within a submucosal space, e.g. a muscle layer. An anti-rotation means may be provided that prevents rotation of the implant around axes that would move electrodes, sensors or transducers away from intimate contact with a desired area of the stomach wall, such as, e.g., a muscle layer or mucosal layer.

The shape of the implant, may, for example, have a broad aspect when viewing that side of the device intended to be in contact with a particular layer of the stomach wall (e.g., a muscle layer or mucosal layer); i.e., the top-view of the device has relatively large length and width dimensions with respect to the height dimension of the device given by its side-views.

In one embodiment, the aspect ratio of the device, defined as the width of a side-view divided by the height of the device is larger than about 1, preferably larger than about 1.4 and more preferably larger than about 1.8.

In an alternative embodiment, an anti-rotation means may be provided that prevents rotation of the implant about an axis parallel to an intended tissue plane of contact. A device in one variation is dimensioned so that the aspect ratio of the device viewed along an axis parallel to the intended plane of contact is greater than one and preferably greater than 1.4 and more preferably greater than 1.8. The aspect ratio as used herein is the width to height ratio of the aspect viewed along a particular axis. In another variation, the anti-rotation device comprises and extendible or expandable portion or member that extends into a position that prevents rotation of the electrodes away from contact with the muscle layer.

In another embodiment, an anti-rotation means may be provided that prevents rotation of the implant about an axis parallel to a common plane on which the pair of surface stimulating electrodes lie. Accordingly, a device in such embodiment is dimensioned so that the aspect ratio of the device viewed along an axis parallel to plane on which a pair of surface stimulating electrodes lie is greater than one and preferably greater than 1.4 and more preferably greater than 1.8. The width in this particular embodiment may be defined by a plane on which a pair of surface stimulating electrodes lies.

The implant may have a relatively small profile when implanted and may be altered to have a different shape when implanted, to prevent rotation and/or provide optimal sensor/transducer/electrode contact with the stomach wall layer, e.g., a mucosal or muscle layer.

The surface of the implant may be designed to promote encapsulation or tissue ingrowth, e.g. by choice of material, coatings or surface texture. It may be desirable to provide tissue ingrowth at or near the electrodes to ensure good contact between the electrodes and the tissue to be stimulated. Such encapsulation or tissue ingrowth may help prevent movement of the implant and in particular, a rotational movement in which the contact between the electrodes and stomach muscle layer may be lost. Thus the electrodes or surrounding area may be coated with a material such as P-15, which is a commercially available compound that promotes cellular adhesion and tissue ingrowth.

The device or portions of the device may be constructed of or coated with substances that promote or inhibit tissue ingrowth. For example, it may be desirable to inhibit tissue ingrowth in general so that the device may be easily explanted. Thus, the implant may be coated with or constructed of a material that inhibits such tissue ingrowth.

The device components are constructed of biocompatible materials that allow it to remain in the environment of the stomach within the stomach wall for the life of the device, e.g., several weeks, months or more. The housing of the electronics unit or shell may be constructed with medical grade titanium, tantalum or alloys of these metals. Alternatively, the housing may also be constructed out of suitable inert polymers, for example, from the polyolefin family, e.g., HDPE (high density polyethylene), PP (polypropylene), UHMWPE (ultra high molecular weight polyethylene), or fluoropolymer such as PTFE (polytetrafluoroethylene) FEP (fluorinated ethylene propylene) and other members. PMP (polymethylpentene), polysulfone, PMMA (polymethylmethacrylate) may also be used. Softer materials may be used, such as, e.g., silicones, C-Flex™, polyurethanes, co-polymer nylons (e.g. PEBAX).

The electrodes are preferably made of corrosion resistant metals and alloys such as, e.g. platinum, iridium, gold, tantalum, titanium, stainless steel or alloys of one or more of these metals, e.g., a platinum/iridium alloy.

The electrodes may be mounted directly on the housing or placed on a flexible tail or tether. Electrodes are preferably coupled to the electronic circuitry through sealed electrical contacts or through leads extending into the housing through molded corrosion resistant materials such as those described above.

A preferred system of the present invention includes an endoscopic delivery system for delivering the stimulator through the esophagus and into the stomach where it is implanted in the stomach wall. The electronics unit is deployed by first identifying a site for implantation, then preparing an opening in the mucosa to access the submucosal layer for implanting the device, then placing the device through the opening into the submucosal layer and then if desired or necessary, closing the cavity. According to one variation, after preparing the opening in the mucosal layer, a pocket or cavity is prepared in the submucosal layer to receive the device.

An endoscope and associated instruments are used to prepare the selected site in the stomach wall, for implanting a stimulator. A knife, needle or cutting instrument may be used to prepare an opening in the mucosa to access the submucosal layer. According to one embodiment, a material or solution is injected into the site for implanting the device, to form a bleb or blister in the submucosal layer. The material or solution may also break down some of the submucosal tissue to form a pocket. Alternatively or additionally, a tissue dissector may be used to prepare a cavity. The tissue dissector may be a blunt dissector, for example, a blunt tool, an expandable compliant or non-compliant balloon, or another mechanically expanding device, or a cutting blade. The dissector may also be a device using an energy source to break down or cut tissue such as an electrosurgical cutting or coagulating device, or an ultrasonic or laser device.

The system further includes an endoscopic instrument or instruments for delivering the stimulator to the prepared cavity and, if desired or necessary, for closing the cavity. The instruments for delivering the stimulator may include means for determining the rotational orientation of the implant so that the electrodes can be placed in a position interfacing and in contact with a muscle layer of the stomach wall. Stabilizing instruments may be provided to stabilize the endoscope and associated instruments and/or to stabilize or grasp the stomach wall or tissue during preparation of the cavity for implantation of the stimulator. A further aspect of the invention provides instruments and mechanisms for closing the opening in the mucosal layer of the stomach wall after implanting the stimulator in the submucosa.

One embodiment of the system includes a flexible endoscope or endoscopic instrument, for locating a preferred site in the stomach for device attachment. In one embodiment, the endoscope or endoscopic instrument comprises electrodes that may be placed on the inside of the stomach wall to measure electrical activity or impedance, or to deliver test stimulation pulses to identify optimal stimulation parameters or locations In addition to the device being capable of stimulating the stomach wall, the electrodes of the device may also be used for diagnostic purposes. For example, the electrodes may be used to sense and observe electrical activity in the stomach wall. Such sensing may be used over time to identify patterns, diagnose diseases and evaluate effectiveness of various treatment protocols. For example irregular or lack of EMG or EGG (electrogastrogram) activity may be sensed. Stimulation may be provided in response to sensed EMG or EGG activity or lack of activity.

In one variation, sensors can be included in the device or separately for sensing various parameters of the stomach. The sensors may be mounted on the stimulator housing, or by other means, for example, in an independently attached device for example attached with an anchor or within the submucosa. The stimulation device may include a mechanical sensor that senses, for example, stomach wall contractions. In one embodiment a device implanted in the stomach wall includes a pressure sensor that is arranged to measure pressure change due to contractions of surrounding tissue. Alternatively, electrical sensors may detect changes in impedance due to changes in wall thickness from smooth muscle contractions. Other examples of such sensors may include, for example, pH sensors, impedance sensors, pressure sensors, strain gauges, and temperature measuring devices such as a thermocouple.

The stimulation device may be programmed to deliver stimulation in response to sensing electrical parameters or other sensed parameters. The device may also be user controlled, where the recipient of the device or treating practitioner is able to externally activate the device, for example by using an external unit which delivers a control signal via telemetry. A temperature sensor may be used, for example, to determine when food has been ingested, by a change in temperature. The device may begin stimulating the stomach upon detecting sudden change in temperature. Pressure sensors may be used to sense motility patterns, e.g. presence, strength or frequency of contractions. Mean pressure shifts may be observed to identify fundal contractility. The stimulation device may also use sensed parameters to program or reprogram the device stimulation program. For example, by measuring impedance changes through a circuit coupled to the electrodes (e.g., delivering a constant current or voltage across the electrodes to determine impedance) or determining the contractile behavior of the stomach using a strain gauge, in response to stimulation pulses, the effectiveness of the stimulation pulses may be monitored and adjusted to provide optimal response. The stimulation program may also include an automatic adjustment in response to changes in pressure measurement.

An alternative feature of the invention may provide multiple pairs of stimulation electrodes at different points on the stomach wall. The electrode pairs may be on a single device such that they are in communication with each other by way of electrical connectors such as wires, etc. The multiple electrode pairs may be on individual devices separately implanted, whereby a first device, i.e., a master, delivers a first set of stimulation pulses. Slave devices, sensing the first stimulation pulses, follow with additional stimulation pulses at the different points in the stomach. The slave devices may respond after sensing a first stimulation pulse or in response to a sensed parameter indicating that the first stimulation pulses have been effectively delivered (e.g., changes in pressure, contractions of the stomach, or propagated depolarization signals etc.) The slave devices may be programmed to provide stimulation or alter their stimulation protocols based on the presence, absence or a measured parameter of the first stimulation pulse sensed by the slave device. The slave device may also be programmed to provide stimulation or alter their stimulation protocols based on the sensed degree of response from the first stimulation pulses by the master device, for example, by sensing the degree of muscle contraction or a resulting depolarization induced by the pacing pulse or a resulting inherent pulse generated by the stomach wall. (as opposed to the original stimulation signal). The implanted devices may be capable of being either a master or slave device. The implant's function may be selected after the device has been implanted, to provide a number of possible configurations.

Embodiments of various aspects of the invention are described in the following detailed description.

DETAILED DESCRIPTION OF THE DRAWINGS

FIG. 6A illustrates a fifth embodiment of a functional device in a first position within a sleeve and coupled to an endoscope for delivery.

FIG. 6B illustrates the functional device and endoscope of FIG. 6A after the functional device has been deployed within a submucosal pocket.

FIG. 6C illustrates the functional device and endoscope of FIG. 6B after the functional device has been deployed within a submucosal pocket and is disengaged from the endoscope.

FIGS. 33A-E illustrate side partial cross sectional views of a wound closure device in use in a method for closing the opening formed in the stomach wall.

Figure 34A:
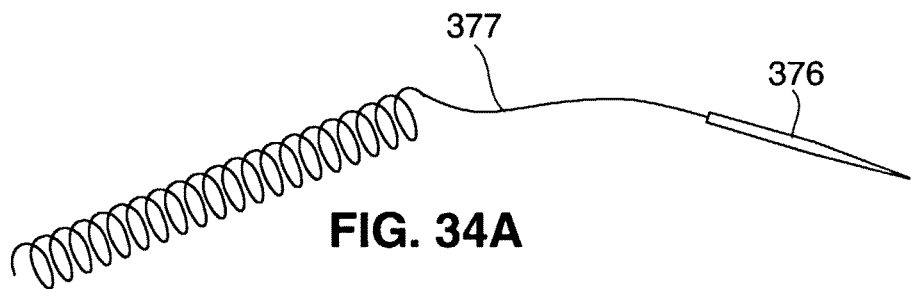
Figure 34B:
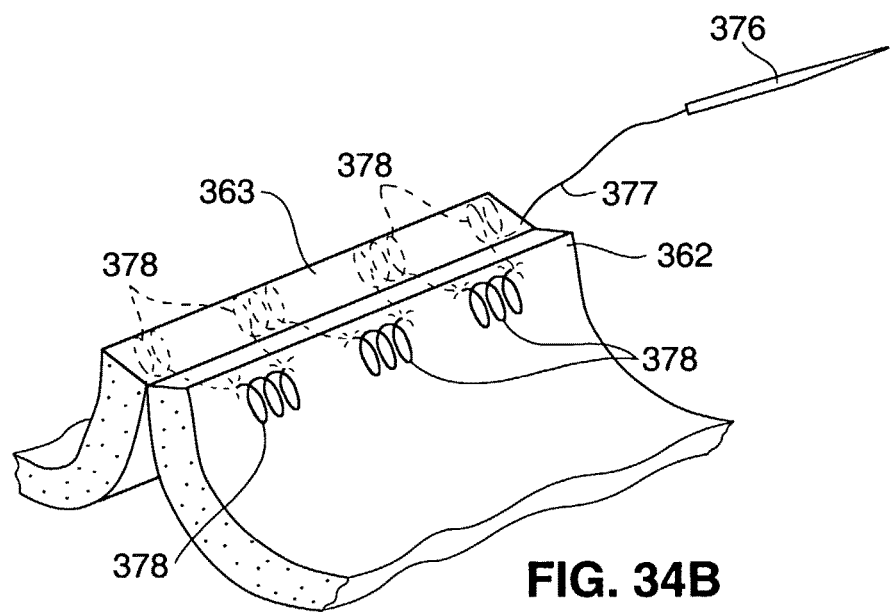
Figure 34C:
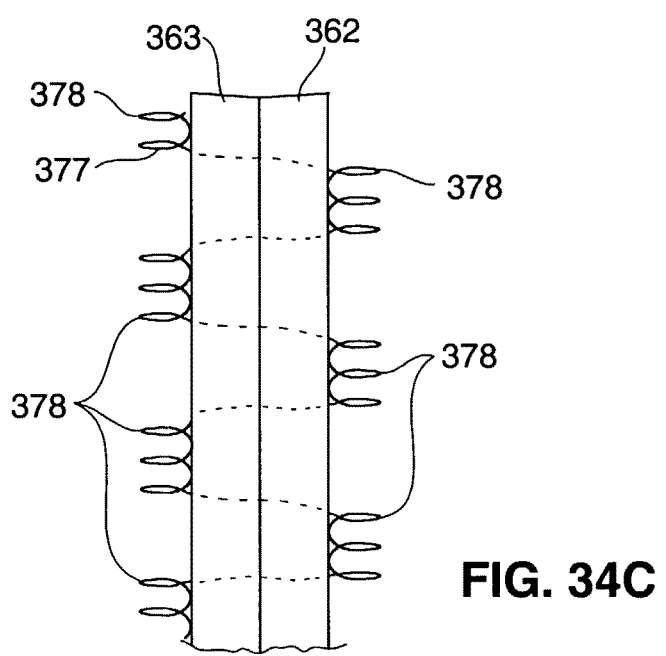

FIGS. 34A-C illustrate side perspective and side partial cross sectional views of another wound closure device and method for closing the opening formed in the stomach wall.

Figure 35:
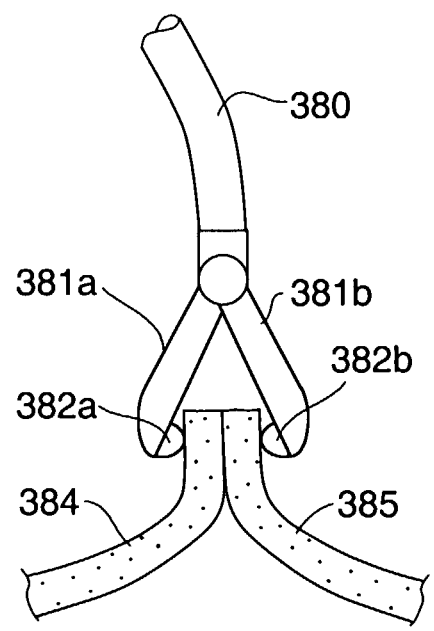

FIG. 35 is a side view of a tissue welding instrument in use according to an embodiment of the invention.

Figure 36A:
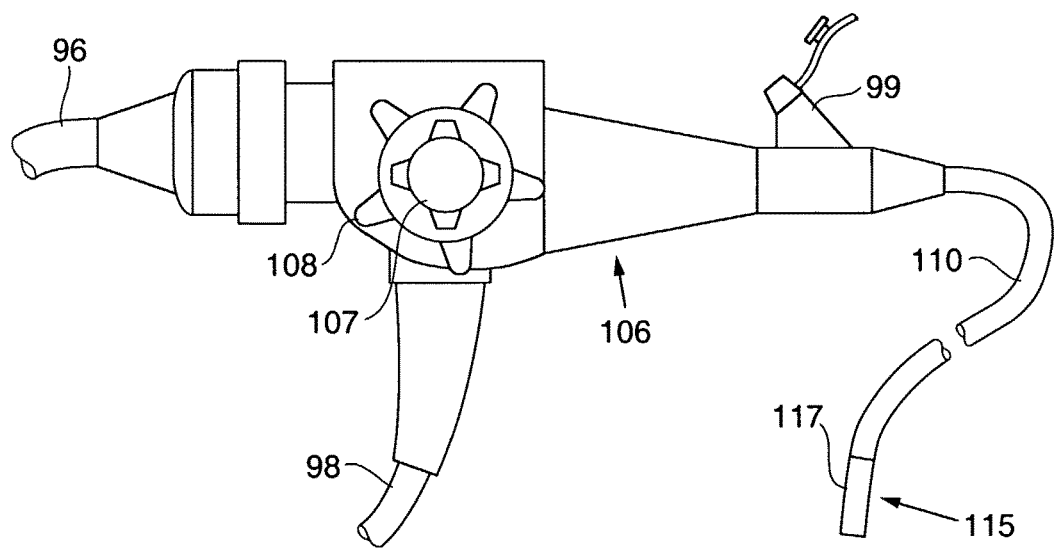

FIG. 36A is a side view of an endoscope to be used according to the present invention.

Figure 36B:
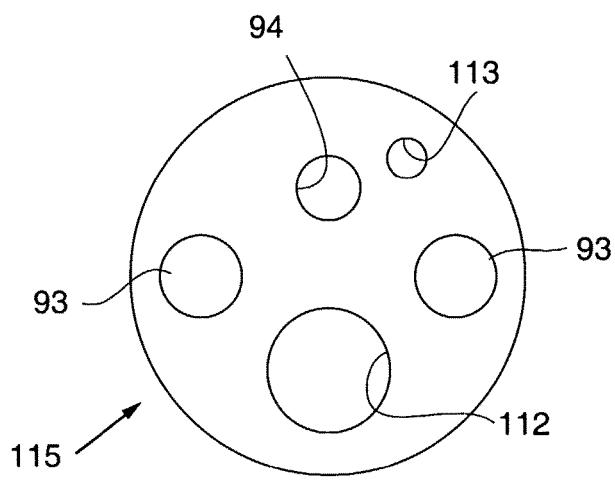

FIG. 36B is a front view of the distal end of an endoscope to be used according to the present invention.

Figure 37:
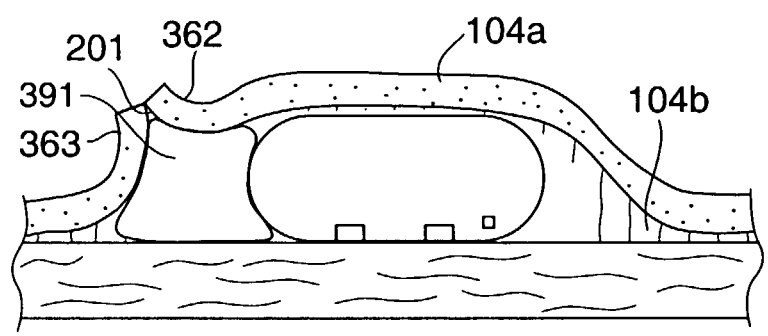

FIG. 37 illustrates a side partial cross sectional view of another wound closure device and method for closing the opening formed in the stomach wall.

DETAILED DESCRIPTION OF THE PREFERRED EMBODIMENTS

Figure 1A:
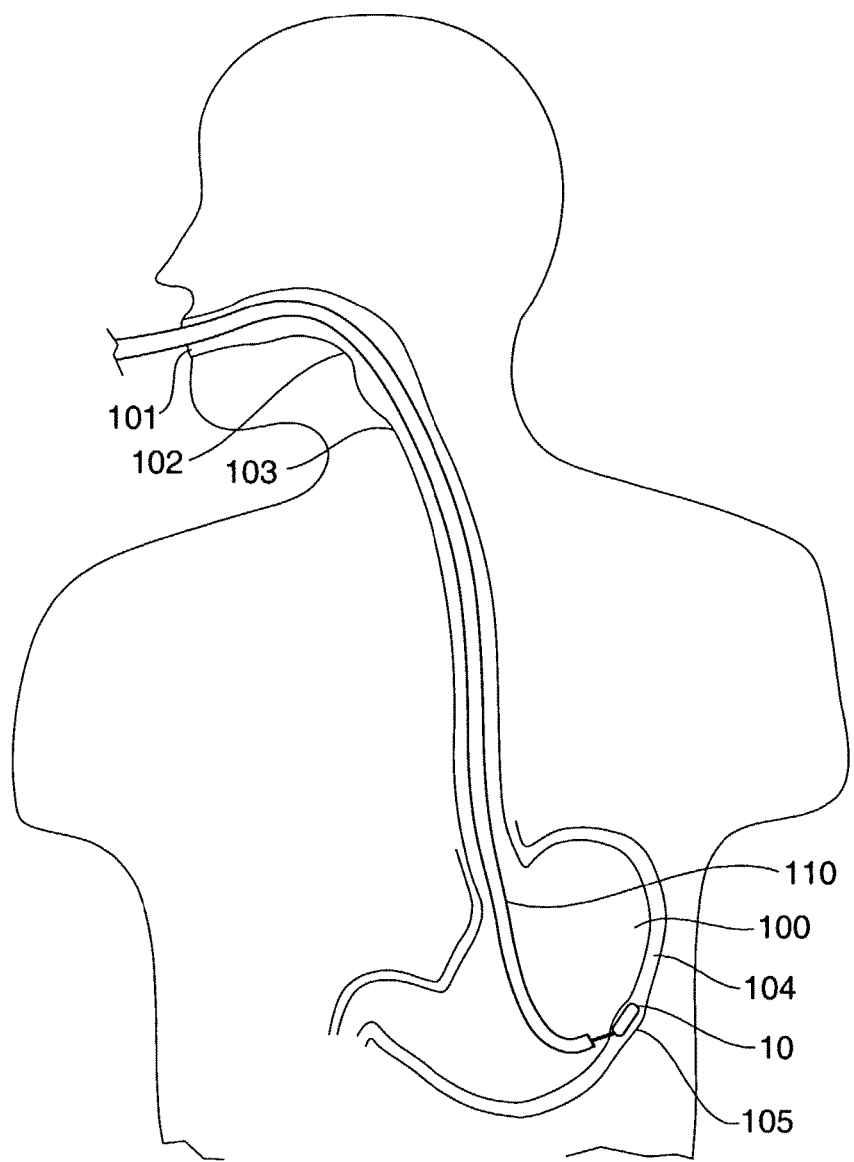
FIG. 1A is a partial cross sectional view of a system of a first embodiment of the present invention in use in placing an electric stimulator in a patient's stomach wall.
Figure 1B:
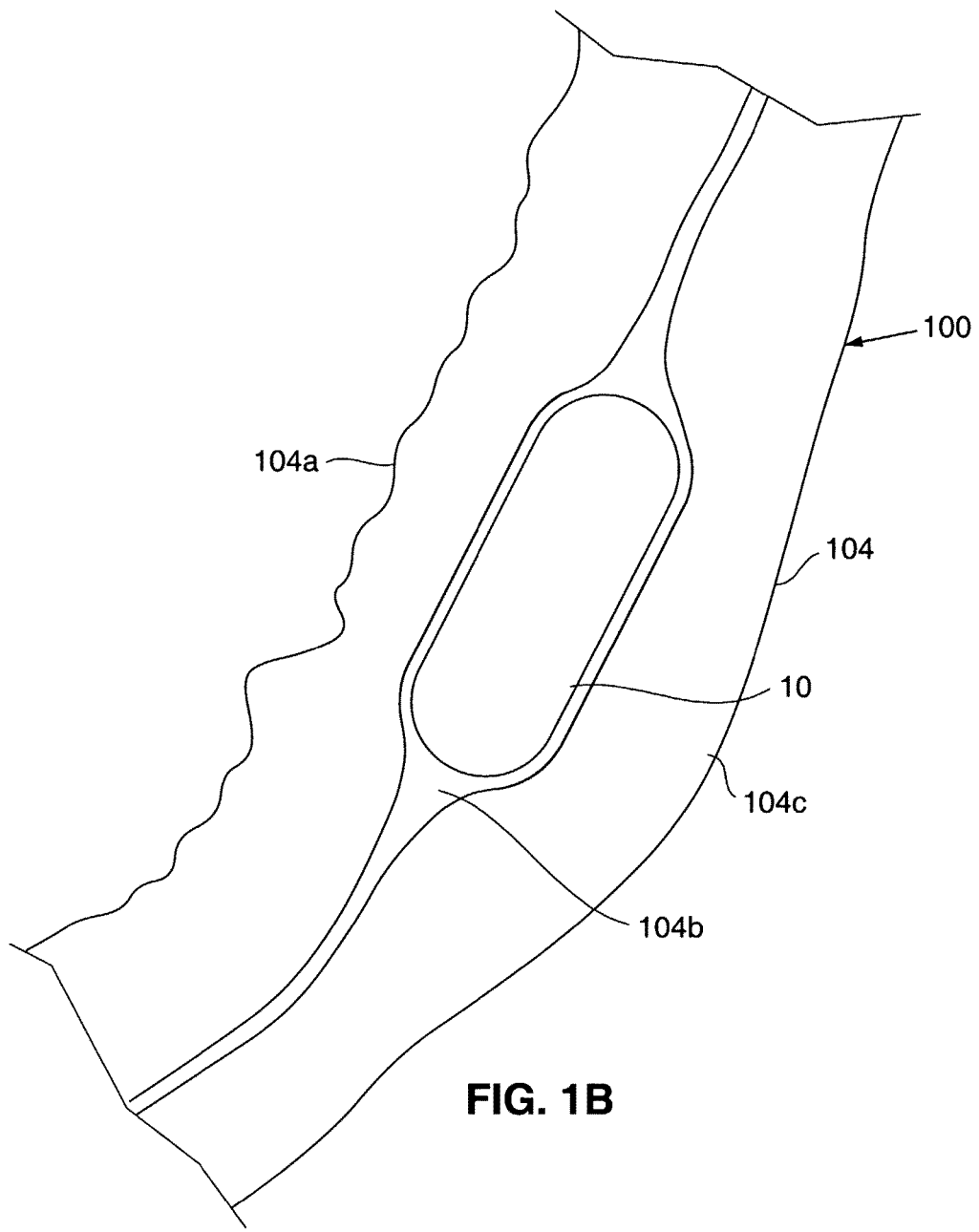
FIG. 1B is an enlarged partial cross section of the stimulator of FIG. 1A implanted in the submucosal layer of a stomach wall.

Referring to FIGS. 1A and 1B, a stimulator 10 is illustrated implanted in the stomach wall 104 of the stomach 100. The stimulator 10 lies within the submucosal layer of tissue 104b between the mucosal layer 104a and the muscle layer 104c. The muscle layer 104c comprises oblique, circular and longitudinal muscle layers.

According to one embodiment of a method of the invention, an endoscope and associated instruments are used implant a functional device in a submucosal layer of the stomach wall. An opening is formed in the mucosal layer to access the submucosal layer and the functional device is implanted through the opening into the submucosal layer. In one embodiment, the instruments are used to prepare a cavity or pocket in the submucosal layer at the selected site of the stomach wall, for implanting a functional device. In one embodiment, a bleb or blister is first formed in the submucosal layer of the stomach wall. A pocket is then formed in the bleb by dissecting the connective tissue of the submucosal layer. A stimulator device is then placed in the submucosal pocket so that stimulation electrodes are in electrical contact with a muscle layer of the stomach wall, i.e., one or more of the various muscle layers. If desired, the opening formed in the mucosal wall when accessing the submucosal layer, is then closed so that it may heal, enclosing the implant in the submucosal pocket. Various embodiments of the method for implanting a functional device in the submucosal layer of the stomach wall will be evident from the description of the implants and instruments below.

As illustrated in FIG. 1A, to implant the device in the stomach, an endoscope 110 is used with various instruments as will be described in more detail below. A flexible endoscope 110 is used to locate an implantation site 105 within the stomach 100 and implant the stimulator device 10 at the site 105 within the stomach wall 104 of a patient. The flexible endoscope 110 may be of the type that is typically used by gastroenterologists in treating the upper gastrointestinal tract and in accessing the esophagus or stomach. The endoscope allows the physician to visualize while performing procedures on the upper gastrointestinal tract. The flexible endoscope may be, for example, a flexible fiber optic endoscope utilizing optic fibers for imaging or a video endoscope that uses a CCD (charge coupled device) to provide video images. Such endoscopes typically include a fiber optic light guide and a complex objective lens at the distal end to focus the image.

As illustrated in FIGS. 36A-36B, the endoscope 110 comprises an elongate tube having a proximal handle portion 106 and a distal portion 115. The endoscope includes an aspiration/instrument channel 112 and irrigation/air channel 113. The aspiration/instrument channel 112 may be used for instruments if not otherwise required in a procedure. The aspiration/instrument channel 112 extends through the endoscope 110 and provides an opening through which surgical instruments may be inserted to reach the site 105. The instruments described with respect to the various embodiments herein may be introduced through the aspiration/instrument channel 112, through an opening in an overtube, or alternatively, the instrument may be inserted along side of the endoscope 110, for example in an attached guide or sheath. Fiber optic light sources 93 for illuminating the stomach site, extend through a fiber optic channel. A video lens 94 is located at the distal end of the endoscope, for receiving and focusing the image that is transmitted back through a channel in the endoscope 110. Corresponding video output 96, ports 98 for light source input, irrigation, and aspiration and port 99 for instruments, are located on the proximal handle portion 106. Knobs 107 and 108 are coupled at the proximal handle 106 for left/right and up/down steering mechanisms, respectively, that are used to steer the distal portion of the endoscope in a manner that is generally known to one of ordinary skill in the art. The distal portion 115 of the endoscope 110 includes a steerable distal end 117.

During the procedure the patient is given a numbing agent that helps to prevent gagging. As shown in FIG. 1A, the endoscope 110 is passed through the mouth 101, pharynx 102, into the esophagus 103 and into the stomach 100. If desired, an overtube may be used to protect the esophagus, which may become irritated with repeated insertion and removal of instruments. The overtube may also help prevent instruments and devices from inadvertently dropping into the trachea. In addition, an overtube may serve to protect the tools from the bacteria in the mouth and esophagus so that such bacteria are not passed on to the stomach wall. The overtube may also include additional channels for inserting additional instruments. As an alternative to an overtube, additional instruments may be attached to the outside of the endoscope and inserted through the esophagus.

Preferably the instruments inserted into the patient's stomach are coated with an antibacterial material, in particular, the instruments that are used to pierce or otherwise come in contact with the stomach wall. As illustrated in FIG. 1A the endoscope 110 is extended into the stomach 100 to a site 105 in the stomach 100 at which the stimulator 10 is being implanted. Additionally or alternatively, an endoscope or a tool inserted through the esophagus may be used to detect intrinsic gastric electrical activity to help pinpoint the optimal site for a stimulator and/or electrode implantation in the stomach wall. In such a case, sensing electrodes are coupled to the distal end of the endoscope or tool, with conductors extending out of the endoscope or patient's esophagus to a unit having a controller for receiving sensed electrical activity and identifying a surgical site for stimulator implantation.

Stimulators and Implants

Figure 2A:
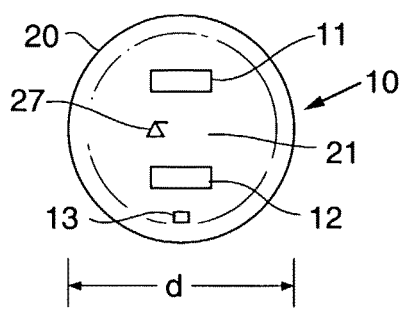
FIG. 2A is a top view of a first embodiment a functional device of the invention.
Figure 2B:
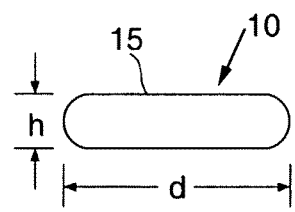
FIG. 2B is a side view of the functional device of FIG. 2A.

Referring to FIGS. 2A-2B, a stimulator 10 of a first embodiment is illustrated. The stimulator 10 is constructed in a disc-like shape. The stimulator 10 comprises a housing 20 having a relatively flat, broad top surface 21 with surface electrodes 11, 12 and a sensor 13 located thereon. The diameter d of the top surface is greater in comparison to the height h of the side (FIG. 2B) of the stimulator 10. The disc shape maintains the device in proper orientation so that the electrodes 11, 12 contact the muscle layer 104c of the stomach wall 104. FIG. 2B illustrates an aspect 15 of all side views of the stimulator 10. The aspect ratio of the aspect 15 is the width of the side view (diameter d) divided by the height h of the side view, and is greater than about one, preferably greater than about 1.4 and more preferably greater than about 1.8.

When implanted the electrodes 11, 12 are oriented so that they face and are in electrical contact with the muscle layer 104c of the stomach wall 104. The stimulator 10 includes a battery 144 (FIGS. 12 and 13) and electronic circuitry 25 (FIGS. 12 and 13) coupled to the electrodes 11, 12 and sensor 13. The electronic circuitry 25 and battery 144 provide stimulating electronic pulses through the electrodes 11, 12 to the stomach wall, sensing of relevant parameters and telemetry communication with an external unit such as a reader, recorder or controller as described in more detail herein. The housing 20 may also include a radiopaque marker 27 (e.g., sprayed onto a location in the housing 20) so that the device may be appropriately oriented when implanted, and so that its location and orientation may be identified after it has been implanted.

The housing 20 of the stimulator 10 is preferably constructed of a saline corrosion resistant material such as a medical grade titanium, tantalum or alloys of these or other metals. Alternatively, the housing may also be constructed out of suitable inert polymers, for example, from the polyolefin family, e.g., HDPE (high density polyethylene) PP (polypropylene), UHMWPE (ultra high molecular weight polyethylene), or fluoropolymer such as PTFE (polytetrafluoroethylene) FEP(fluorinated ethylene propylene) and other members. PMP (polymethylpentene), polysulfone, PMMA (polymethylmethacrylate) may also be used. The surface of the housing 20 is preferably coated with an antibiotic material, such as gentamicin or silver/silver salts coating. The electrodes 11, 12, are preferably constructed of a saline corrosion resistant material such as platinum, iridium, gold, tantalum, titanium, or any suitable alloys thereof or stainless steel. The housing or a portion of the housing, or the electrodes may be coated with a material that promotes encapsulation or tissue ingrowth such as, e.g., with P-15. Alternatively, the housing or electrodes may be coated with a material that resists tissue ingrowth, e.g., when it is desirable to easily remove the device with minimal tissue damage.

Figure 3:
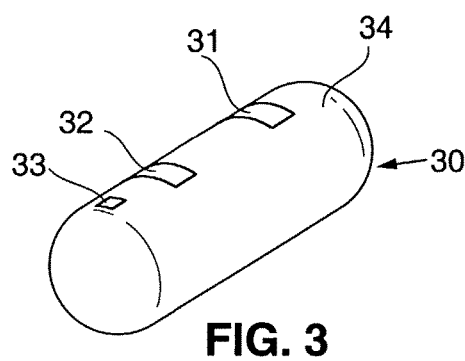
FIG. 3 is a perspective view of a second embodiment of a functional device of the present invention.

FIG. 3 illustrates a cylindrical shaped implantable stimulator 30 with rounded edges and comprising a housing 34 having electrodes 31, 32 and a sensor 33 located thereon. The cylindrical shape permits relatively easy delivery through the esophagus and into the stomach and implantation into the stomach wall due to its narrow geometry. The rounded configuration prevents damage to the stomach wall when implanted. Battery 144 and electronic circuitry 25 are included in the housing 34 to provide stimulation pulses, sensing and telemetric communication as described herein with reference to FIGS. 13 and 14.

Figure 4:
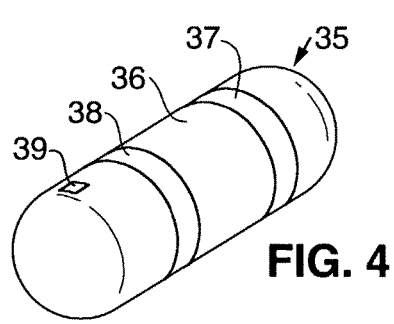
FIG. 4 is a perspective view of a third embodiment of a functional device of the present invention.

FIG. 4 illustrates a cylindrically shaped implant 35 comprising a housing 36 with ring electrodes 37, 38 and a sensor 39 located thereon. The cylindrical shape permits relatively easy delivery into the stomach and implantation into the stomach wall due to its narrow geometry. The ring electrodes 37, 38 provide contact with the muscle wall irrespective of the axial rotational orientation of the cylindrical housing 36. The electrodes 37, 38 and sensor 39 are coupled to electronic circuitry 25 and batteries 144 to provide stimulation pulses, sensing and telemetric communication as described herein with reference to FIGS. 13 and 14.

Figure 5A:
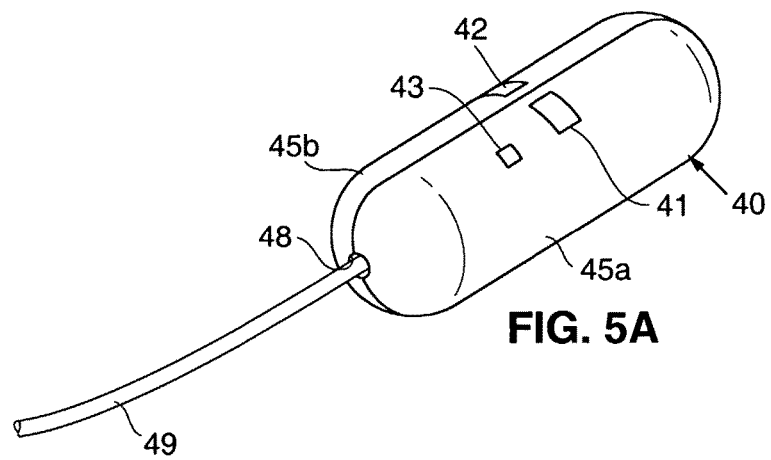
FIG. 5A is a perspective view of a fourth embodiment of a functional device in a configuration for delivery.
Figure 5B:
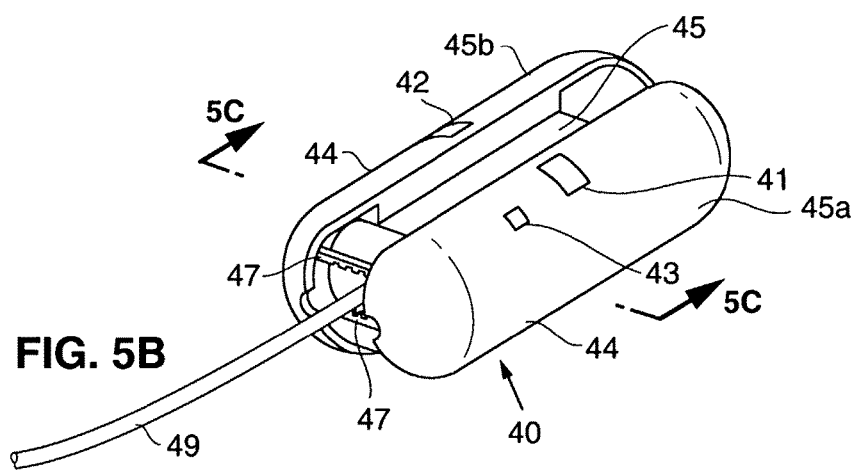
FIG. 5B is a perspective view of the functional device of FIG. 5A in an open position with an instrument for opening the functional device.
Figure 5C:
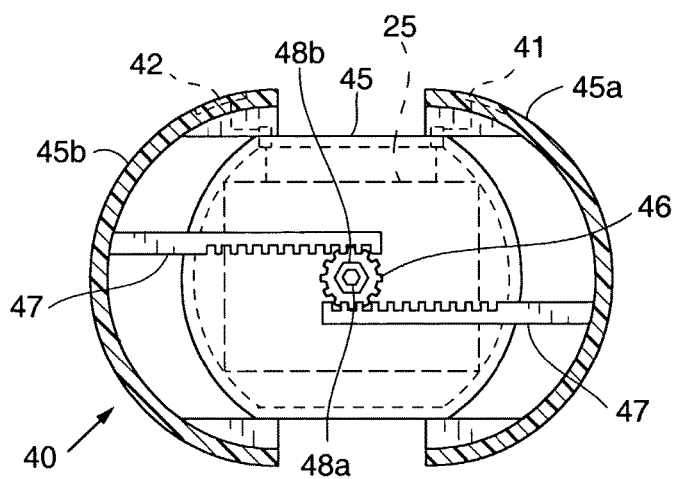
FIG. 5C is a cross-sectional view of the functional device of FIG. 5B with the cross section taken along the lines 5C-5C.
Figure 5D:
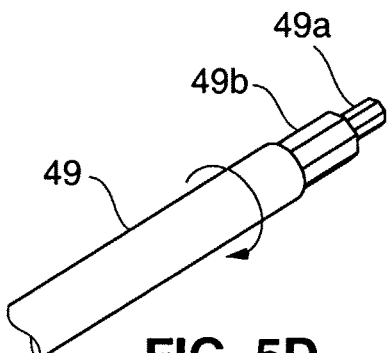
FIG. 5D illustrates an instrument to be used in accordance with the embodiment of FIGS. 5A-C.
Figure 5E:
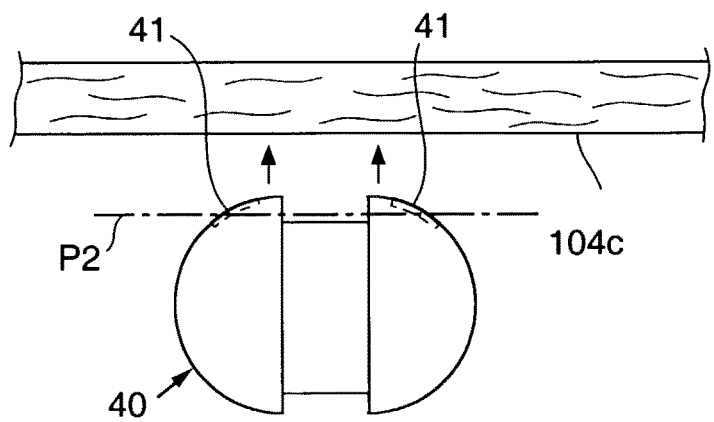
FIG. 5E is an end view of the functional device of Figure SB in its open position with the electrodes adjacent to an implant wall.
Figure 5F:
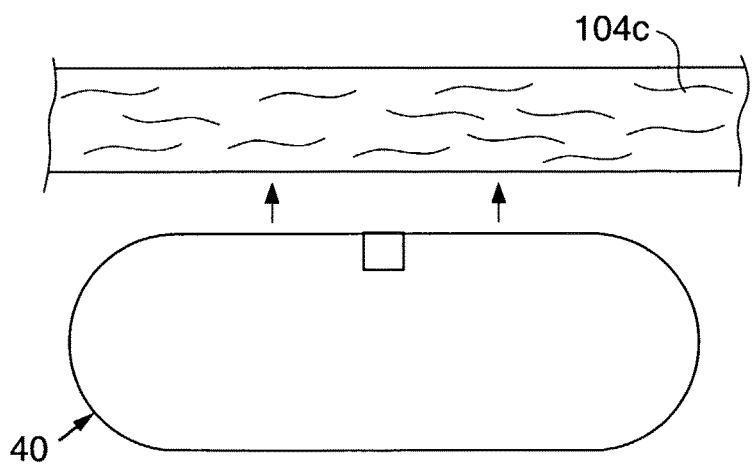
FIG. 5F is a side view of the functional device of FIG. 5B in its open position with the electrodes adjacent to an implant wall.
Figure 5G:
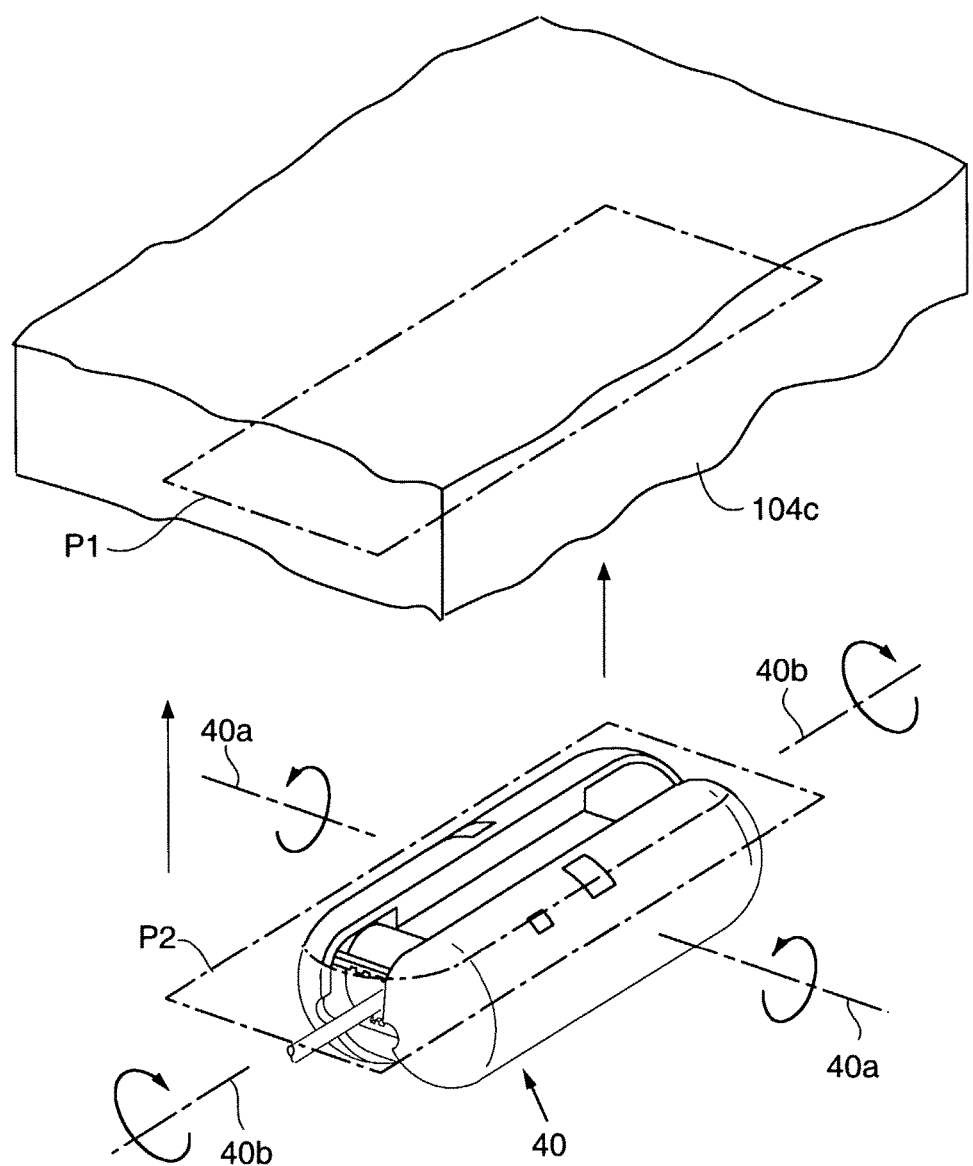
FIG. 5G is a perspective view of a stomach wall with an intended plane of tissue contact and the functional device of FIG. 5A in an open position illustrating a plane defined by electrodes on the device and various axes of potential rotation.

FIGS. 5A-G illustrate an alternative embodiment of the invention in which the implant's shape may be altered after implanting. According to this embodiment, once the device is implanted the shape is changed from having a relatively low profile or aspect ratio that permits introduction through the esophagus, to a relatively higher profile or aspect ratio for preventing device rotation within the submucosal pocket. The implant 40 comprises a housing 44 with an electrode pair 41, 42 and sensor 43 located on the housing 44. The electrode pair 41, 42 and sensor 43 are coupled to electronic circuitry 25 and a battery 144 for sensing, stimulation and telemetry as described herein with reference to FIGS. 13 and 14. FIG. 5A illustrates the implant 40 in a first and closed position and FIGS. 5B, 5C, 5E, 5F and 5G illustrate the implant 40 in a second and open position.

The housing 44 comprises two halves 45a, 45b slidably mounted on a core 45 that contains the battery 144 and electronic circuitry 25. In the implant's first position, two halves 45a and 45b are in a closed position with the halves 45a, and 45b together. An opening 48 in the housing 44 provides access for a magnetic hex key instrument 49. The hex key instrument 49 comprises concentric inner hex key 49a and outer hex key 49b that rotate with respect to each other. The opening 48 in the housing ends in an inner hex opening 48a for receiving the inner hex key 49a to stabilize the implant 40, and an outer hex opening 48b for receiving the outer hex key 49b for rotating the pinion wheel 46. The pinion wheel 46 engages racks 47 so that when the pinion wheel 46 is rotated, the halves 45a and 45b are opened or expanded to provide a wider device geometry that prevents rotation. Other mechanisms may be employed to open the device such as, e.g., a spring-loaded mechanism, pneumatic/hydraulic pistons, cams, etc.

In the first position, the implant has a relatively small profile that enables passing the implant into the stomach through the narrow esophagus. In this first position, the implant has a relatively small aspect when viewing its side view along axis 40b. This small aspect enables passing the implant through the esophagus. Once the implant 40 is placed within the stomach at a stimulation site 105 with the electrodes in contact with a desired portion of the stomach wall 104, the implant 40 is expanded to provide a geometry increasing the aspect ratio of the side-view of the device viewed along axis 40b (FIG. 5E) and by doing so, preventing rotation about axis 40b (FIG. 5G) and maintaining electrode contact with the desired portion of the stomach wall 104. The aspect ratio from the vantage of either axis 40a or axis 40b is greater than 1, preferable greater than about 1.4, and more preferably greater than about 1.8.

The muscle wall layer 104c of the stomach wall 104 defines at least one plane p1 on which an intended area of electrode contact lies. The axis 40a is parallel to the plane p1. Also the axis 40b is parallel to the plane p1. Thus the aspect ratio of the aspect viewed from the axis 40a (FIG. 5F) and the aspect ratio of the aspect viewed from the axis 40b (FIG. 5E) are sufficiently large to prevent rotation about either of the axes 40a, 40b (parallel to the plane p1) (FIG. 5G), and away from a position of intimate electrode contact with the muscle layer 104c within the submucosal pocket into which the stimulator or implant 40 is implanted.

The electrodes define at least one plane p2 (FIG. 5G) that may provide contact area for contacting the muscle layer 104c of the stomach wall 104. The axis 40a is parallel to the plane p2. Also the axis 40b is parallel to the plane p2. Thus the aspect ratio of the aspect viewed from the axis 40a (FIG. 5F) and the aspect ratio of the aspect viewed from the axis 40b (FIG. 5E) are sufficiently large to prevent rotation about either of the axes 40a, 40b (parallel to the plane, p2), and away from a position of intimate electrode contact with the muscle layer 104c within the submucosal pocket into which the stimulator or implant 40 is implanted. The aspect ratio in either of these variations, from the vantage of either axis 40a or axis 40b, is greater than one, preferable greater than about 1.4, and more preferably greater than about 1.8.

FIGS. 6A-C illustrate another embodiment of the invention in which the implant's shape may be altered after implanting. An implant 50 comprises a cylindrical housing 54 with a pair of wings 55 folded around the cylindrical housing 54 in a first position (FIG. 6A) in which the implant has a relatively small profile that enables passing the implant 50 into the stomach through the narrow esophagus. The implant 50 in a second position (FIGS. 6B and 6C) has its wings 55 unfolded to expose the electrodes 51, 52 and sensor 53 located on the housing 54. The unfolded wings 55 provide a means for preventing rotation of the implant 50 within the submucosal pocket into which it is implanted. The wings 55 are preferably made of a biocompatible elastic material such as, e.g., silicone, polyurethane, etc., and are bonded to the cylindrical housing 54.

FIG. 6A illustrates the implant 50 in its first position as it is inserted through an esophagus into a patient's stomach. An instrument 56 for grasping or holding the implant 50 is inserted through the channel 112 in the endoscope 110 with a grasper 57 at its distal end for grasping a knob 59 on the cylindrical implant 50 to grasp or hold the implant 50. A transparent sleeve 58 is placed over the distal end of the endoscope 110. The implant 50 is initially located within the transparent sleeve 58 in its first position with the wings 55 folded. The transparent sleeve 58 is placed in the submucosal pocket where the implant 50 is to be placed. The instrument 56 is rotated so that the electrodes 51, 52 face the muscle layer 104c adjacent the submucosa. The location of the implant 50 with respect to the stomach wall may be visualized through the endoscope 110 through the transparent sleeve 58. The implant 50 may also have a mark that enables the determination of the orientation of the implant 50 observed through the endoscope 110. Once in place, the grasping instrument 56 is advanced out of the endoscope 110 to extend the implant 50 from the transparent sleeve 58 at which time the elastic wings 55 expand, extend and open in place within the submucosal pocket (FIG. 6B). The anti rotation wings 55 maintain the electrodes 51, 52 in position facing the muscle layers of the stomach wall. As illustrated in FIG. 6C, once the implant 50 is in place, the grasper 57 releases the implant 50 and the instrument 56 is removed.

Figure 7:
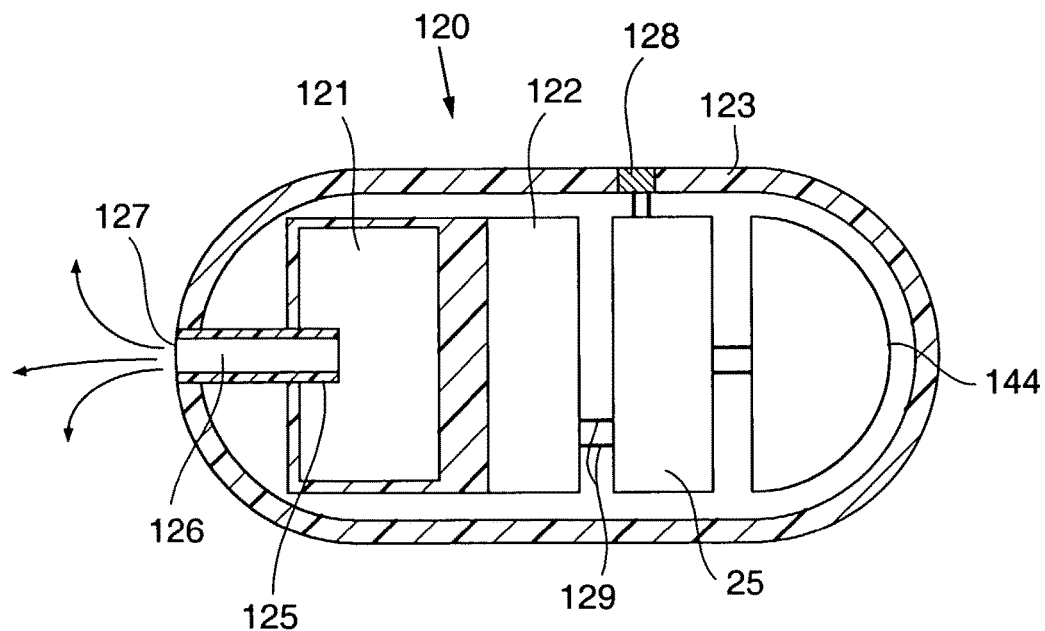
FIG. 7 illustrates a cross section of a sixth embodiment of a functional device of the present invention comprising a therapeutic agent delivery mechanism for implanting in the submucosal layer of the stomach wall.

FIG. 7 illustrates an alternate functional device 120 of the present invention for implanting in the submucosal layer of the stomach where the functional device comprises a drug or therapeutic agent delivery mechanism. The device 120 includes a housing 123 having a battery 144 and electronic circuitry 25. The electronic circuitry 25 is coupled to a drug reservoir 121 and pump 122 for delivering a drug through an outlet port 127 in the housing 123. A tubular wall 125 provides a conduit 126 from the reservoir 121 to the outlet port 127. The reservoir 121 is configured to hold a plurality of doses of a therapeutic agent that may be released according to a regimen or may be released continuously over time. The outlet port 127 opens into the submucosal layer when the device 120 is implanted. The supply of the therapeutic agent may also be replenished after the therapeutic agent has been depleted, for example, by delivering the substance through the outlet port 127 or other port into the reservoir 121, e.g., with a flexible endoscopic or laparoscopic microcannula. A sensor 128 on the housing 123 is coupled to the electronic circuit 25 and may be used to sense various parameters of the stomach or stomach wall, e.g., as described with respect to various embodiments herein.

In use, the electronic circuitry 25 controls the action of the pump 122 by delivering a control signal through connectors 129 coupling the electronic circuitry 25 to the drug pump 122. The electronic circuitry 25 may be preprogrammed to control drug or substance delivery according to a certain regimen or protocol, typically over a prescribed treatment duration. The electronic circuitry 25 may determine the timing and amount of drug to be delivered based on such a preprogrammed regimen stored in memory in the circuitry 25. Alternatively, the programs may be altered based conditions sensed by the sensor or other diagnostic information. The program may be telemetrically communicated to the electronic circuitry 25 by way of an external controller. Also the parameters of the drug delivery or the control of the delivery itself may be actuated by an external control signal or by an external controller. When a control signal from the electronic circuitry is delivered to the pump 122, the pump 122 delivers the drug from the reservoir 121, through the conduit 126 and out the outlet port 127.

Multiple Electrode Pairs and Multiple Stimulators

Multiple electrode pairs and multiple stimulators may be configured for use in a number of applications. A particular waveform, pulse or series of pulses may not be sustaining stimulation and contractions over a distance. Thus, the multiple electrode pairs may be used to stimulate in a sequence according to a program. Also the sequential stimulation may be useful in timing the propagation of the stimulation pulses or resulting muscle contractions. Also, the stimulation pulses sent by one set of stimulation electrodes may be used to trigger pulses to be sent by the receiving stimulator. Additionally, the electrodes and/or sensors at other locations may help provide information that allows adjusting of the stimulation parameters. Stimulation parameters may be selected based on sensed feedback from one or more of the sensors that are located adjacent the electrode pairs or with electrode pairs used to sense information. For example, stimulation by one set of electrode pairs at one location may or may not elicit a response at a second location where another set of electrode pairs and a sensor are located. Parameters sensed at the second location by the sensor or by the electrodes may indicate that an adjustment should be made in the stimulation at the first location or the second location to provide a desired response. For example, a pressure sensor or strain gauge at a second location may sense the existence of, ie., the presence or absence of contractions indicating that the stimulation is not effective in a particular area. The electrodes at the second or further location may be used to sense the signal delivered from the first electrode pair or may sense a resulting pacing signal or depolarization signal subsequent to and resulting from the initial stimulation signal. Presence, absence or degree of the signal may provide information that indicates the stimulation signal parameters should be changed. The parameters of the stimulation from the first location may be altered and programmed according to sensed feedback to optimize the stimulation parameters or sequence selection. Also in response, the stimulation at the second location may be adjusted to optimize the response. The sensed information may be telemetrically transmitted to an external receiver/processor that determines a new set of stimulation parameters and telemetrically programs the master stimulator in response. The multiple electrode pairs may be selected from at least three electrodes that may be configured into at least three independent electrode pairs at different times. Thus selectable electrode pairs are configurable to deliver electrically independent stimulating signals. A first electrode pair may be selected from the at least three electrodes by a control circuit based on a program to deliver a stimulating signal. Then according to a predetermined program or feedback, a second electrode pair may be selected from the at least three electrodes to deliver a second electrically independent stimulating signal.

The multiple electrode pair and multiple stimulator embodiments described herein may also be configured in a master/slave arrangement for propagating stimulation through a plurality of electrode pairs in a predetermined or concurrently determined pattern, wherein the master device triggers the stimulation signals provided by the slave devices.

One particular application of a master/slave device may be in a gastroparetic stomach, e.g., where the stomach is not effectively transmitting slow waves or burst pulses along all or a portion of the stomach wall. The master slave devices may be used to boost the slow wave or burst pulse signals if, when and where such pulses are failing to produce stomach wall contractions. According to one embodiment, the master device transmits either a telemetry signal or a stimulating signal that is received by one or more slave devices. The signal indicates that the master device has sent out a stimulation pulse. The master or slave device will then wait a predetermined time during which it is sensing whether a slow wave signal or a contraction is induced at the location of the slave device. Accordingly, sensor associated with the slave device may be used to sense presence or absence of slow wave signals, presence or absence of burst activity, or a resulting muscle contraction, e.g., by mechanically measuring contractions. If such a wave or contraction is not sensed then the slave device will deliver a stimulation pulse or the master device will determine an alternative stimulation protocol, program or sequence involving one or more slave devices. Thus in a series of slave devices, the stimulation pulses may be boosted at the particular slave device where the slow wave or contractions cease to effectively exist. According to one variation, the slave device that subsequently delivers a stimulation pulse, may then act as a master. The method may be repeated with subsequent slave devices until the desired slow wave propagation or contractions result.

Multiple electrode pairs may be in communication with each other either through wired communications or wireless communications. Various multiple electrode pair embodiments that may be arranged in various modes as described herein, are illustrated in FIG. 8, FIGS. 9A-C, FIGS. 10A-B, and FIG. 11.

Figure 8:
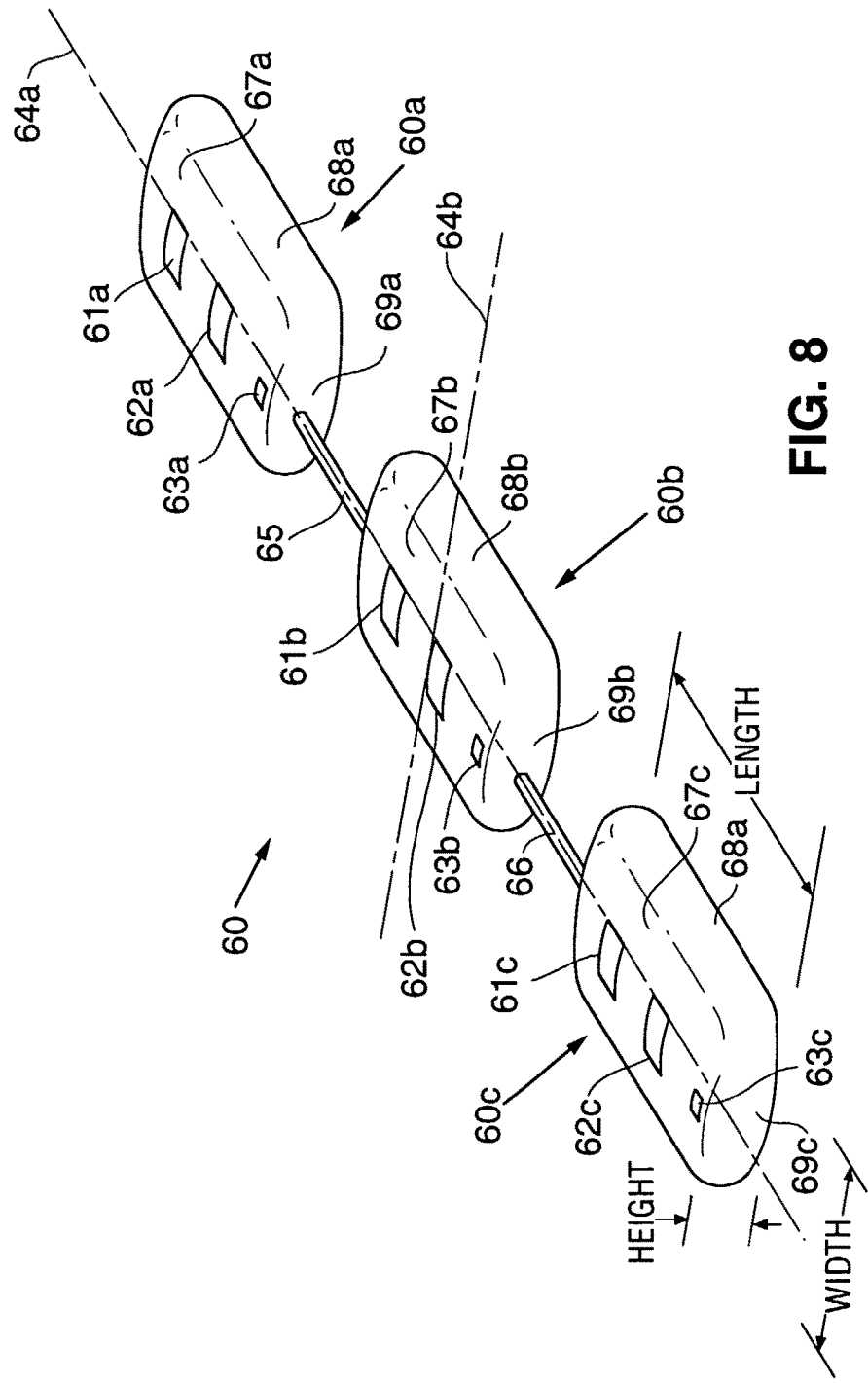
FIG. 8 is a perspective view of a seventh embodiment of a functional device of the present invention wherein the functional device has multiple electrode pairs.

FIG. 8 illustrates an implant 60 having a plurality of housings 60a, 60b, and 60c connected by flexible connectors 65, 66 that include electrical connectors for electrical communication between the housings 60a, 60b, and 60c. The connectors connect a chain of modules containing electronics and/or a battery, and carrying an electrode pair and/or sensors. The flexible connectors 65, 66 may comprise, e.g., insulated electrical wires or a hypotube containing wires; the connectors 65, 66 may be plastic; they may also comprise flexible coils; or they may be made of a superelastic material such as a Nickel-Titanium alloy. Each housing 60a, 60b, and 60c, has electrode pairs 61a, 62a; 61b, 62b; and 61c, 62c; and sensors 63a, 63b, and 63c respectively located on a broad top surface 67a, 67b and 67c of the housings 60a-c. When implanted the electrodes 61a-c, and 62a-c are oriented so that they face and are in electrical contact with the muscle layer 104c of the stomach. The geometry of implant 60 helps it resist rotation about axis 64a or axis 64b, within the submucosal pocket into which it is implanted. The aspect ratio of the implant 60 from the vantage point of axis 64a or axis 64b is greater than about one, preferably greater than About 1.4 and more preferably greater than about 1.8. The implant includes at least one battery 144 and one electronic circuitry 25, and, may include an electronic circuitry 25 and battery 144 for each of the housings 60a-c to supply electrical stimulation pulses to the electrode pairs 61a, 62a; 61b, 62b; and 61c,62c; sensing and telemetric communication.

Figure 9A:
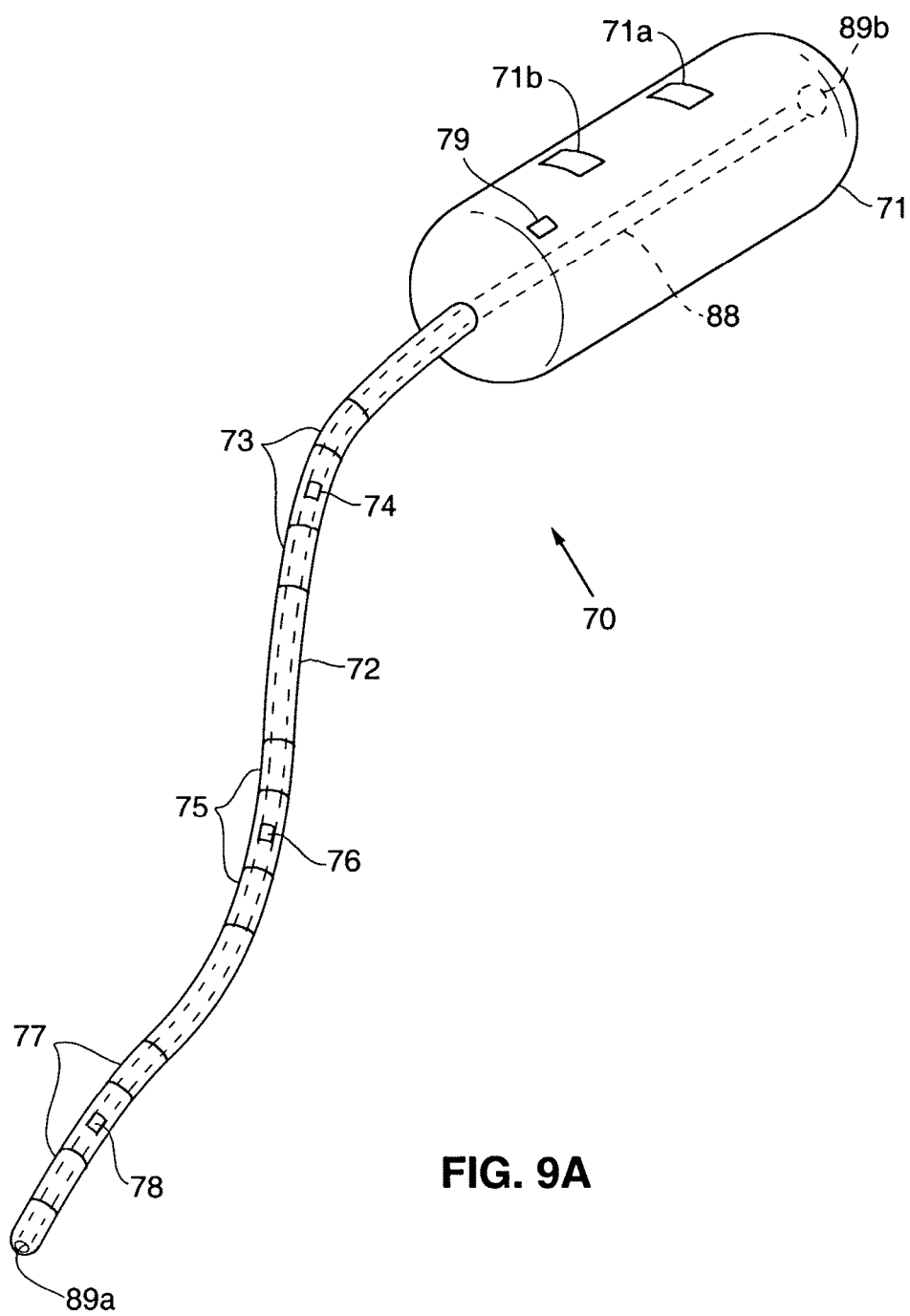
FIG. 9A illustrates an eighth embodiment of a functional device of the present invention wherein the stimulator has multiple electrode pairs.

FIG. 9A illustrates another embodiment of the invention in which the stimulator includes multiple electrode pairs. In this particular embodiment, a tail or elongate member 72 extends from the main device body or housing 71. The stimulator 70 comprises a housing 71 with an elongate member 72 attached to its end. The stimulator 70 includes a lumen 88 extending longitudinally through the elongate member 72 and the housing 71 from an opening 89a in the elongate member 72 to an opening 89b in the housing 71. The elongate member 72 comprises a plurality of electrode pairs, 73, 75, 77 and sensors 74, 76, 78 located between each of the electrode pairs 73, 75, 77 respectively. Each of the electrodes 73, 75, 77 and sensors 74, 76, 78 are coupled to electronic circuitry 25 and battery 144 as described in detail herein with reference to FIGS. 13 and 14, by way of insulated electrical connections extending through the elongate member 72 into the housing 71 where the electronic circuitry 25 and battery 144 are located. An additional sensor 79 is provided on the housing 71 for sensing parameters of the environment or tissue adjacent the housing 71. The sensor 79 is also electrically coupled to the electronic circuitry 25.

Figure 9B:
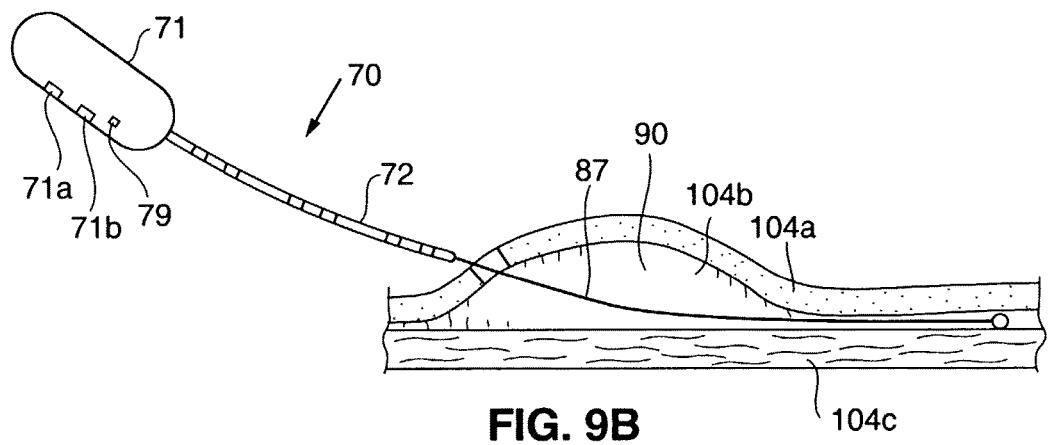
FIG. 9B illustrates a side partial cross sectional view of the implant of FIG. 9A as it is being implanted in a submucosal pocket.
Figure 9C:
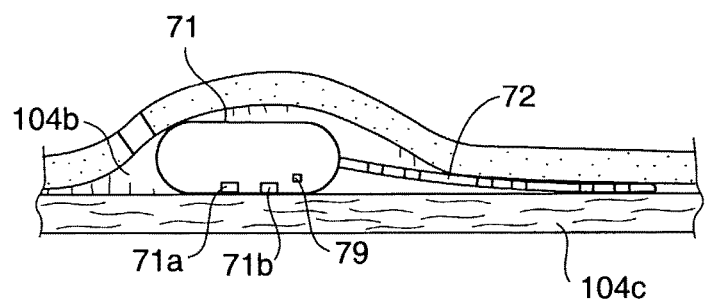
FIG. 9C illustrates a side partial cross sectional view of the implant of FIG. 9A in place in the submucosal pocket.

FIGS. 9B and 9C illustrate a method of implanting the stimulator 70 of FIG. 9A. In FIG. 9B, a guidewire 87 has been placed into a pocket 90 formed in the submucosal layer 104b. The placement of the guidewire 87 and preparation of the pocket 90 is done in a similar manner as the preparation of the pocket shown in FIGS. 20A-20G. After the pocket 90 has been prepared, the dissection instruments are removed, leaving a guidewire 87 in place. The stimulator 70 is placed over the guidewire 87 with the guidewire 87 extending through the lumen 88 of the stimulator. The elongate member 72 placed over the guidewire first with the housing 71 following the elongate member 72 as the stimulator is placed into the pocket 90. As illustrated in FIG. 9C, the stimulator 70 is in place in the pocket 90 and the guidewire is removed through openings 89a and 89b in the stimulator 70.

As an alternative to FIGS. 9A-C, FIGS. 10A-B illustrate a variation of a device having an elongate member with multiple electrode pairs. According to the embodiment, the stimulator 680 comprises a housing 681 and a removable attachable elongate member 692. The housing 681 includes a needle 684 for attaching the device to a stomach wall 104. The housing 681 includes an open chamber 682 for receiving a portion of the stomach wall 104 for attachment. The chamber 682 includes an opening 687 coupled to a vacuum pipe 688 external to the chamber 682 of the housing. The vacuum pipe 688 has an open proximal end 689 for coupling through an elongate tube to a vacuum source.

The needle 684 extends from a first proximal side of the device 683, distally through the chamber 682 piercing the stomach wall 104, to an opposite distal side of the device 686. A knob 685 is located on the outside of the first side 683 of the device 680. The knob 685 enables an instrument to grasp and advance or retract the needle 684 into or from the housing 681. The housing 681 contains electronic circuitry 25 and a battery 144 that are coupled to each other by connectors 691.

The device 680 is attached to the stomach wall by applying a suction though vacuum pipe 688 to chamber 682 to draw a portion of the stomach wall 104 into the chamber 682, and then attaching the device 680 by advancing the needle 684 distally through the tissue in the chamber 682. As the needle 684 extends through the chamber 682, it pierces through the stomach wall from the inside of the stomach wall to the outside through a fold in the stomach wall 104 and back through the stomach wall to the inside of the stomach wall 104.

Figure 10A:
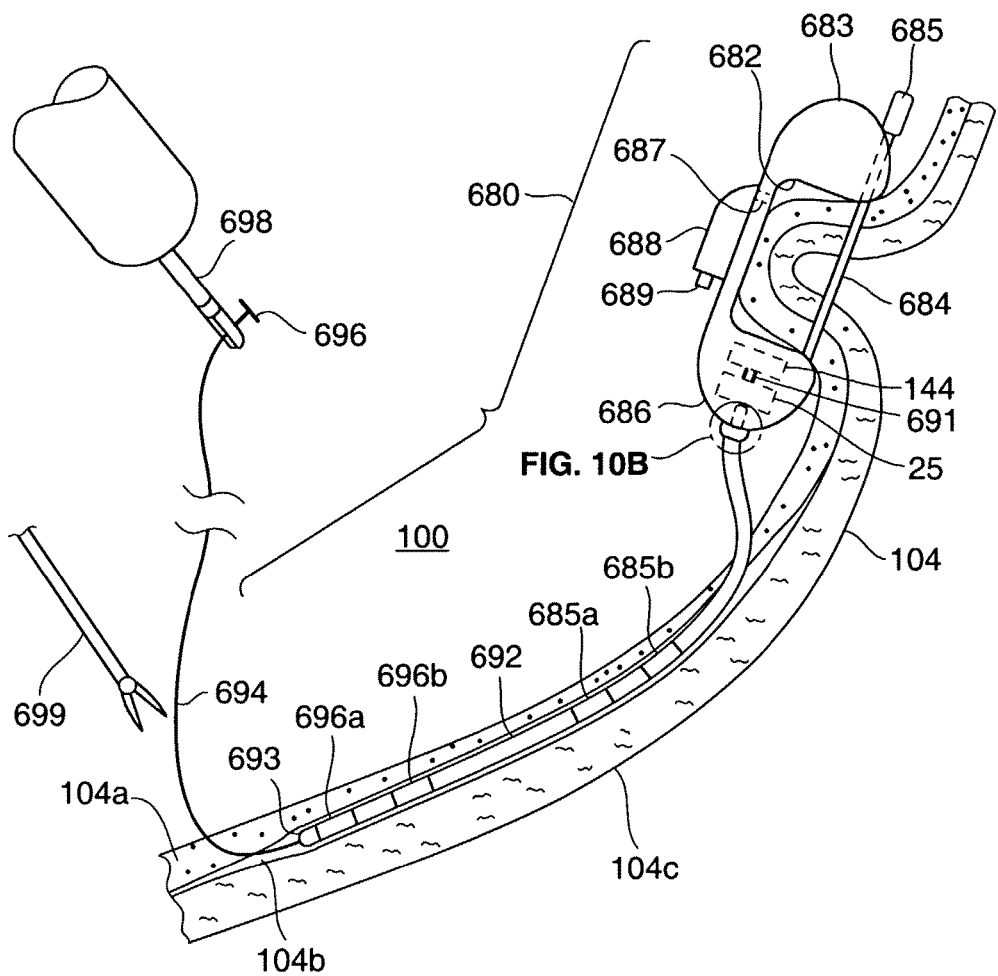
FIG. 10A illustrates a ninth embodiment of a functional device of the present invention in which the device has multiple electrode pairs.
Figure 10B:
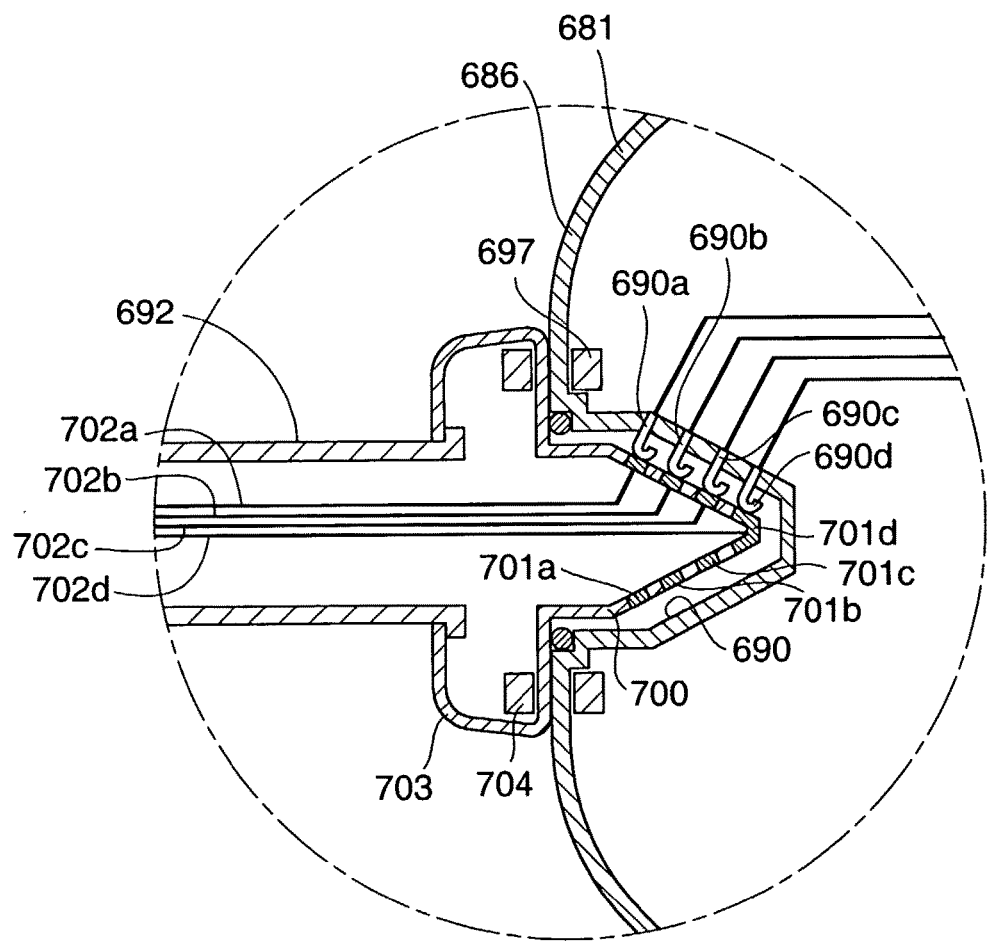
FIG. 10B illustrates an enlarged view of the electrical connector between the housing and the elongate member or the stimulator illustrated in FIG. 10A

The stimulator device 680 further comprises an elongate member 692 connected to the housing 681 by connector 700 show in more detail in FIG. 10B. The elongate member 692 includes bipolar ring electrode pairs 695a-b, 696a-b located at spaced locations along the elongate member 692. The electrodes 695a-b, 696a-b are coupled to electronic circuitry 25 within the housing 691 by way of connectors as described with reference to FIG. 10B. The multiple electrodes and electronic circuitry may be configured in a similar manner as the multiple electrode pairs described above. Additional electrode pairs may be used and the elongate member may extend through a substantial portion of the submucosa in the greater curvature of the stomach.

The elongate member 692 may be removably attached to the housing 681 of the device 680 through male connector 700 so that the electronics and batteries may be replaced by removing the housing 681 while leaving the elongate member 692 in place. A new housing with new batteries and electronic circuitry may subsequently be implanted and attached to the elongate member 692. The male connector 700 is located on the proximal end of the elongate member 692 and has electrical contact rings 701a-d coupled to contacting electrical wires 702 a-d extending distally through the elongate member 692 to electrodes 696a-b and 695a-b respectively. The housing 691 includes a female connector 690 located on the distal end 686 of the housing 681 for receiving the male connector 700. The female connector 690 comprises electrical contacts 690a-d that are coupled through wires to the electronic circuit 25 in the housing 681. The distal end 686 of the housing 681 includes a magnet 697 for removably coupling with the elongate member 692. The elongate member 692 includes a flanged portion 703 that engages the distal end 686 of the housing 681. The flanged portion 703 includes a magnet 704 that engages the magnet 697 on the housing 681. When the connectors 690, 700 are connected, the electrical contacts 690a-d are in electrical contact with the ring contacts 701a-d to provide electrical communication between the electrodes and the electronic circuit 25.

To implant the elongate member 692, a suture 694 or wire attached to the end 693 of the elongate member 692 may be placed through a portion of the stomach wall with a hollow needle so that a T-shaped end 696 extends back through the mucosa 104a and inside the stomach 100. The suture 694 is then pulled through the stomach wall 104 where the elongate member 692 is to be implanted, using an endoscopic grasping tool 698 that grasps the T-shaped end 696 of the suture 694, drawing the elongate member 692 into the submucosa 104b. The suture 694 is then cut using an endoscopic cutting instrument 699.

To remove the elongate member 692 from the housing 681, the elongate member 692 is stabilized using an endoscopic grasping tool while the housing 681 is removed using another endoscopic grasping instrument.

Figure 11:
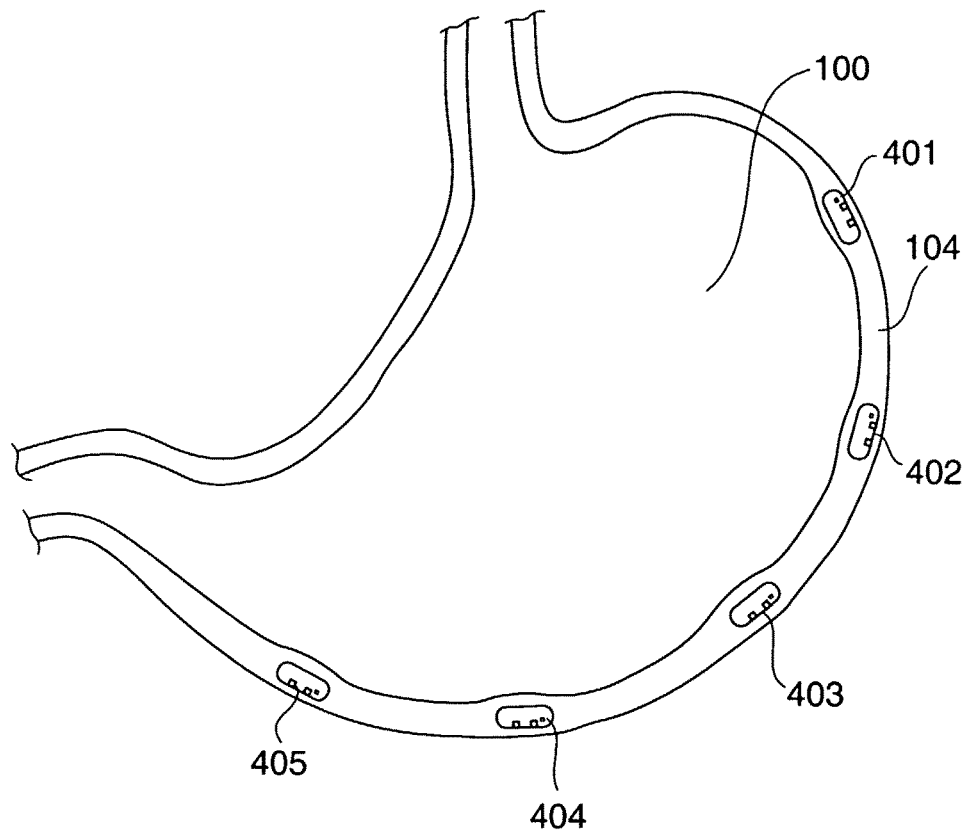
FIG. 11 is a partial cross section of a master/slave arrangement of stimulators implanted in a stomach wall.

Referring to FIG. 11 a master/slave arrangement of stimulators is illustrated. The stimulators 401-405 are implanted in submucosal pockets in a manner consistent with the procedures and instruments described herein. The stimulators may be attached to the stomach wall by other means, such as, for example, by attaching the stimulator using an anchor to the stomach wall. A first stimulator 401 is implanted, e.g., at the fundus/body transition on the greater curvature of the stomach. Additional stimulators 402, 403, 404, and 405 are implanted e.g., in sequence, more distally on the greater curvature.

The stimulators 401-405 can be programmed to function as a master device or a slave device. In one embodiment, initial commands, e.g., initial stimulation or command signals received by the slave devices, are dictated by the device designated as the master device. In turn, the slave devices follow the commands of the master device. The master slave arrangement also may provide a low power consumption method of communication between the devices. This method of communication between devices involves sensing of the device electrical pulses, which are conducted through the stomach tissue.

The multiple electrode pairs as illustrated in FIG. 11, are on individual stimulators 401-405 that are endoscopically implanted in a series along the greater curvature of the patient's stomach from the fundus to the antrum and used to stimulate, i.e, to effect peristalsis by sequential electrical stimulation. Using an external programmer and communication via RF telemetry, the most orad device (stimulator 401) is identified by a serial number or other identifier, and designated as master device. The other stimulators 402-405 are also identified and designated, in the aborad direction as a first slave, second slave, third slave, and fourth slave. The master stimulator 401 will start to electrically stimulate the stomach at a set frequency. Each master device electrical stimulation pulse that is conducted through the stomach tissue, will almost immediately (negligible delay) be sensed by the slave devices 402-405. The slave devices 402-405 will in turn emit an electrical stimulation pulse with a set time delay determined by their order (i.e., first, second third or fourth slave). The slave devices 402-405 may also have a set refractory period that begins after receiving the first electrical pulse delivered by the master device 401, so as not to respond to the electrical pulses of the other slave devices. The first slave's time delay will be the shortest. The fourth slave's time delay will be the longest. This sequential electrical stimulation of the stomach using the implanted stimulators 401-405 may, e.g., induce an artificial peristaltic wave propagating from the fundus to the antrum. One advantage of this method of communication between stimulators is that the amount of energy required is significantly less than if each stimulator's stimulation pulse was triggered by an RF telemetry communication from an external transmitter In a variation of an embodiment, the master device 401 emits a burst of electrical stimulation pulses to be duplicated by each of the slave devices 402-405, with an individually set time delay. The slave devices may be programmed to sense and count the fast burst pulse originating from the master. After no pulse is received anymore within a set time interval after receipt of the last pulse, the set refractory period of the slave device will start and the slave will emit a duplicate of the master signal after the set time delay.

The slave devices may also be capable of measuring a parameter of the sensed first stimulation signal that indicates the effectiveness of the stimulation signal, and respond accordingly to optimize the stimulation signal delivered by the slave device. The slave devices 402-405 may also respond to a sensed parameter indicating that the first stimulation pulses have or have not effectively been delivered, e.g., by a pressure transducer measuring contractions of the stomach, or by detecting or failing to detect a resulting inherent pacing signal (as opposed to the original stimulation signal). The stimulators 401-405 may be capable of being either a master or slave device. The stimulators' functions may be selected before or after the stimulators 401-405 have been implanted, to provide a number of possible configurations.

Electronic Circuitry, Stimulation, Sensing and Telemetry Communication

Figure 12:
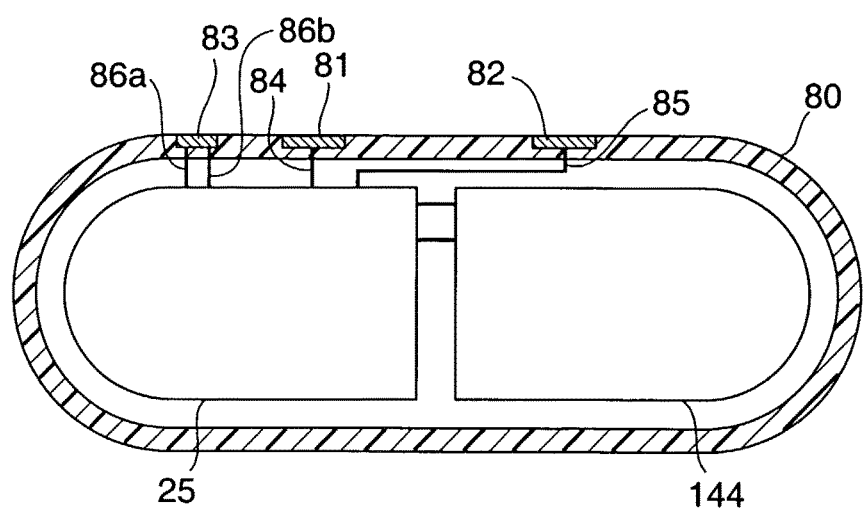
FIG. 12 illustrates a cross section of a stimulator showing exemplary electrical connections between the electronic circuitry and the surface electrodes of the stimulator.

Referring to FIG. 12 a cross section of an implant 80 with electronic circuitry 25 and battery 144 is illustrated. The electronic circuitry 25 and battery 144 described with respect to FIG. 12 are also used or may be used in connection with any of the other implants or stimulators described herein. The battery 144 is coupled to the electronic circuitry 25 to provide power to the circuitry 25 for sensing, telemetry and stimulation pulses. The electronic circuitry 25 is electrically coupled to electrodes 81, 82 and sensor 83 through connectors 84, 85, 86*a*, and 86*b*, respectively. Other electrical connection means between the surface electrodes, sensors and the electronic circuitry are contemplated by the invention and may be used in any of the embodiments described herein. The electronic circuitry 25 is described in more detail in FIG. 13.

Figure 13:
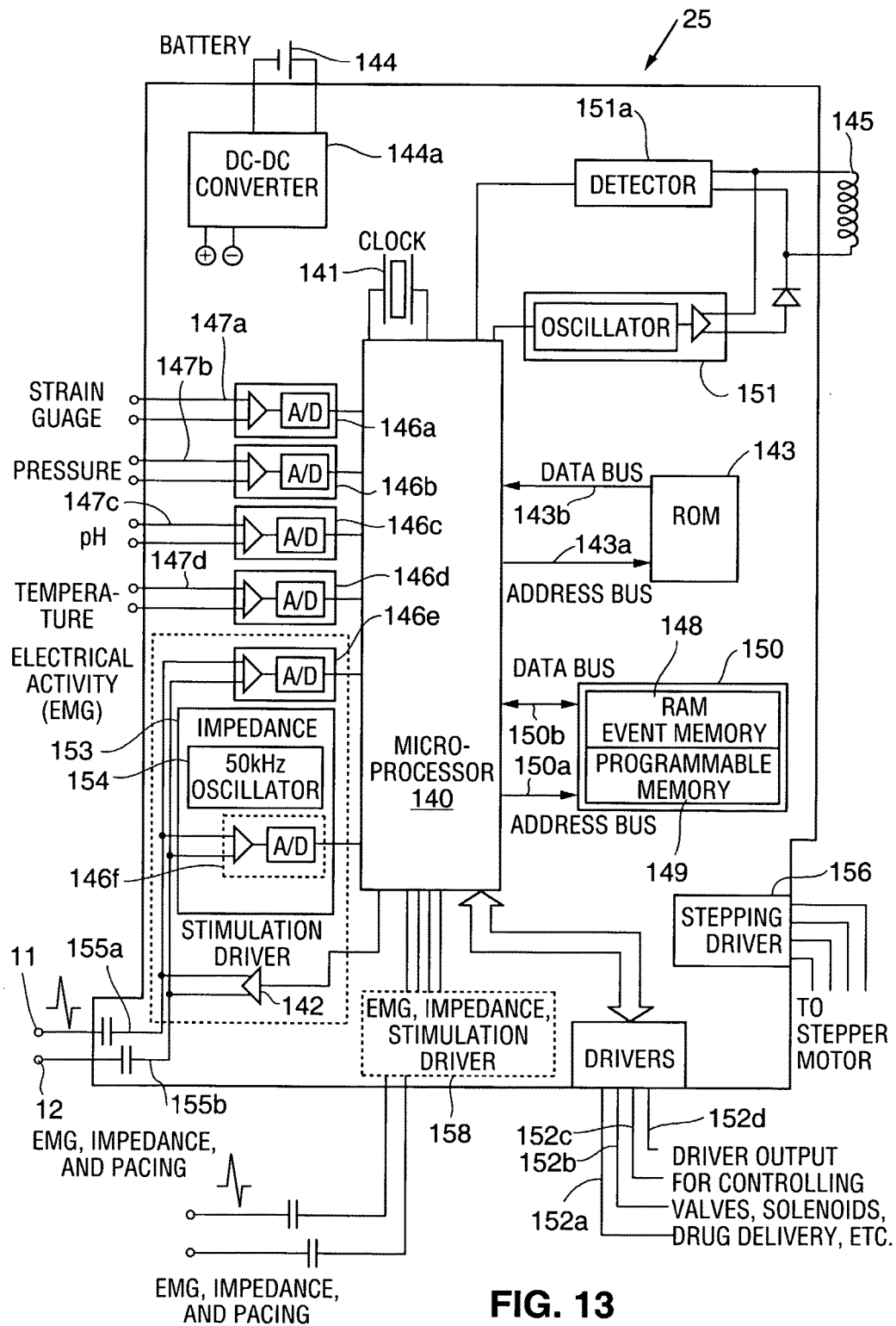
FIG. 13 illustrates a schematic diagram of the circuit of an electronic stimulator of the present invention.

Referring to FIG. 13, the electronic circuitry 25 is illustrated. In use, once the stimulator or implant (e.g., 10, 30, 40, 50, 60, 70, 80, 350, or 337) is deployed, electrical stimulation is to electrodes (11, 12, 31, 32, 37, 38, 41, 42, 51, 52, 61*a*, 62*a*, 61*b*, 62*b*, 61*c*, 62*c*, 73, 75, 77, 81, 82, 351 or 352) through electronic circuitry 25. Electronic stimulation may be provided for various therapeutic or diagnostic purposes. The electrical stimulation patterns of the implant are either pre-programmed, can be externally programmed via telemetry, or are autonomously controlled using incorporated sensors to provide feedback information.

The sensors of the implants are adapted to sense parameters of the stomach. The sensing may be used to determine a condition of the stomach that may indicate that stimulation should or should not be provided, i.e., whether to turn the stimulator on or off and what stimulation parameters to use. The sensing may also be used to provide information, for example on whether the stimulation is providing a desired response or how effective given stimulation parameters may be. The sensor may be, for example, a sensor for measuring contraction in the stomach such as a strain gauge, pressure sensor or electrical sensor.

The programming, monitoring and reprogramming of the stimulator may be controlled in part by an external controller that communicates with the stimulator via telemetry.

Figure 15A:
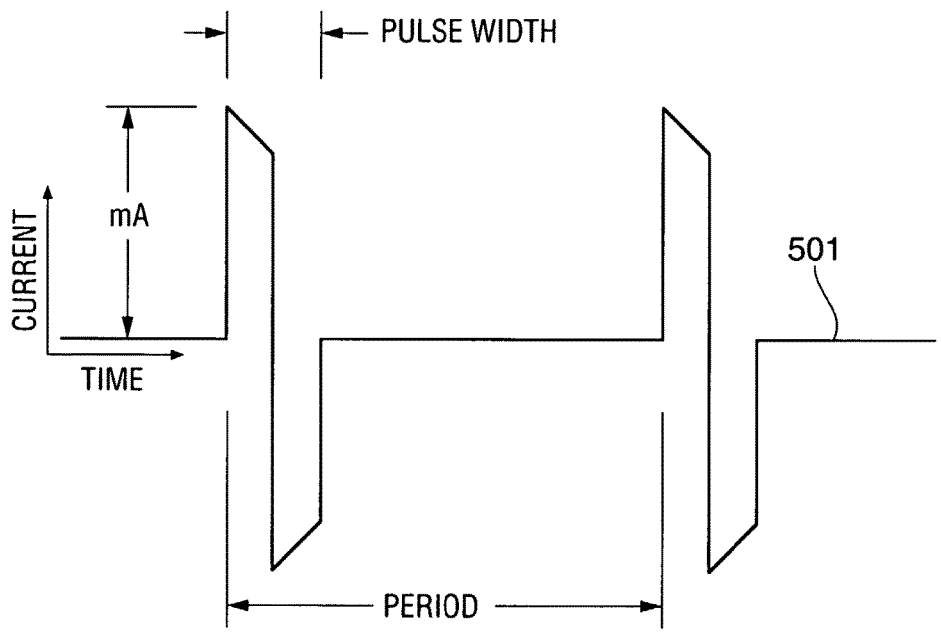
FIGS. 15A and 15B illustrate exemplary stimulation waveforms that may be delivered according to the invention.
Figure 15B:
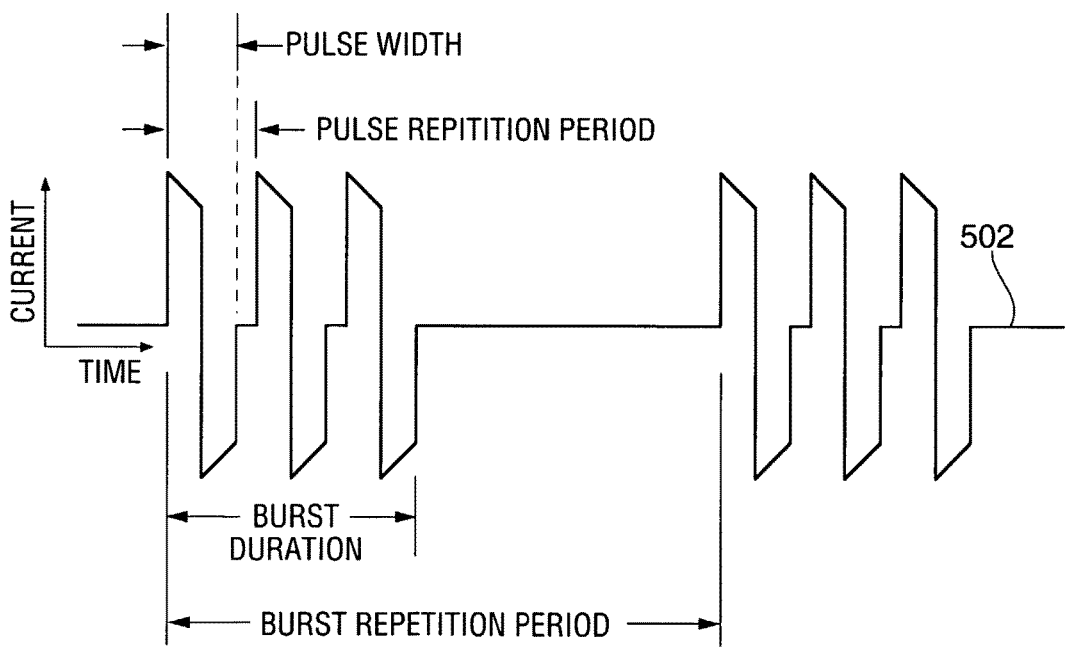

The electronic circuitry 25 is capable of producing various types of programmable waveforms. FIGS. 15A and 15B illustrate examples of stimulation waveforms that may be used in stimulating the smooth muscle layer of the stomach wall. FIG. 15A illustrates a waveform design for stimulating the stomach wall at a pacing rate. In one embodiment, the waveform 501 has a pulse amplitude of 1 to 30 mA, a pulse width of between 0.1 and 500 ms, and a frequency of about between 2 to 12 cycles per minute (this corresponds to a repetition period of between 5 to 30 seconds). FIG. 15B illustrates an alternative waveform design for stimulating the stomach wall. The waveform 502 utilizes bursts of pulses rather than a single pulse. The burst repetition rate is selected, preferably, to be between about 2 to 12 cycles per minute (this corresponds to a burst repetition period of between 5 to 30 seconds). The duration of a pulse in this example is between about 100 µs and 20 ms, and has an amplitude of about 1-30 mA. The frequency of the burst pulses during a burst period is about 50 Hz to 10 KHz corresponding to a pulse repetition period of 100 µs to 20 ms. The burst duration can vary from about 0.1 ms to 1 second. As is well known to those skilled in the art, there are many different types of electrical stimulation programs and strategies which can be utilized for providing electrical stimulation parameters through the circuitry 25, the principal focus being providing electrically stimulating parameters for the stomach. Stimulation may also be done utilizing phasic, unipolar or asymmetric stimulation waveforms.

One embodiment of the electronic circuitry 25 is illustrated in FIG. 13. The electronic circuitry may be on a chip or otherwise have a standard configuration that may be used in a number of different diagnostic or therapeutic functions in various embodiments of the functional device. The electronic circuitry 25 of the stimulator is located in the housings of the various implants described herein. The circuitry 25 comprises, a microprocessor or controller 140 for controlling the operations of the electronic circuitry 25, an internal clock 141, and battery device 144 such as a pair of lithium iodine batteries for powering the various components of the circuitry 25. As such, the controller 140 and battery device 144 are coupled to each of the major components of the circuit as would be apparent to one of ordinary skill in the art. The controller 140 is coupled to stimulation driver 142, which is coupled to stimulating electrodes 11, 12 (or any of the other electrodes described herein for delivering stimulation pulses) that are used to provide electrical stimulation in accordance with programmed parameters The controller 140 is coupled to ROM 143, which contains the program instructions for the controller 140 and any other permanently stored information that allows the microprocessor/controller 140 to operate. The controller 140 addresses memory in ROM 143 through address bus 143*a* and the ROM 143 provides the stored program instruction to the controller 140 via data bus 143*b*. The controller 140 controls the RF coil 145, which communicates with an external control or programming device 160 (FIG. 11), preferably via a modulated RF signal. Processor 140 is coupled to a buffered oscillator 151 that provides an RF signal to be emitted from the RF coil 145. The RF signal is preferably at about 100 kHz to 5 MHz so that the signal is efficiently transmitted through tissue. The controller 140 controls the oscillator 151 and provides data, for example, various sensed data such as pressure, pH, temperature, strain, impedance, electrical activity (EMG) etc., to be modulated with the RF signal to be delivered through the RF coil 145. When the RF coil 145 is receiving an external telemetry signal, the buffered oscillator 151 is disabled. Telemetry signals received on the RF coil 145 are detected in a detector circuit 151*a* and to communicated controller 140. The detector circuit 151*a* is preferably selected based on the modulation used for telemetry signals.

One or more sensors 147*a* (e.g., strain gauge), 147*b* (e.g., pressure), 147*c* (e.g., pH), 147(*d*) temperature, or electrodes 11, 12 (for sensing EMG, EGG, or impedance as well as providing stimulation), may be coupled to the controller 140 through A/D converters (with amplifiers)146*a*, 146*b*, 146*c*, 146*d*, 146*e* which convert a representative analog electrical signal into a digital signal. Suitable types of these sensors are generally known in the art and may be located within, on, or external to the housing or other portions of the of the stimulator, such as the attachment mechanism or elongate member.

Controller 140 is coupled to RAM 150 via an address bus 150*a* for addressing a location in RAM 150 and a bi-directional data bus 150*b* for delivering information to and from RAM 150. The RAM 150 includes event memory 148 that temporarily stores data recorded by sensors 147*a-d* or electrodes 11, 12 (or other electrode pairs described herein). RAM 150 also includes a programmable memory 149 which may be programmed, for example, by an external programmer 160. The data stored in the programmable memory may include specifications for the electrical stimulation operating modes, (e.g., waveform, type of stimulations: for pacing, inducing contraction or other type) and various procedure parameters, (e.g., when to deliver a drug or electrical stimulation). Such programming may be done in response to sensed information, or, it may be done automatically by an external controller or as desired by a treating physician, etc. Sensed data acquired from sensors 147*a-d* and electrodes 11, 12 or other electrode pairs described herein, provided to the controller 140 may be stored in event memory 148 in the RAM 150. The data stored in the event memory 148 may be sent intermittently as data bursts via the RF coil 145, as opposed to continuously, in order to save battery power.

The electrode 11, 12 outputs are used to provide electrical stimulation delivered through the stimulation driver 142 to the electrodes 11, 12. The stimulation modes and parameters can either be set using the external programmer 160, or they may be set in response to sensory feedback. The same electrode outputs are used to sense impedance through impedance circuit 153 and to sense electrical activity, which is delivered through A/D converter 146*e*. The electrodes 11, 12 are coupled through coupling capacitors 155*a* and 155*b* respectively, to the output of electrical stimulation driver 142 and the inputs of A/D converters 146*e*, 146*f*.

The impedance circuit 153 comprises a constant current source oscillator 154 that oscillates at a frequency of 50-100 kHz, and an A/D converter 146*f* coupled to the controller 140. The oscillator 154 provides a constant current source through electrodes 11, 12 resulting in a voltage across the electrodes 11, 12 that is representative of impedance, in view of the constant current. The voltage is provided through and is converted by A/D converter 146*f* to a digital signal representative of impedance. A/D converter 146*f* has a bandwidth that includes the 50 kHz frequency signal while filtering out the electrical stimulation signal that is delivered to the electrodes 11, 12 through electrical stimulation driver 142, and the EMG signal that is sensed by the electrodes 11, 12. Both of the outputs are filtered out by A/D converter 146*f*. A/D converter 146*e*, has a bandwidth that filters out the 50-100 kHz signal. Further, when a stimulation signal is being delivered, the controller 140 does not receive signals from A/D converters 146*e* and 146*f*. Thus the EMG and impedance sensing functions and the stimulation delivery functions are separated through the electronic circuitry 25, though using the same electrodes.

An additional circuit 158 (or a plurality of such circuits) may be provided in the electronic circuitry 25 that are comprised of the same components and are configured as A/D converter 146*e*, impedance circuit 153 and stimulation driver 142. Such circuit may provide stimulation, impedance, EMG or EGG sensing for an additional pair of electrodes.

The battery 144 has its output supplied to a DC-to-DC converter 144*a* to provide a higher voltage, which is utilized for electrical stimulation pulses. The DC-to-DC converter 144*a* is conventional and provides an output voltage of 15 to 20 volts. Further, the circuitry 25 may include one or more drivers 152*a*, 152*b*, 152*c*, 152*d* that drive various devices such as, for example, diagnostic or therapeutic electromechanical devices such as controlling valves, solenoids, etc. for drug deliver, etc. The controller 140 provides a signal to a driver 152*a-d* based on a preset program in ROM 143 and/or on sensed parameters stored in RAM 150. The circuit may also include a stepping driver 156 coupled to a stepper motor, for example, an precise drug delivery mechanism.

Figure 14:
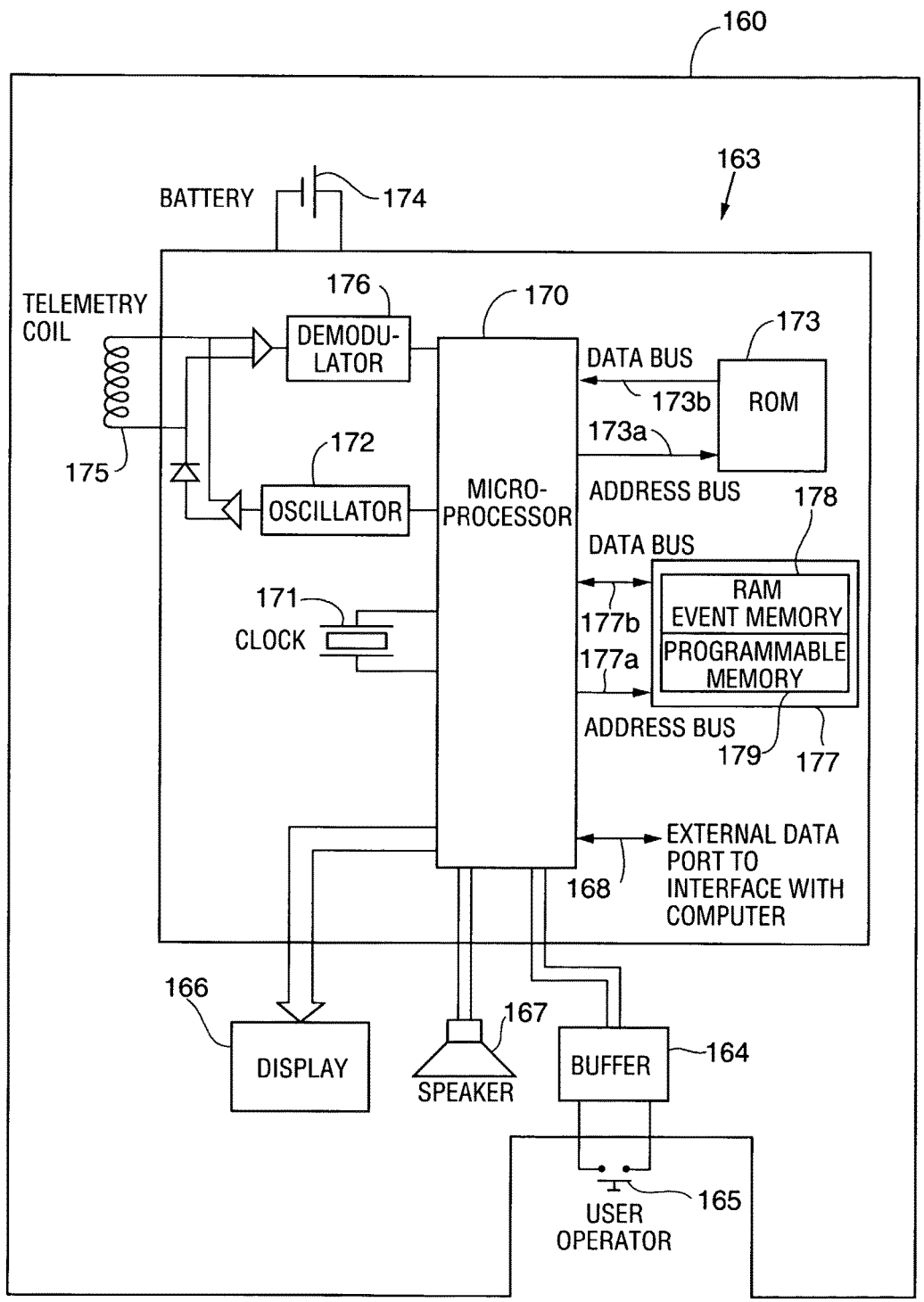
FIG. 14 illustrates a schematic diagram of the circuit of a programmer/recorder of the present invention.

FIG. 14 illustrates the electronic circuitry 163 for external programmer 160. The electronic circuitry 163 comprises: a microprocessor or controller 170 for controlling the operations of the electronic circuitry, an internal clock 171, and a power source 174 such as a battery device for powering the various components of the circuit 163. As such, the controller 170 and battery device 174 are coupled to each of the major components of the circuit as would be apparent to one of ordinary skill in the art. The controller 170 is coupled to a speaker 167 for that provides audible alerts and a display 166 such as a CRT to display data such as recorded data, sensed parameters, treatment parameters and status of the device (e.g. position or battery charge status). The controller 170 is coupled through a buffer 164 to external input device 165 that is used to provide program parameter input, e.g. from a user, for a user to request data displayed in a desired format through display 166 or speaker 167, or to turn the device on and off. The external programmer 160 is also provided with an external data port 168 to interface with a computer and provide a means for bi-directional communication of data or commands. The computer may provide programming or data to the controller/microprocessor 170. A user may also interface with the computer to provide treatment protocols or changes in protocols, etc. Also, a user may control the turning on and off of the stimulation program.

The controller 170 is coupled to ROM 173, which contains the program instructions for the controller 170 and any other permanently stored information that allows the microprocessor/controller to operate. The controller 170 addresses memory in ROM 173 through address bus 173*a* and the ROM 173 provides the stored program instructions to the controller 170 via data bus 173*b*. The controller 170 controls the RF coil 175, which communicates with stimulator electronic circuitry 25 (FIG. 13) through its RF coil 145. Processor 170 is coupled to an oscillator 172 that provides an RF signal, preferably having a characteristic frequency of 500 kHz or higher, to be emitted from the RF coil 175. The controller 170 controls the oscillator 172 and provides data to be modulated with the RF signal, for example, programming information, stimulation parameters, etc. The RF coil 175 also receives information transmitted via RF signal from RF coil 145 on the stimulator electronic circuitry 25 such as various sensed data, e.g., pressure, pH, impedance, electrical activity (EMG) etc. The received RF signal is passed through demodulator 176 and is transmitted to the controller 170. The data is delivered to the event memory 178 in RAM 177 by way of data bus 177*b* for temporary storage. The data may be retrieved from RAM 177 by addressing the storage location via the address bus 177*a*.

Event memory 178 temporarily stores data recorded by sensors 147*a*-147 and electrodes 11, 12 and delivered via telemetry to the external programmer 160, until the data is downloaded onto a computer using the external data port 168. The RAM 177 also includes a programmable memory 179 which may be programmed, for example, to specify operating modes such as waveform, frequency, etc. which programming is then telemetrically communicated to the stimulator electronic circuitry 25. The modes and parameters can either be set using an external programmer 160 or set in response to sensory feedback.

In an alternative embodiment, the device includes a housing, electrodes and minimal electronics and an electromagnetic coil. This device is powered by an external electromagnetic coil, which is placed on the patient's abdomen near the implanted device. The electrical stimulation parameters are controlled real-time by an external unit.

In an alternative embodiment, the device includes a housing, electrodes and minimal electronics and an electromagnetic coil. This device is powered by an external electromagnetic coil, which is placed on the patient's abdomen near the implanted device. The electrical stimulation parameters are controlled real-time by an external unit.

Instruments and Methods For Preparing the
Stomach Wall For Implants

Figure 16A:
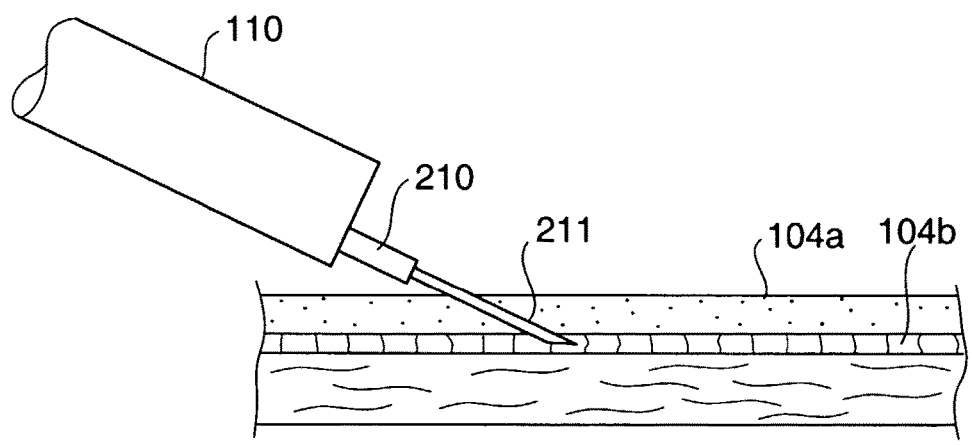
FIGS. 16A and 16B illustrate endoscopic instruments used to prepare a bleb in the submucosal layer of the stomach wall.
Figure 16B:
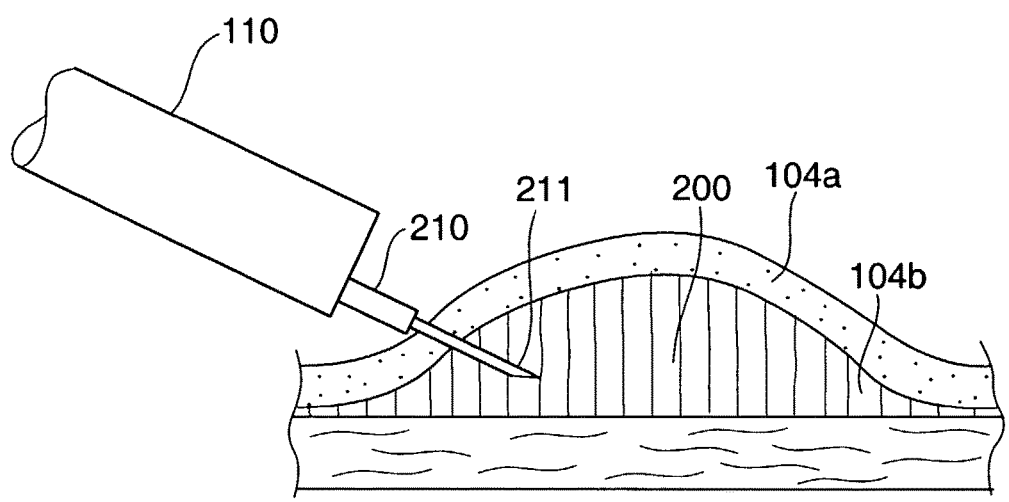

FIGS. 16A and 16B illustrate a first step in one embodiment of a method of implanting a gastric stimulator in the submucosal layer of a stomach and instruments used in the method. According to FIGS. 16A and 16B, a bleb 200 is formed in the submucosal layer 104b of the stomach wall 104. The bleb 200 is formed to prepare a space in the submucosal layer for receiving an implant. A hollow needle catheter 210 is extended through the channel 112 in the endoscope 110 located in a patient's stomach. The needle tip 211 of the catheter 210 is used to pierce the mucosal layer 104a so that the tip 211 is located in the submucosal layer 104b. A fluid is injected into the submucosal layer 104b to form the bleb 200 (or blister) (FIG. 16B). A number of different fluids may be used for this purpose, e.g., a saline solution, a viscous fluid such as sodium hyaluronate, or a chemical agent that cuts, breaks down, or dissolves a desired amount of submucosal connective tissue. Some chemical agents that may be suitable include KOH, acids and enzymes such as a peptase enzyme solution, proteases/colagenases, papain, bromelain, ficin, chymotrypsin and urokinase. When using a chemical agent, it may be desirable to flush or dilute the agent and/or evacuate the resulting loose material after introducing the agent into the submucosa.

According to an embodiment of the invention, once a bleb 200 is formed, the connective tissue within the submucosal layer 104b is dissected, cut, broken down, dissolved, or removed to form a pocket where the stimulator is to be placed. A number of alternative methods and instruments are described herein to prepare the stomach wall to implant a gastric stimulator.

Figure 17A:
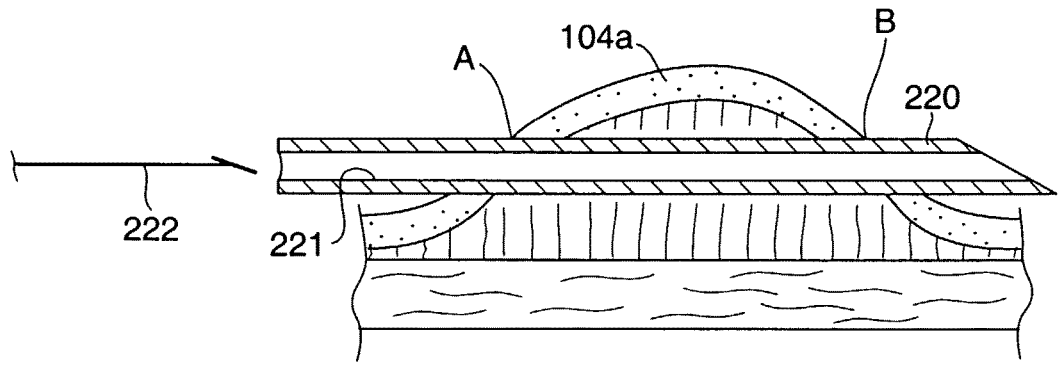
FIGS. 17A-17G are side partial cross sectional views of an embodiment of the invention in which a balloon is used to prepare a pocket in the submucosal layer for receiving a submucosal implant.
Figure 17B:
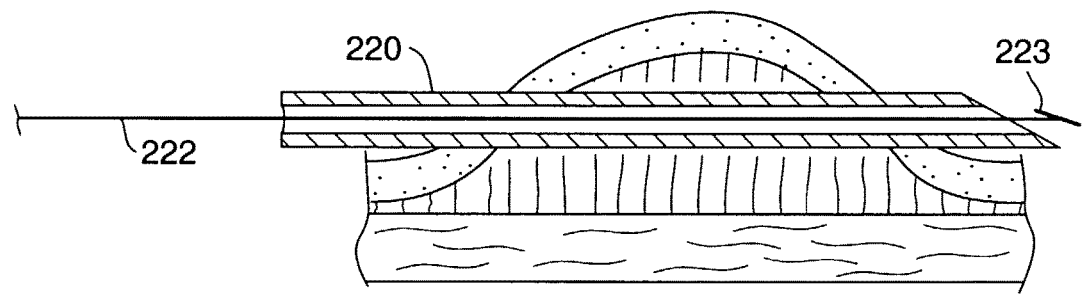
Figure 17C:
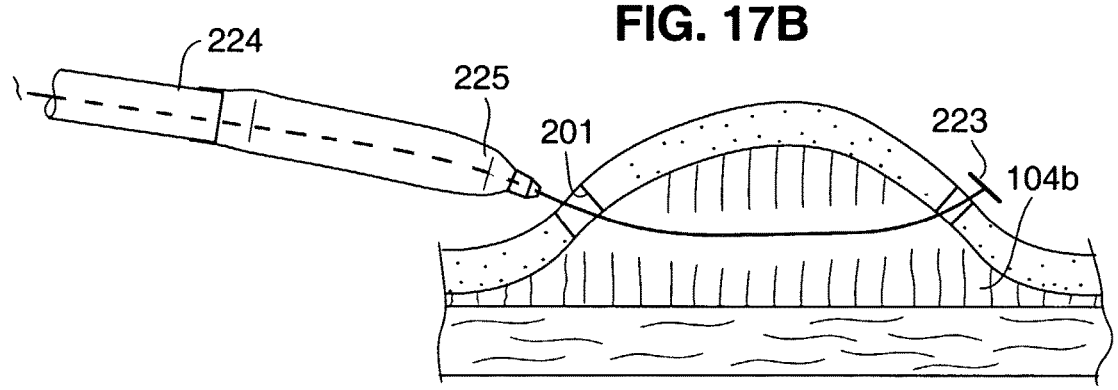
Figure 17D:
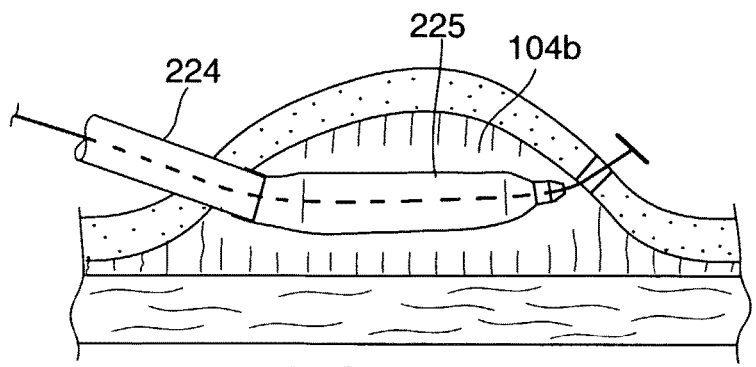
Figure 17E:
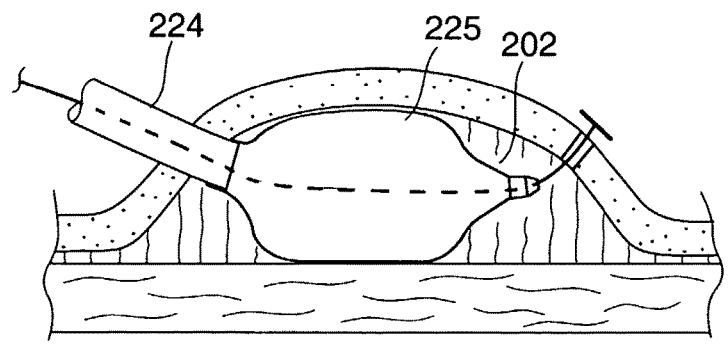
Figure 17F:
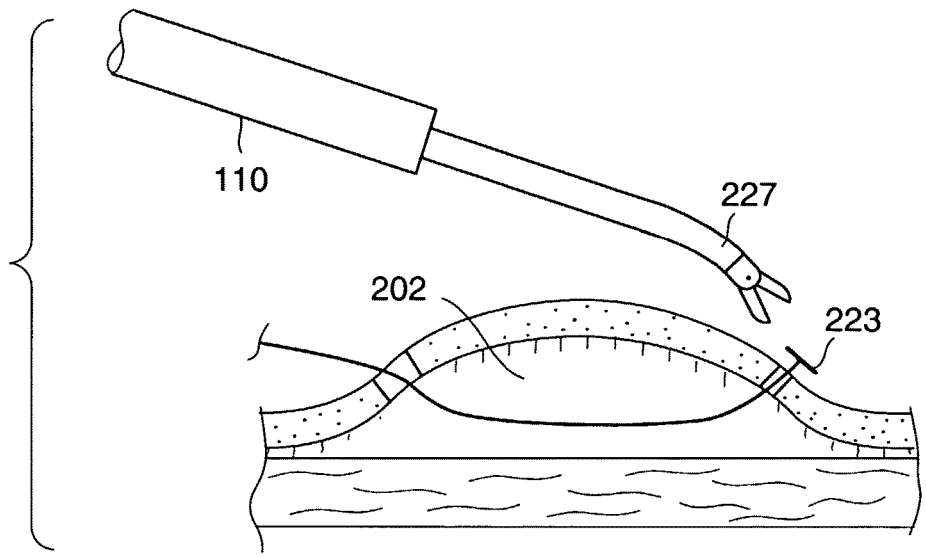
Figure 17G:
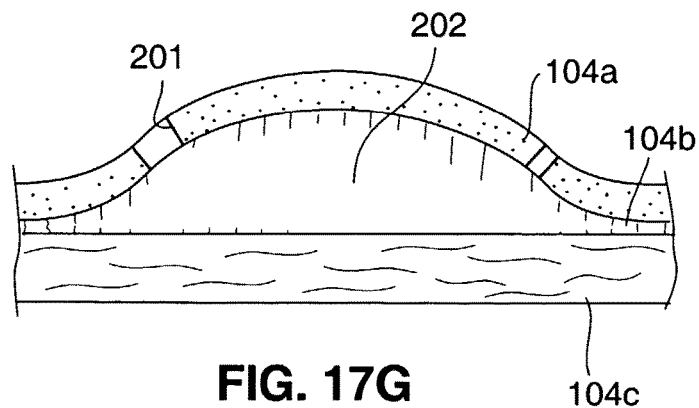
Figure 18A:
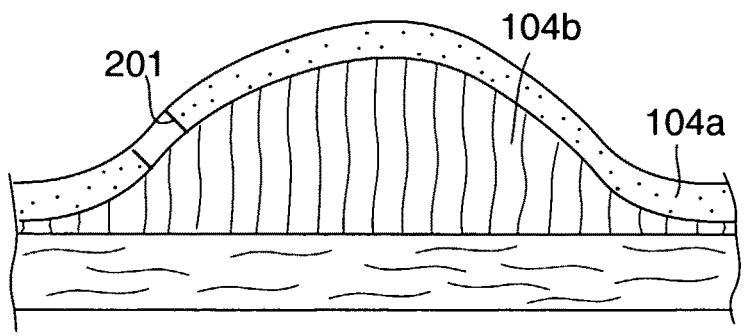
FIGS. 18A-18E are side partial cross sectional views of another embodiment of the invention in which a balloon is used to prepare a pocket in the submucosal layer for receiving a submucosal implant.
Figure 18B:
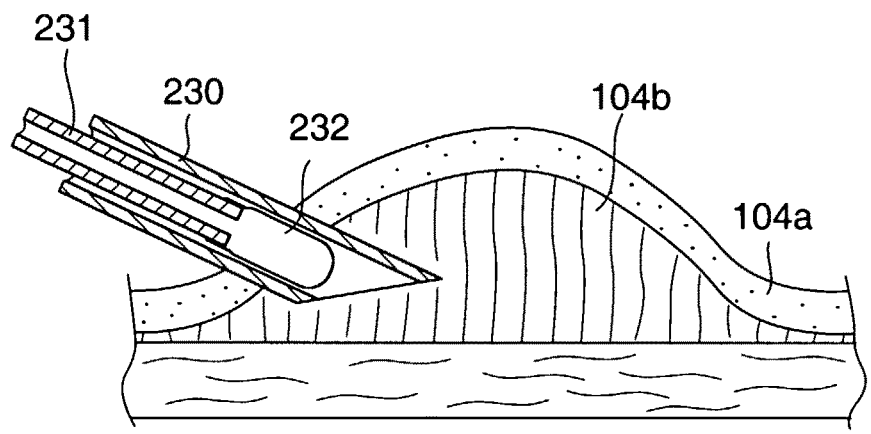
Figure 18C:
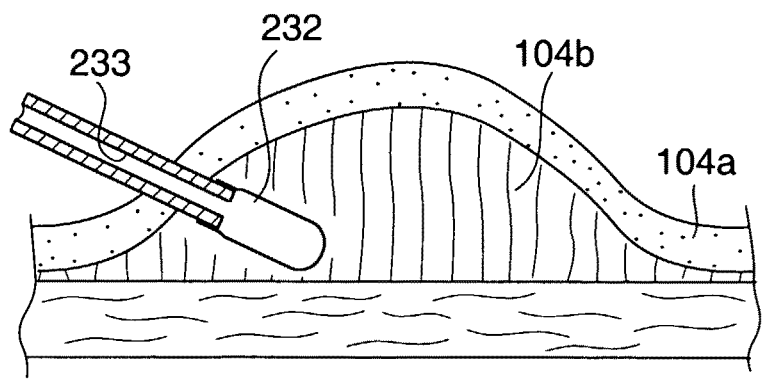
Figure 18D:
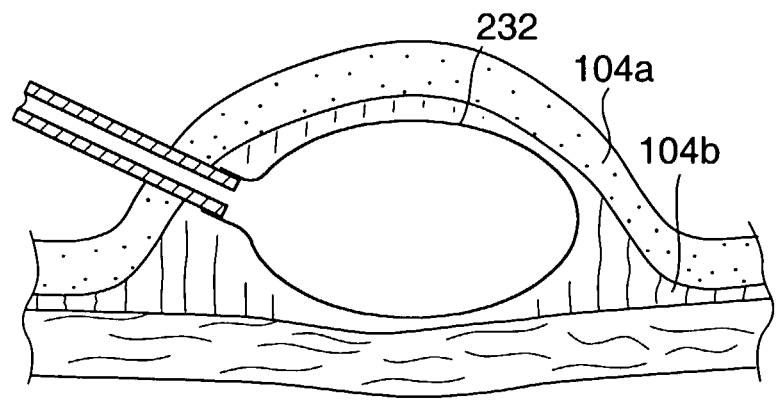
Figure 18E:
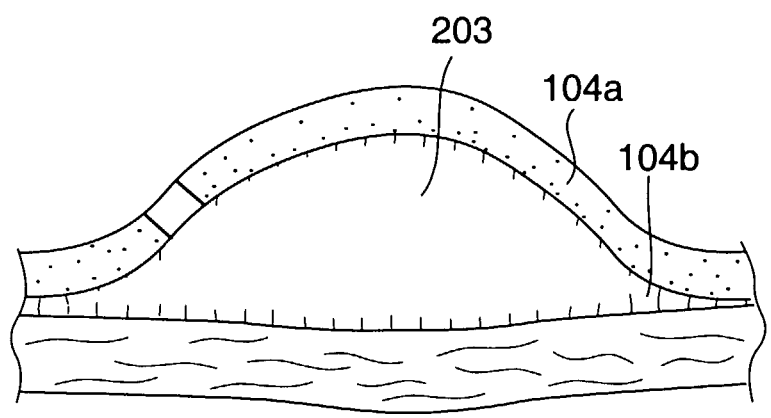

FIGS. 17A-G illustrate one embodiment in which a balloon with a guidewire is used to dissect connective submucosal tissue. According to this embodiment as illustrated in FIG. 17A, a hollow needle 220 having a lumen 221 is placed through the mucosal layer 104a at location A, into the bleb 200, advanced through the submucosal layer 104b, and out of the bleb 200 through the mucosal layer 104a at location B. As illustrated in FIG. 17B, a flexible guidewire 222 is placed through the hollow needle 220. The guidewire 222 includes a T-shaped end 223 so that when the needle 220 is withdrawn (FIG. 17C), the T-shaped end 223 remains outside the mucosal layer 104a, preventing the guidewire 222 from being withdrawn while the guidewire 222 extends back through the submucosal layer 104b and out through the endoscope 110. The guidewire 222 is then used to guide a balloon catheter 224 over the guidewire 222 so that the balloon 225 is placed within the bleb 200 in the submucosal layer 104b in an uninflated state (FIG. 17D). Inflation medium is delivered through an inflation lumen in the balloon catheter 224 to inflate the balloon 225 (FIG. 17E) whereby a pocket 202 is formed in the submucosal layer. The balloon 225 is then deflated and retracted. A cutting instrument such as a scissors 227 is introduced through the endoscope 110 and is used to cut off the T-shaped end 223 (FIG. 17F) so that the guidewire 222 can be pulled out, leaving a pocket 202 in the submucosal layer 104b. The balloon 225 may be either a compliant or non-compliant balloon that either expands elastically or expands to a predetermined volume.

Referring now to FIGS. 18A-E a second embodiment is illustrated in which a balloon is used to dissect the connective tissue in the submucosal layer 104b. A hollow endoscopic needle 230 containing a balloon tipped instrument 231 having a compliant balloon 232 on the distal end of the instrument 231, is placed at the opening 201 (formed in the mucosal wall 104a when the bleb 200 is formed (FIG. 14A)), and into the submucosal layer 104b (FIG. 14B). The endoscopic needle 230 is retracted leaving the balloon 232 at the opening 201 within the submucosa 104b (FIG. 14C). The balloon 232 is inflated by introducing an inflation medium through the inflation lumen 233 in the instrument 231. (FIG. 14D). The opening 201 is relatively small so as to prevent the balloon 232 from exiting the submucosa 104b when the balloon 232 is inflated. As it is inflated, the balloon 232 expands distally as well as radially to dissect the submucosal tissue. The balloon 232 in this embodiment made of a compliant or non-compliant material. The balloon 232 is then deflated and withdrawn leaving a pocket 203 in the submucosa 104b. (FIG. 14E).

Figure 19A:
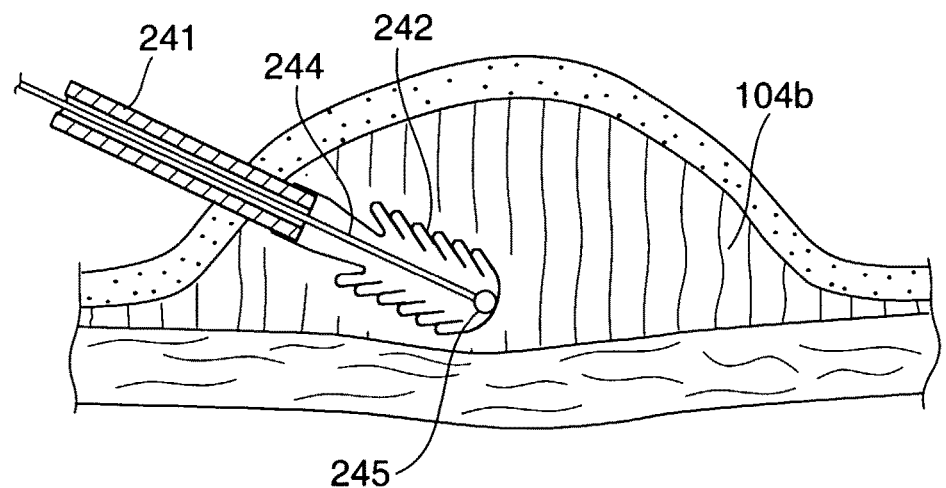
FIGS. 19A and 19B are side partial cross sectional views of another embodiment of the invention in which a balloon is used to prepare a pocket in the submucosal layer for receiving a submucosal implant.
Figure 19B:
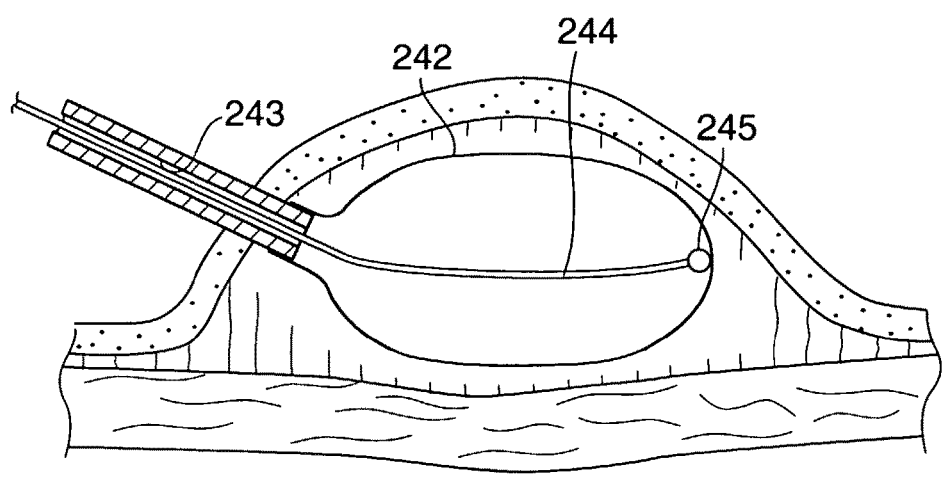

FIG. 19 illustrates an alternative to the embodiment of FIGS. 18A-E in which the balloon tipped instrument 241 has a folded balloon 242 on the distal end of the instrument 241. The balloon 242 is placed into the submucosal layer 104b (FIG. 19A). An atraumatic tip 245 of a sliding rod 244 is attached to the inside of the distal end of the balloon 242. The rod 244 extends through the instrument 241 and may be manipulated externally of the endoscope through which it is inserted. The rod 244 may be distally advanced to aid in dissecting the submucosal connective tissue, as the balloon 242 is inflated when an inflation medium is introduced through the inflation lumen 243 in the instrument 241. (FIG. 19B). The rod 244 may also orient the expansion of the balloon 242 in a desired direction.

Figure 20A:
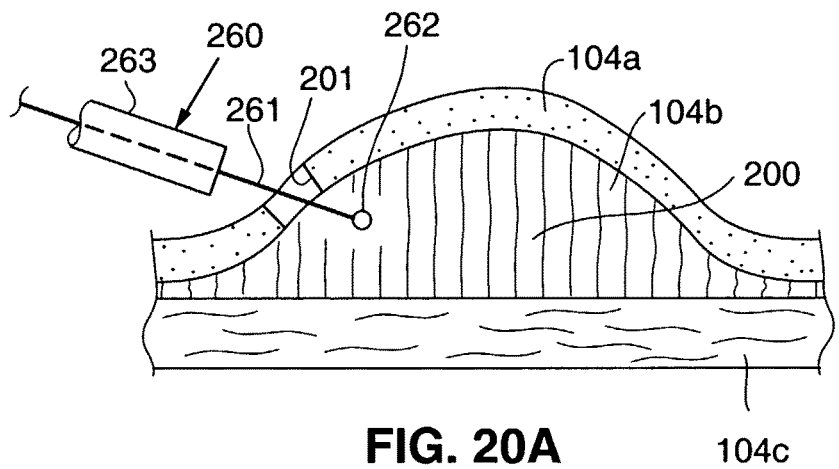
FIGS. 20A-20H are side partial cross sectional views of another embodiment of the invention in which a balloon is used to prepare a pocket in the submucosal layer for receiving a submucosal implant, wherein the method and device include using a guidewire device and method for locating a guidewire within the submucosal layer of the stomach wall.
Figure 20B:
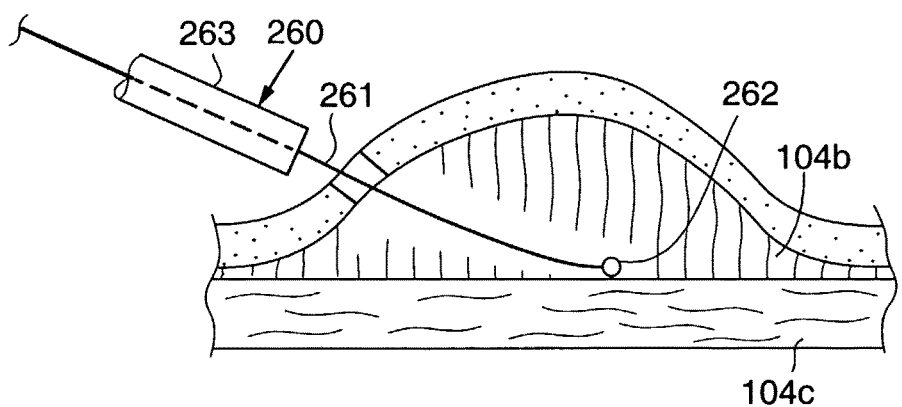
Figure 20C:
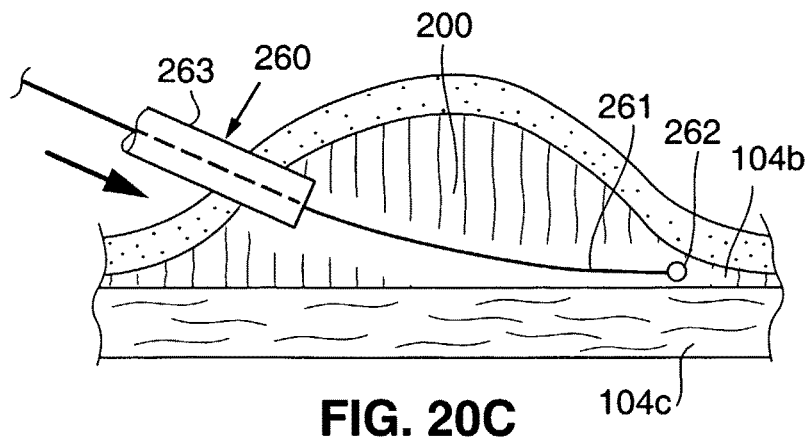
Figure 20D:
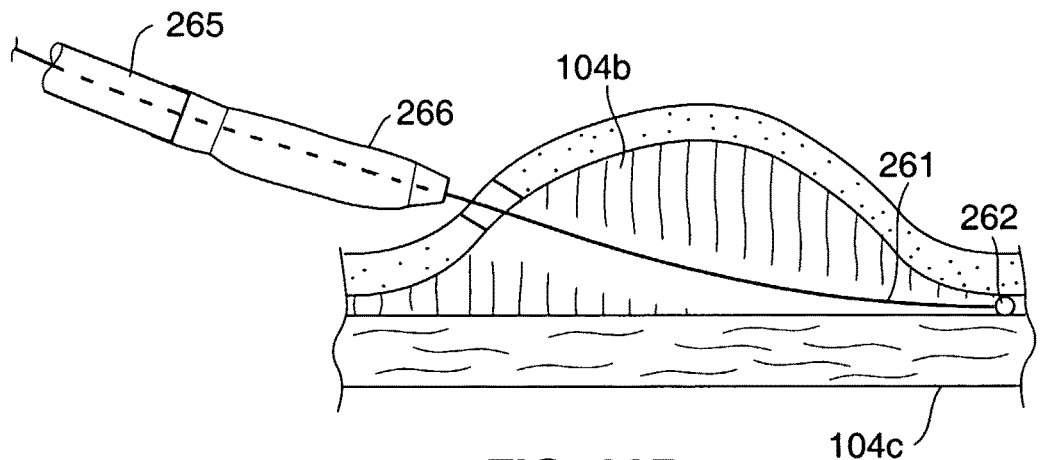
Figure 20E:
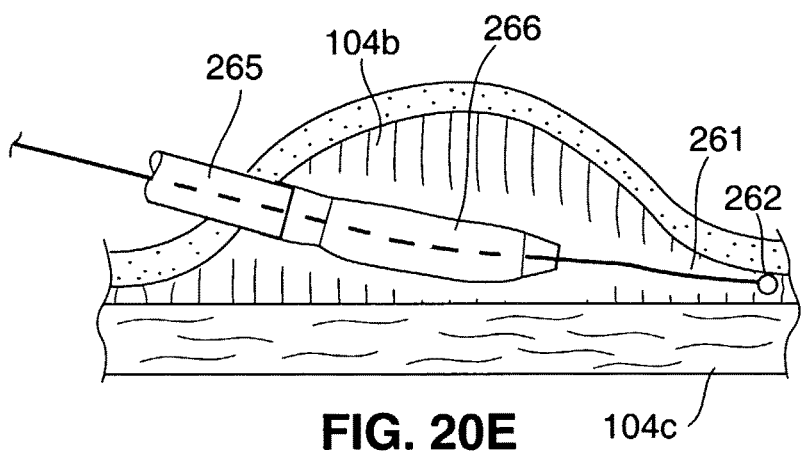
Figure 20F:
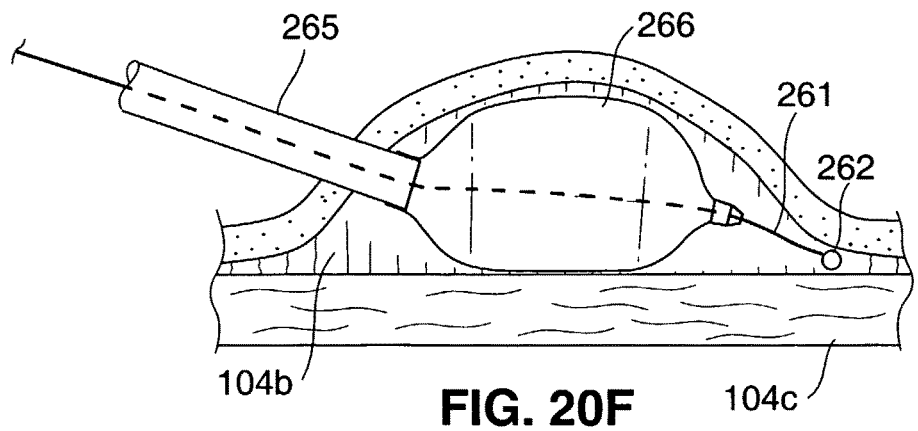
Figure 20G:
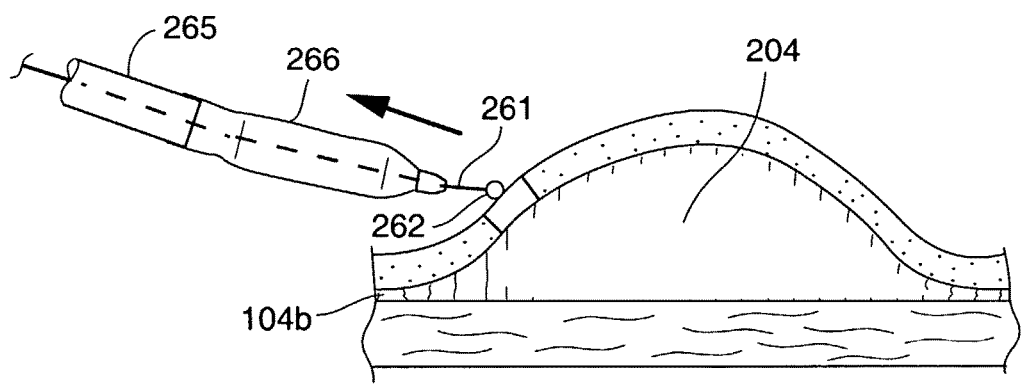

FIGS. 20A-H illustrate a self guiding guidewire device in use with a balloon dissection tool. The self-guiding instrument 260 comprises a flexible guidewire 261 with a ball tip 262 at its distal end and a stiff hollow tubing 263 such as a hypotube through which the guidewire 261 extends. The flexible guidewire 261 may slide in and out of the tubing 263 to provide desired degree of flexibility, stiffness, or buckle or kink resistance of the unsupported length of the guidewire at the distal end of the instrument 260. The degree of flexibility or buckle resistance may be varied at different times during the placement of the guidewire 261 inside the submucosal layer 104b. As illustrated in FIG. 20A, the instrument 260 is placed near the opening 201 formed in the mucosal layer 104a, and the guidewire tip 262 extends slightly out of the tubing 263 into the submucosal layer 104b of the bleb 200. The tip 262 is preferably rounded to some extent to prevent puncturing of the muscle layer 104c or the mucosal layer 104a while having a sufficiently small surface area to allow it to relatively easily advance through the submucosal layer 104b. The guidewire 261 is sufficiently flexible to prevent puncturing of the muscle layer 104c or the mucosal layer 104a while being sufficiently stiff to prevent buckling as the guidewire 261 is inserted. As illustrated in FIG. 20B, the guidewire 261 becomes more deflectable at the distal end of the instrument 260 as it is advanced distally out of the tubing into the submucosal layer. The atraumatic ball tip 262 in combination with a flexible guidewire 261 prevent puncture of the muscle layer. At some point in the procedure, the guidewire 261 may be too flexible and may buckle, kink or may fail to further advance into the submucosal layer 104*b*. As illustrated in FIG. 20C, the length of guidewire 261 extending out of the tubing 263 is shortened by advancing the tubing 263 distally over the guidewire (and into the bleb 200) so that the distal end is less deflectable and/or prone to buckling and may be advanced further. These steps may be repeated, varying the deflectability of the distal end of the instrument 260 until the guidewire 261 is in a desired location. The guidewire may also be designed to optimize the flexing and anti-buckling characteristics so that it is suitable for placement within a submucosal layer with or without a hypotube. In one embodiment, various parameters of the wire are selected so that the submucosal insertion into over 5 to 10 cm of the submucosa may be achieved without perforation of the mucosa or muscle layers. In one example of a suitable embodiment, a stainless steel wire is used having an outer diameter of 0.020 inches with a wire bending stiffness of 654 $Nmm^2$. and a ball size of 0.040 inches. Once the guidewire 261 is in place in the submucosa 104*b*, the tubing 263 is retracted and a balloon catheter 265 is advanced over the guidewire 261 (FIG. 20D) and into the submucosa 104*b* (FIG. 20E). The balloon catheter 265 has a balloon 266 at its distal end, a lumen 267 (FIG. 20H) extending through it for slidably receiving the guidewire 261, and an inflation lumen 268 for delivering an inflation medium to the balloon 266. As illustrated in FIG. 20F, the balloon 266 is inflated after being positioned in the bleb 200, to dissect the submucosal connective tissue. The guidewire 261 and balloon catheter 265 are withdrawn, leaving a pocket 204 formed in the submucosal tissue, for receiving a gastric stimulator. (FIG. 20G). Although the balloon 266 is illustrated as an elastic balloon, a non-compliant balloon may be used as well.

Figure 20H:
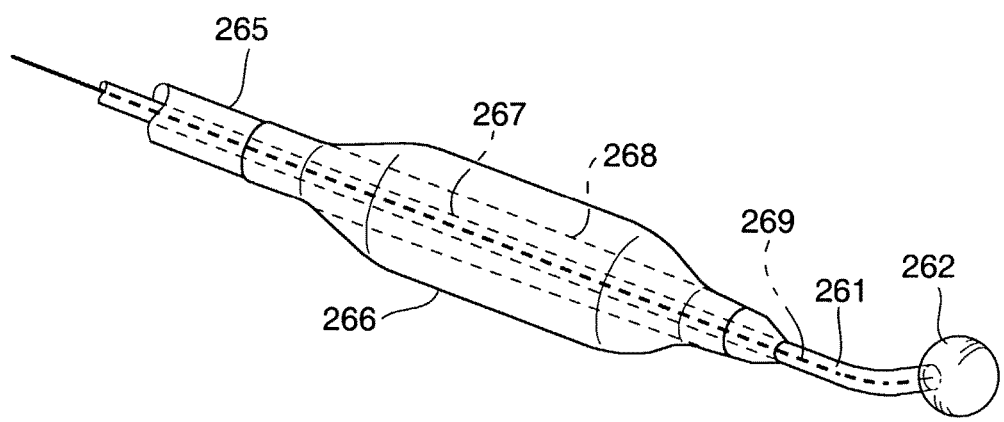

As illustrated in FIG. 20H, an additional feature of the guidewire 261 provides a optic fiber 269 extending through the wire and terminating at the ball tip 262 which is made of a clear plastic material. Light may be carried down the optic fiber 269 to illuminate the ball tip 262. This provides additional information on the location of the tip 262 in the submucosal layer 104*b*, as the tip 262 is being insert into the stomach wall. The light will be visible when observing the procedure through an endoscope as the guidewire is inserted into the submucosal layer 104*b*. The ball tip may also be tapered. The guidewire may also be formed of a pre-tensioned coil that deflects when a given force is applied to the tip.

Figure 21A:
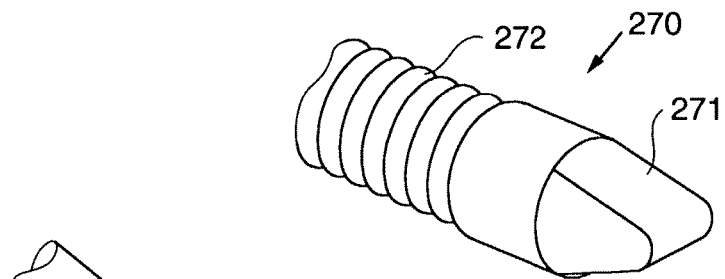
FIG. 21A is a perspective view of a distal end of a blunt dissection device used to prepare a cavity in the submucosal layer of the stomach wall.
Figure 21B:
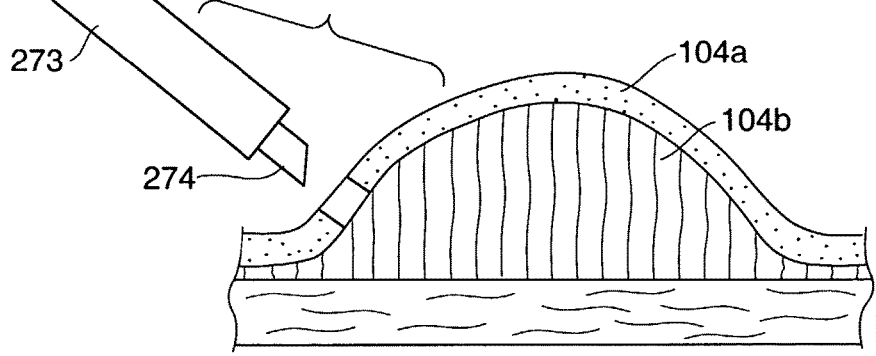
FIG. 21B is a side partial cross sectional view of a cutting instrument preparing an opening in the mucosal layer of the stomach wall.
Figure 21C:
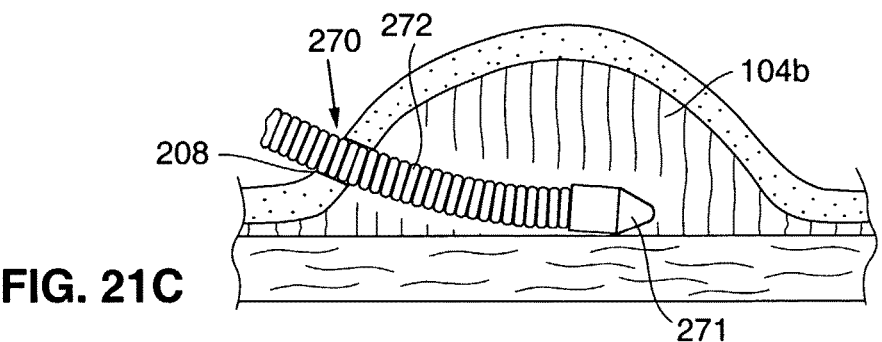
FIG. 21C is a side partial cross sectional view of the blunt dissector of FIG. 21A in use in preparing a cavity in the submucosal layer of the stomach wall.

FIGS. 21A-21C illustrate a mechanical blunt dissector and method of dissecting the submucosal layer 104*b*. The blunt dissector instrument 270 comprises a tapered, wedge-like, blunt distal end 271 on an elongate flexible member 272, preferably having a flexible coil outer tube to provide sufficient axial stiffness in combination with flexibility. As illustrated in FIG. 21B, an RF needle or scalpel 273 have an RF cutting tip 274 is used to create an opening 208 through the mucosa 104*a* into the submucosa 104*b*. As illustrated in FIG. 21C, the blunt distal end 271 is placed within the opening 208 into the submucosal layer 104*b* and is used to mechanically dissect the tissue.

Figure 22:
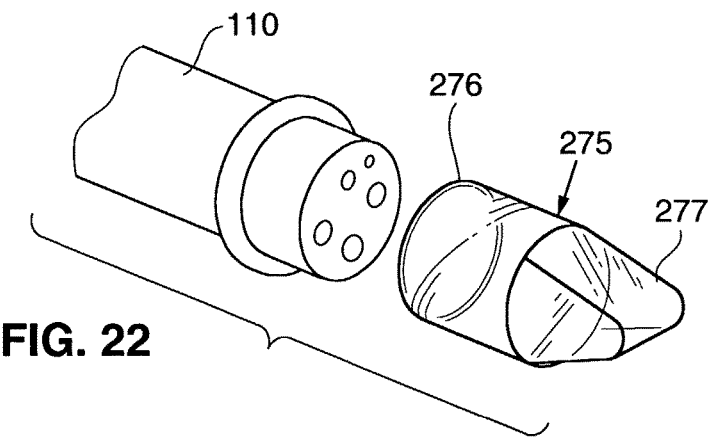
FIG. 22 illustrates an exploded perspective view of the distal end of a modular blunt dissector/endoscope.

FIG. 22 illustrates a blunt dissector connector 275 comprising a cap 276 to be placed on the end of an endoscope 110 and having a wedge-like, tapered, blunt distal end 277. The blunt distal end 277 is made of a clear material that allows visualization through an endoscope as the blunt dissector is being placed through the opening 201 and as it is used to dissect the submucosal tissue 104*b*.

Figure 23A:
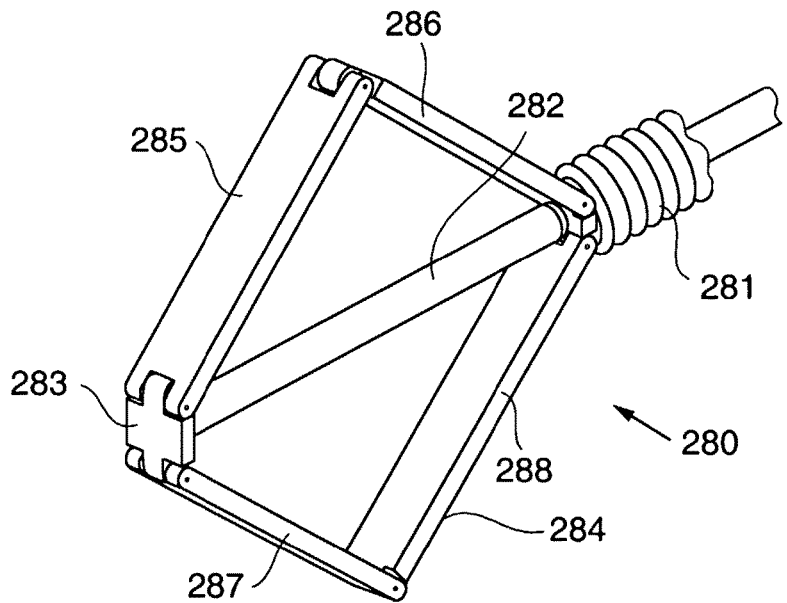
FIG. 23A is a perspective view of a distal end of an endoscopic dissecting instrument in accordance with an embodiment of the invention.
Figure 23B:
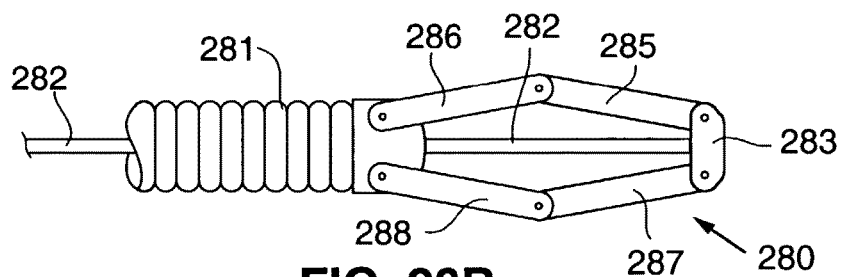
FIG. 23B is a side view of the dissecting instrument of FIG. 23A in a closed position.
Figure 23C:
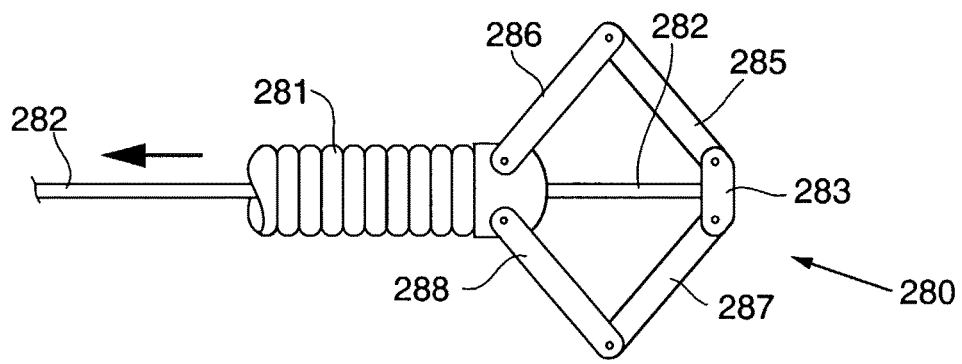
FIG. 23C is a side view of the dissecting instrument of FIG. 23A in an open position.

FIGS. 23A-23C illustrate an alternative embodiment of a mechanical dissecting instrument that may be used to dissect the submucosal tissue. The dissecting instrument 280 comprises an elongate member 281 formed of a flexible coil and having a slidable push rod 282 slidable within a lumen extending through the length of the elongate member 281 and coupled to a distal linking member 283 of a distal end effector 284. The distal end effector 284 of the instrument 280 comprises four linkages 285, 286, 287, 288 that are hingingly coupled to one another with two links 285,286 above the slidable push rod 282 and two links 287, 288 below the slidable push rod 282. The links 286 and 288 are hingingly coupled to the distal end of the elongate member 281 and are hingingly coupled to links 285, 287 respectively which are hingingly coupled to the distal linking member 283. In a closed position as illustrate in FIG. 23B, the push rod 282 extends distally so that the links 285-288 are relatively parallel and the profile of the end effector 284 is relatively narrow. In an open position as illustrated in FIG. 23C, the push rod 282 is retracted, to shorten and widen the end effector 284 as the linkages hinge with respect to one another. When placed in the bleb, as the end effector 284 opens, it dissects adjacent submucosal tissue.

Figure 24A:
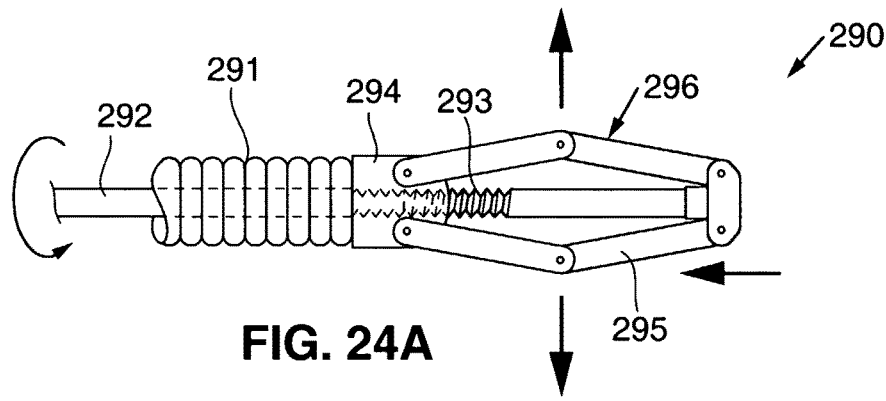
FIG. 24A is a side view of a dissecting instrument in accordance with another embodiment in a closed position.
Figure 24B:
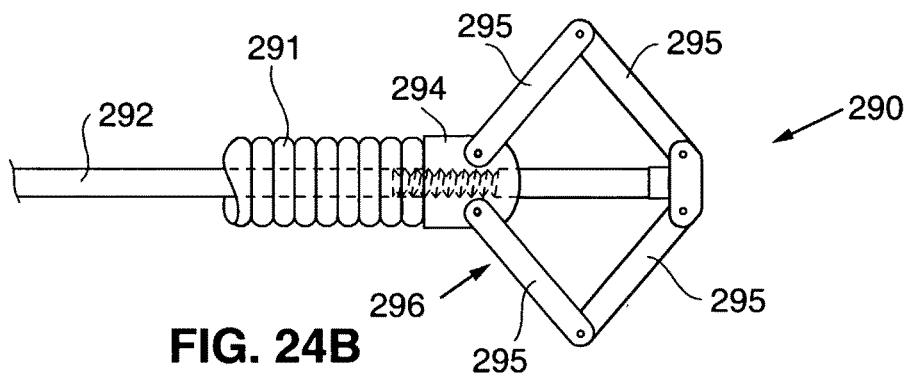
FIG. 24B is a side view of the dissecting instrument of FIG. 24A in an open position.

FIGS. 24A and 24B illustrate a blunt dissector 290 similar to the blunt dissector of FIGS. 23A-C except that rather than using a push rod, a screw type rod 292 is used where a threaded screw 293 is formed in the screw rod 292 and the distal end 294 of the elongate member 291 is threaded to receive the threaded screw 293. The end effector 296 is shown in a narrow closed position in FIG. 24A. The rod 292 is retracted by rotating the rod 292 and the screw 293 and thus shortening the end effector 296 so that the linkages 295 rotate to an open position.

Figure 25A:
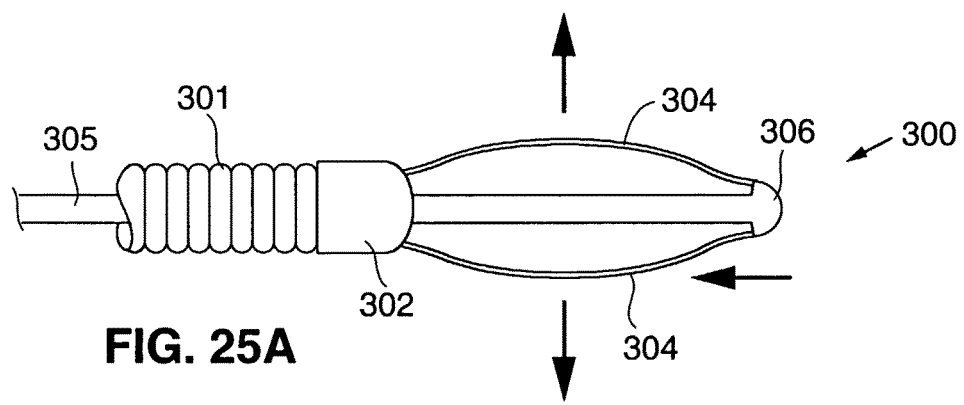
FIG. 25A is a side view of a dissecting instrument in accordance with another embodiment in a closed position.
Figure 25B:
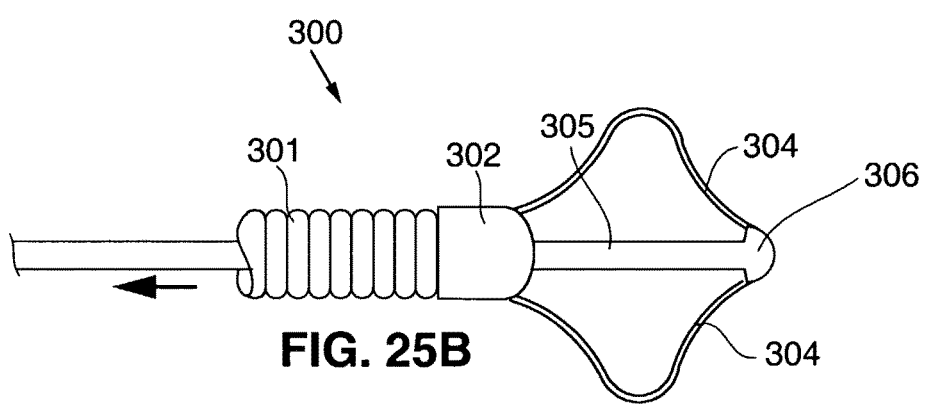
FIG. 25B is a side view of the dissecting instrument of FIG. 25A in an open position.

FIGS. 25A and 25B illustrate another blunt dissector 300 comprising an elongate member 301 formed of a flexible coil and having a slidable push rod 305 slidable within a lumen extending through the length of the elongate member 301 and the push rod 305 having a distal end 306 extending distally through an opening in the distal end 302 of the elongate member 301. Flexible expanding arms 304 are coupled to the distal end 302 of the elongate member and to the distal end 306 of the push rod 305. As illustrated in FIG. 25A, the push rod 305 is extended so that the flexible arms 304 are substantially parallel to provide a narrow device profile. As illustrated in FIG. 25B, the push rod 305 is retracted so that the flexible expanding arms 304 bend so that they can dissect submucosal tissue when located in the bleb 200 to form a pocket in the submucosal layer. In this embodiment, the flexible arms are preferably constructed of an elastic or superelastic material, such as, a Nickel Titanium alloy.

Figure 26A:
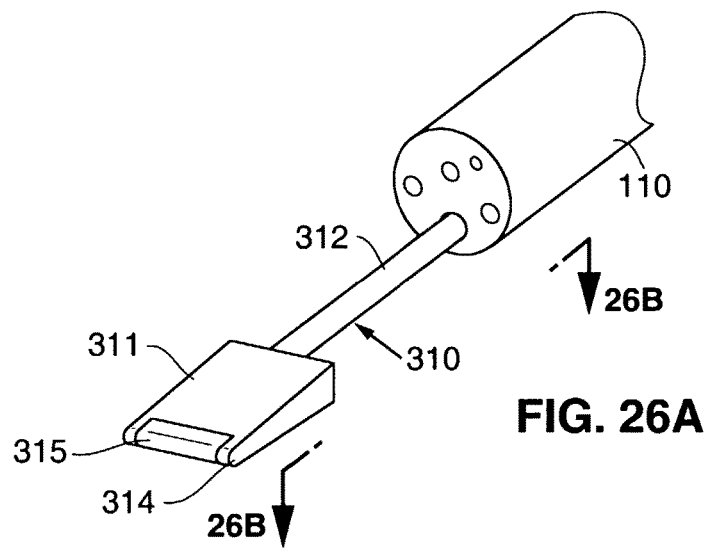
FIG. 26A is a perspective view of an electrosurgical dissecting instrument in accordance with an embodiment of the invention.
Figure 26B:
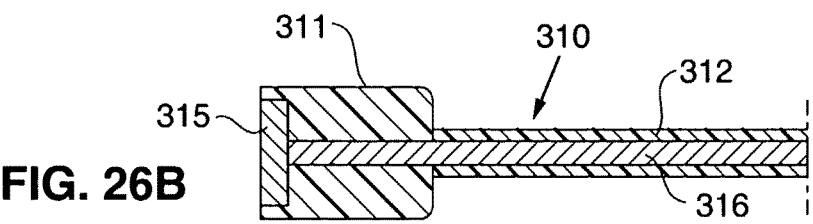
FIG. 26B is a top cross-sectional view of the instrument of FIG. 26A along the line 26B-26B.

FIGS. 26A-26B illustrate an electrosurgical blunt dissector for use in dissecting the submucosal layer 104*b*. The blunt dissector instrument 310 comprises a tapered, wedge-like, blunt distal end 311 on an elongate flexible member 312. The distal tip 314 of the end 311 comprises an electrode 315 that is coupled to a conducting wire 316 extending through the elongate flexible member 312 and coupled to an RF energy source outside the patient's body. The wedge separates the mucosal layer 104*a* and the muscle layer 104*c* and prevents perforation of either layer while the electrode 315 cuts the submucosal connective tissue. In this embodiment, a monopolar device is illustrated and a return electrode is placed on the patient's body. Bipolar or multipolar electrodes may be used as well. As an alternative, other energy sources may be used to break down the submucosal tissue as well. For example, a laser device or an ultrasonic device may be used as well.

Figure 27A:
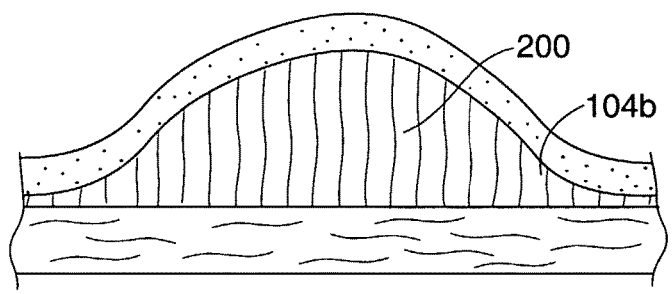
FIGS. 27A-27E are side partial cross sectional views of a knife and the dissector of FIGS. 26A-B in use in preparing a pocket in the submucosal layer of the stomach wall.
Figure 27B:
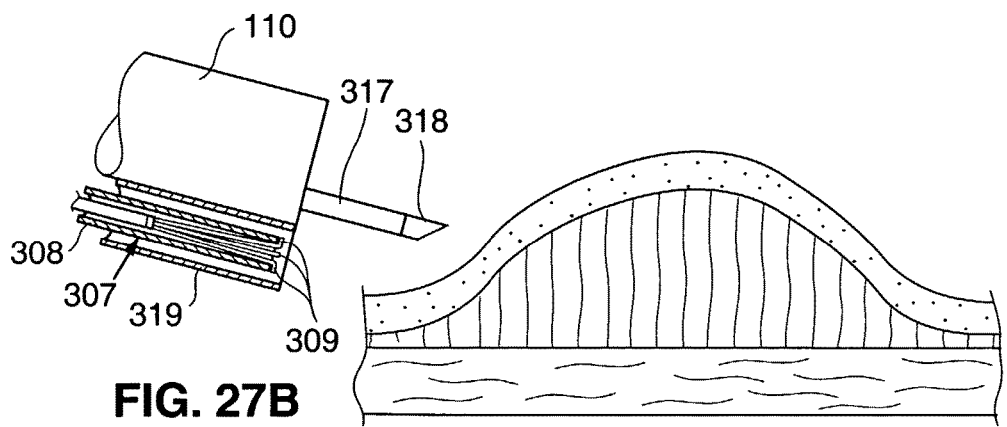
Figure 27C:
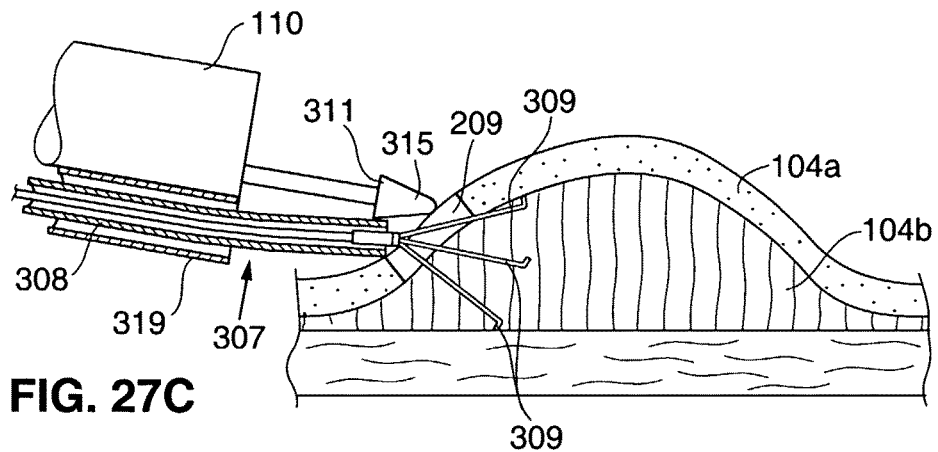
Figure 27D:
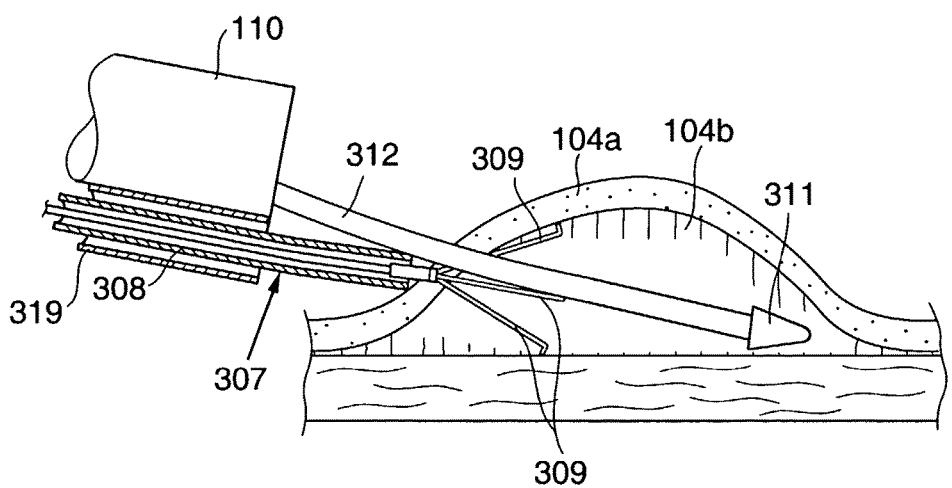
Figure 27E:
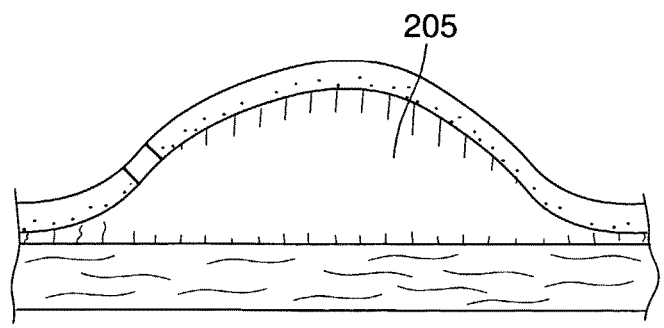

The use of the electrosurgical dissector of FIGS. 26A-26B is illustrated in FIGS. 27A-27E. After a bleb 200 is formed (FIG. 27A) a knife 317 having a sharp tip 318 is placed through the endoscope against the mucosal layer 104a to cut an opening 209 in the mucosal layer to access the submucosa. (FIG. 27B). Alternatively, the tip 318 may be an electrosurgical knife used to cut an opening in the mucosa. (Also, electrosurgical energy of the blunt dissector 310 may be used to cut through the mucosa 104a to enter into the submucosal layer 104b.) A multi-prong retractor 307 is introduced through an auxiliary guide 319 attached to the outside of the endoscope 110. The retractor 307 comprises a retractable sheath 308 and three prongs 309 on the distal end of the retractor 307. As illustrated in FIG. 27B, the prongs 309 are held in a closed position by the sheath 308. The sheath 308 is placed at the opening 209 in the mucosa, and the sheath 308 is retracted, allowing the prongs 309 to spring open as illustrated in FIG. 27C. The retractor 307 assists in providing access into the bleb through the opening 209, and securing and stabilizing the tissue while preparing the opening and/or inserting the implant. The blunt dissector is then placed at the opening 209 an into the submucosa 104b (FIG. 27C). Within the submucosal layer 104b, the electrosurgical energy may be supplied to the electrode 315 to assist in dissecting the tissue as needed (FIG. 27D). The wedge shape of the distal end 311 helps maintain the tool's position within and through submucosal layer 104b. The wedge shape of the distal end 311 may also assist in mechanically dissecting without the application of electrosurgical energy to provide a pocket 205 for receiving the gastric stimulator (FIG. 27E).

Tissue Stabilization Devices and Instruments for Implanting the Stimulator

Figure 28A:
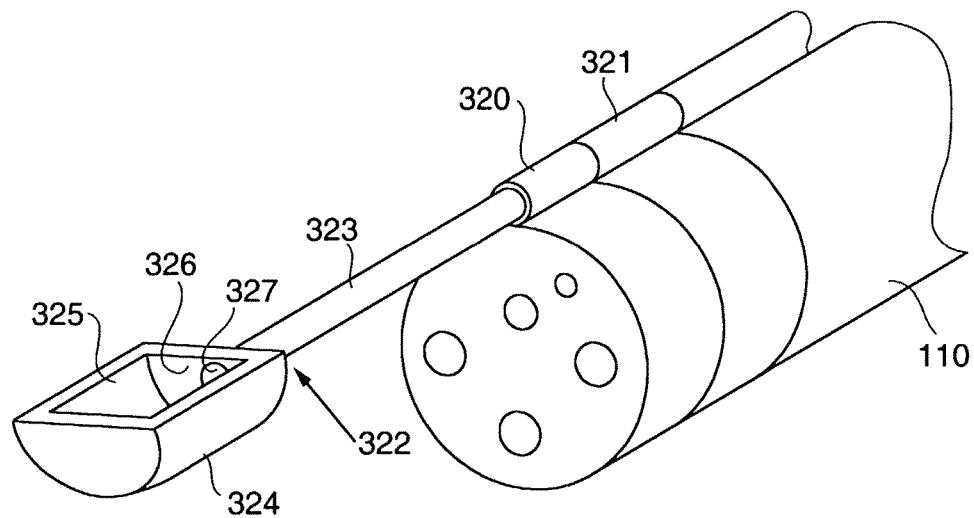
FIG. 28A is a perspective view of the distal end of an endoscope and stabilization device of the invention.
Figure 28B:
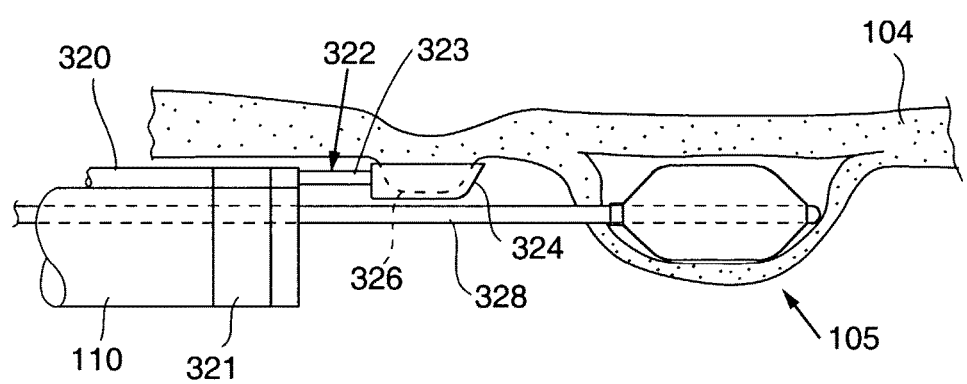
FIG. 28B is a side partial cross sectional view of the endoscope and stabilization device of FIG. 28A in use in preparing a pocket in the stomach wall.

Referring to FIGS. 28A and 28B, a tissue stabilization device is illustrated in which the tissue is stabilized with respect to the instrument. A sheath 320 extends along the length of the endoscope 110 and is attached to the outer circumference of the endoscope 110 with a band or tape 321. A suction instrument 322 comprises an elongate member 323 extending through the sheath 320. The elongate member 323 has a suction device 324 on its distal end, extending distally out of the sheath 320. The suction device 324 comprises a window 325 opening into a vacuum chamber 326. The elongate member 323 comprises a lumen extending from a proximal end, through the elongate member 323, and ending in an opening 327 into the vacuum chamber 326. The suction instrument 322 can slide in either direction within the lumen of the sheath 320 and may be locked into position by a locking mechanism, preferably on the proximal end. The lumen extending through the elongate member 323 is coupled to a vacuum source for applying a vacuum pressure to the suction device 324 through the elongate member 323.

The suction instrument 322 is illustrated in use in FIG. 28B. The suction device 324 is located near an implant site 105, e.g. near a bleb formed in the stomach wall 104, and is oriented with the window 325 facing the stomach wall. The window 325 is placed against the stomach wall and a vacuum is applied through the elongate member 323 into the vacuum chamber 326 so that the suction instrument 322 is engaged with the stomach wall. The stomach wall 104 is thereby stabilized relative to the endoscope 110 and a balloon of a balloon catheter 328 such as one of those described in more detail herein, is placed within the bleb and expanded to form a pocket within the submucosal layer.

Figure 29:
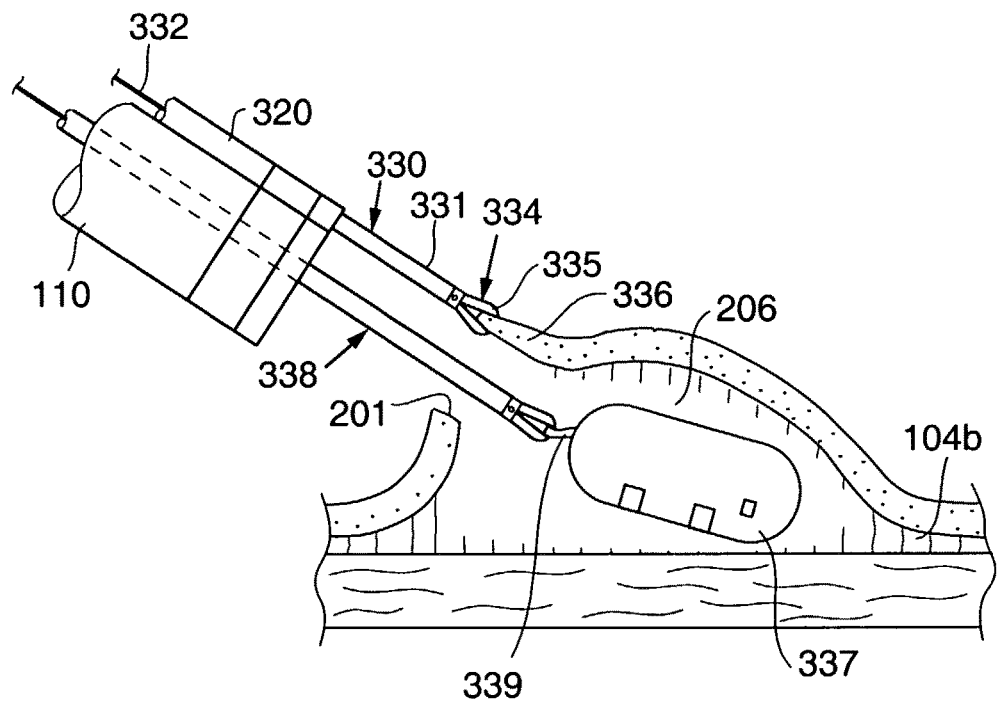
FIG. 29 illustrates a side partial cross-sectional view of a distal end of an alternative embodiment of an endoscope stabilization device and delivery device in use in placing a stimulator of the present invention within the submucosa of the stomach wall.

FIG. 29 illustrates an alternative stabilizing instrument 330 that is placed through the sheath 320 described with reference to FIGS. 28A and 28B. The stabilizing instrument 330 comprises an elongate member 331 having an actuating wire 332 extending from an end effector 334 on the distal end 333 of the instrument 330 to a proximal manipulating end (not shown) outside of the endoscope 110. The end effector 334 comprises a grasping pincer 335, which is illustrated grasping a mucosal flap 336 forming a portion of the opening 201 in the mucosal wall 104a into the submucosal layer 104b. The grasping pincer 335 holds the stomach wall for stabilization and also holds the mucosal flap 336 to access the pocket 206 formed in the submucosal layer 104b. The grasping pincer 335 is actuated by manipulating wire 332. As illustrated in FIG. 33, an implant 337 is guided into the pocket 206 with an endoscopic grasping tool 338 that grasps a knob 339 on the implant 337 to manipulate the implant 337 into place. Once in place, the grasping pincer 335 releases the mucosal flap 336 and the grasping tool 338 releases the knob 339 of the implant 337.

Figure 30:
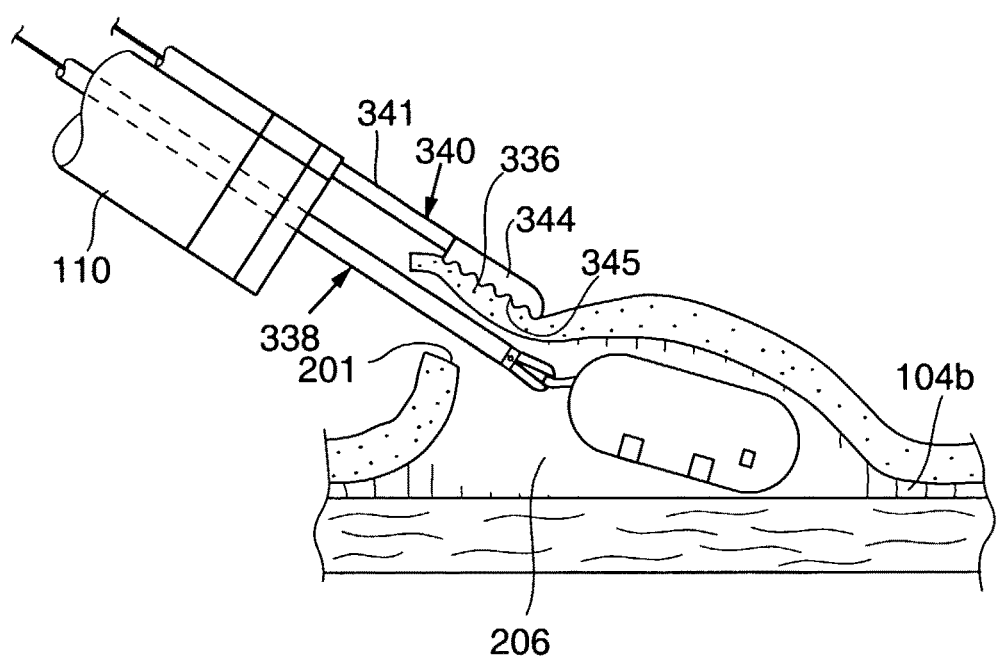
FIG. 30 illustrates a side partial cross-sectional view of the distal end of another embodiment of an endoscope, and stabilization and delivery devices in use in placing a stimulator of the present invention within the submucosa of the stomach wall.

Referring to FIG. 30, an alternative to the stabilizing instrument 330 shown in FIG. 33, is illustrated. The stabilizing instrument 340 of FIG. 30 comprises an elongate member 341 having an end effector 344 comprising a vacuum pad 345. A lumen extends through the elongate member 341 from the end effector 344 to the proximal end (not shown), which is coupled to a vacuum source. The vacuum pad 345 of the end effector 344 comprises a plurality of openings so that the vacuum applied through the pad 345 is relatively evenly distributed. The vacuum pad 345 is placed near the mucosal flap 336 and a vacuum is applied. The stabilizing instrument 340 holds the stomach wall for stabilization and also holds the mucosal flap 336 to further open the opening 201 and access the pocket 206 formed in the submucosal layer 104b. The endoscopic grasping tool 338 guides the implant 337 into the pocket 206 as described above with reference to FIG. 33, and once in place the vacuum pressure is released and the instruments 340 and 338 are withdrawn.

FIGS. 31A-31F illustrate an alternative device, device delivery system and method of the present invention. A bullet shaped implant 350 provides for a relatively atraumatic insertion through the opening 201 into the pocket 207 formed in the submucosal layer 104b of the stomach wall. After the implant is inserted, the opening 201 may re-close due to the elastic nature of the mucosal wall 104a. Thus, acute closure of the opening 201 may not be required as it may heal on its own without further intervention. The device includes surface electrodes 351, 352 for providing electrical stimulating pulses to the muscle layer 104c of the stomach wall and a sensor 349. When inserted into the pocket 207, the electrodes are oriented facing the muscle layer 104c. The implant 350 also comprises a lumen 353 (FIG. 31E) through a portion of the implant 350 so that it may be guided into place over a guidewire 354. The implant 350a of FIG. 31F has a side hole 353a for receiving guidewire 354 and may alternatively be used in the procedure described with respect to FIGS. 31A-D.

A pushing instrument 357 is provided for pushing the implant 350 into place within the pocket 207. The pushing instrument 357 may be introduced through a channel 112 in the endoscope 110 through which the placement of the implant 350 is visualized. The distal end 358 of the pushing instrument 357 includes a magnetic hex head 359 and the implant 350 has a hex opening 355 for receiving the hex head 359. A magnetic coupling or temporary attachment is provided between the distal end 358 of the pushing instrument 357 and the implant 350. The pushing instrument 357 also has a guidewire lumen 360 for receiving the guidewire 354 therethrough.

Figure 31A:
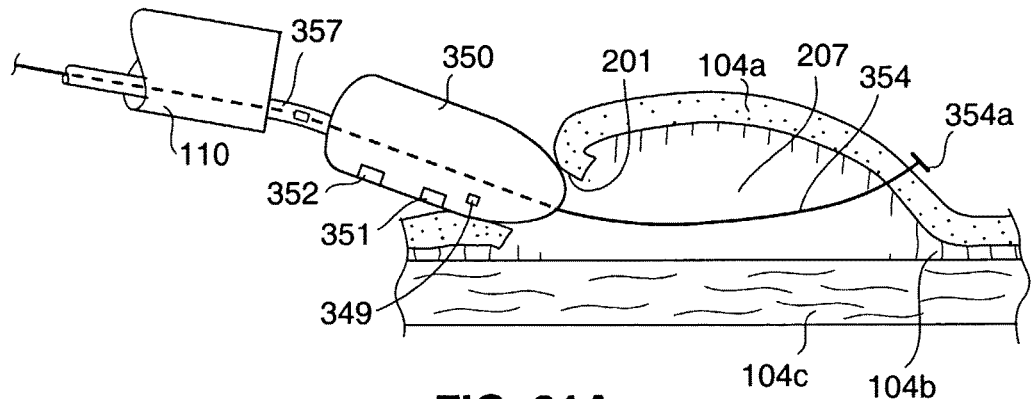
FIGS. 31A-31D illustrate side partial cross sectional views of a delivery device placing a stimulator of the present invention within the submucosa of the stomach wall.

In use, as illustrated in FIG. 31A a guidewire 354 with a T-shaped end 354a is placed through the submucosal pocket in a manner such as that described with reference to FIGS. 17A-G. The pushing instrument 357 is inserted through the channel 112 in the endoscope 110 and the hex head 359 is coupled to the hex opening 355 in the implant 350. When connected, the lumen 353 of the implant 350 and the guidewire lumen 360 of the pushing instrument 357 are coaxially aligned. The implant 350 and the pushing instrument are placed over the guidewire through lumen 353 and guidewire lumen 360 and the guidewire 354 guides the implant 350, pushing instrument 357 and endoscope 110 to the opening 201 in the stomach wall. A mark 356 is made on the proximal end of the implant 350 that indicates the rotational orientation of the implant and thus the rotational position of the electrodes 351, 352. The mark 356 can be seen through the endoscope 110 and is used to rotationally align the implant 350 so that the electrodes 351, 352, are facing the muscle layer 104c when the implant is in place.

Figure 31B:
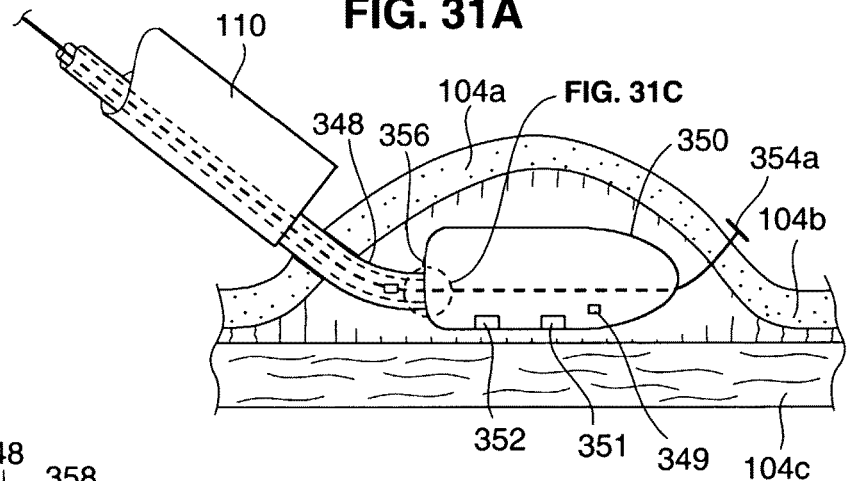
Figure 31C:
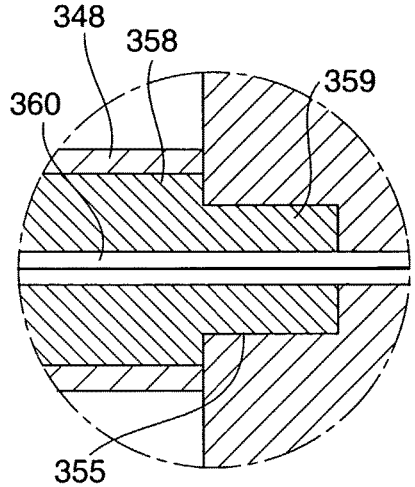
Figure 31D:
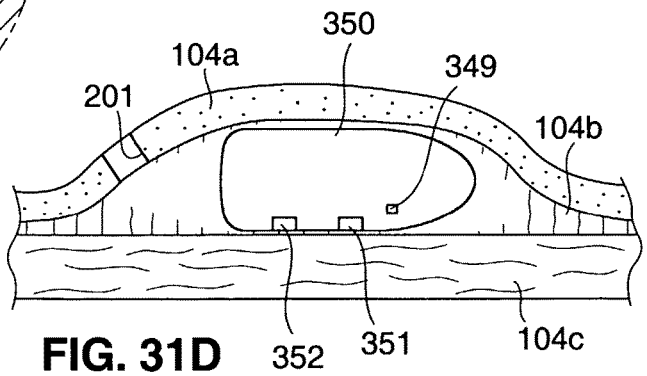
Figure 31E:
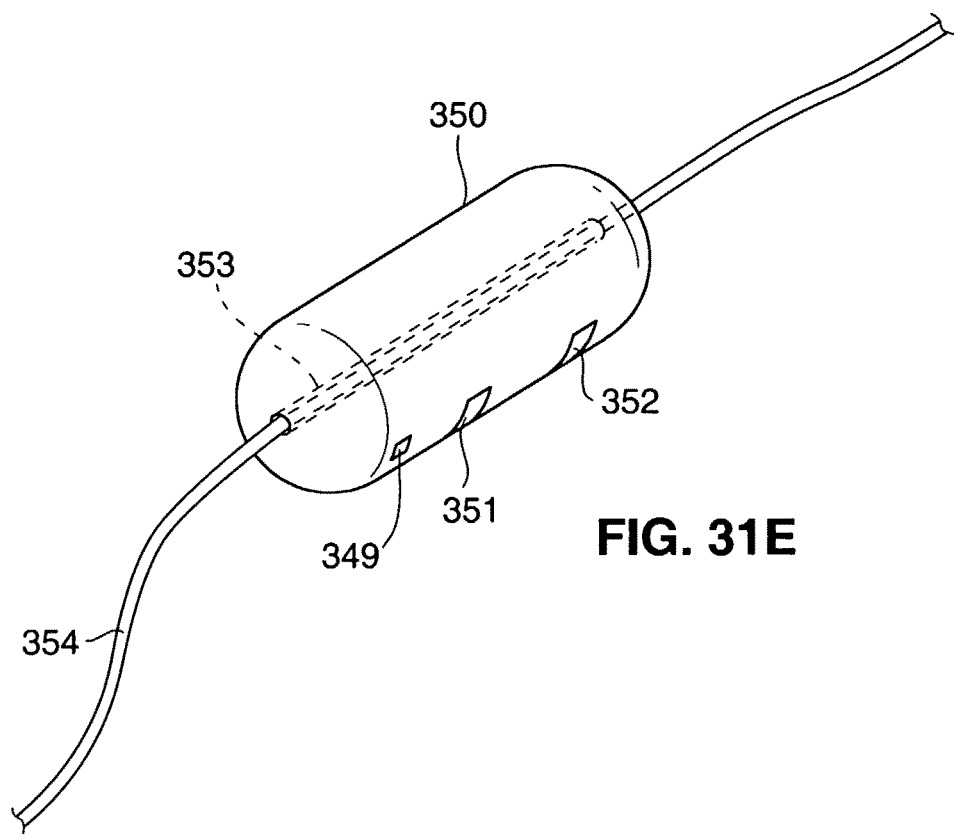
FIG. 31E is a perspective view of the implant of FIGS. 31A-D.
Figure 31F:
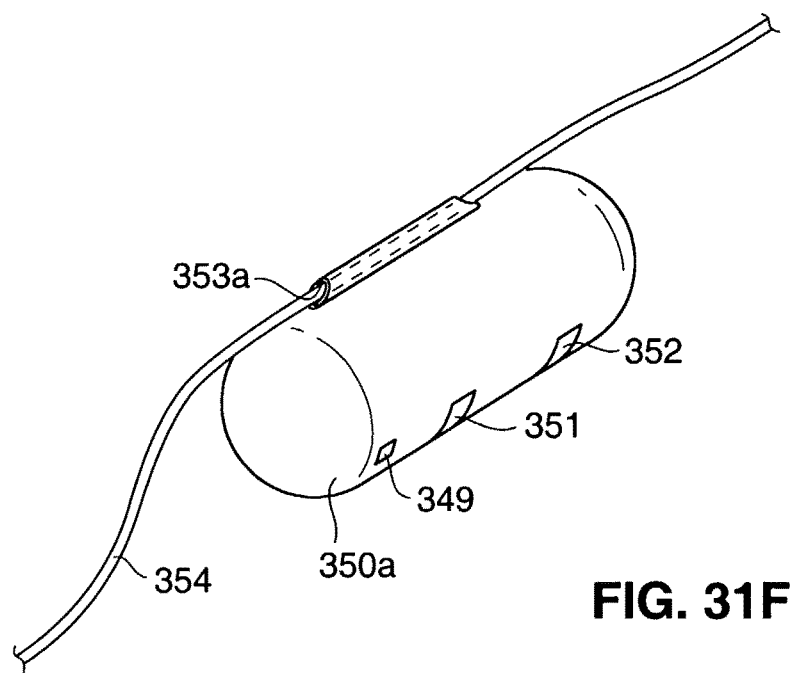
FIG. 31F is a perspective view of an alternative implant for use in the method described with respect to FIGS. 31A-D FIGS. 32A-D illustrate side cross sectional views of an incision closure device of the present invention in which the opening in the stomach wall for device placement is closed.

As illustrated in FIG. 31B, the implant 350 is placed within the pocket by distally advancing the pushing instrument 357 out of the channel 112. The hex connection formed of the hex head 359 and the hex opening 355 allows the pushing instrument 357 to be rotated to properly align the implant 350. After the device is properly placed, the pushing instrument 357 is disengaged by inserting a sheath 348 through the channel 112 in the endoscope 110 and over the pushing instrument 357. The sheath 348 engages the implant 350 while the instrument 357 is disengaged from the implant 350. The T-shaped end 354a of the guidewire 354 is cut so the guidewire 354 may be removed.

Once an implant is in place, it may be desirable to temporarily hold and prevent migration of the electrical stimulation device until some fibrous encapsulation develops. A resorbable bioadhesive may be used for such purpose. It may also be desirable to close the pocket at the incision site in the mucosa.

Wound Closure Devices

Figure 32A:
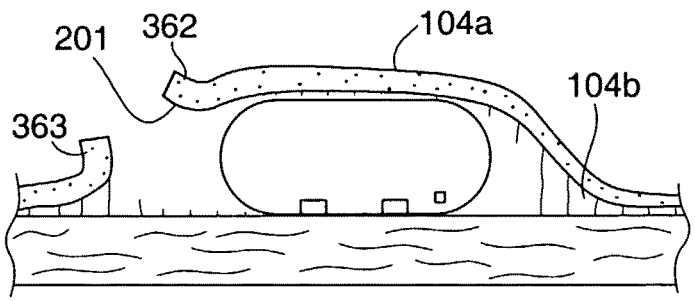

FIGS. 32A-D illustrate a device and method for closing the opening 201 in the stomach wall after the implant has been placed within the submucosal layer 104b. As illustrated in FIG. 32A mucosal flaps 362, 363 are separated and form opening 201 to be closed.

Figure 32B:
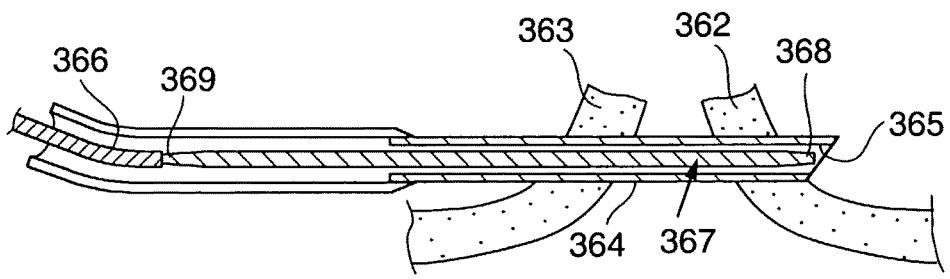
Figure 32C:
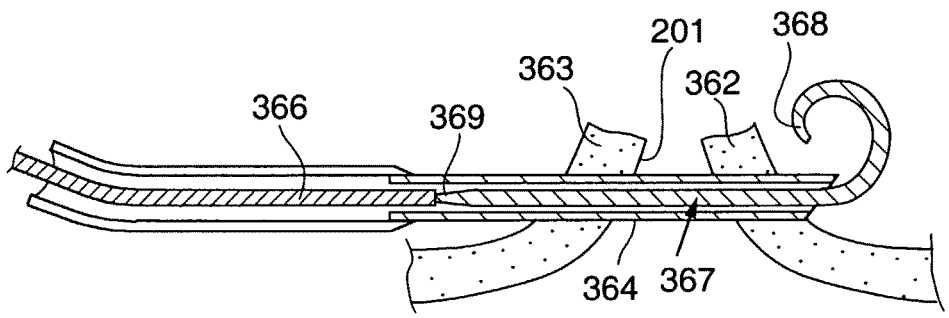
Figure 32D:
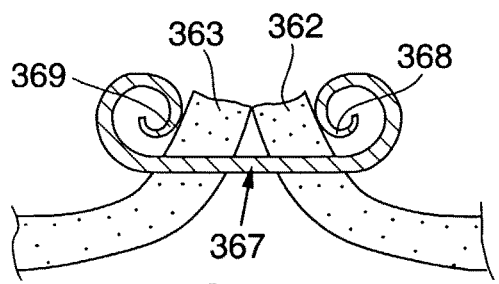

A wound closure instrument 361 comprising a hollow needle 364 at its distal end. The instrument 361 contains a closure device 367 in a lumen 365 extending though the instrument 361 and opening at the distal end of the needle 364. The instrument 361 further comprises a push rod 366 arranged to advance the closure device 367 distally out of the hollow needle 364. The closure device 367 is made of a super elastic material such as a Nickel Titanium alloy. The closure device 367 comprises ends 368, 369 that tend to curl towards each other. In use, as illustrated in FIG. 32B, the hollow needle 364 pierces the flaps 362, 363. The closure device 367 is loaded into the lumen 365 in the hollow needle 364 in a straight position. As illustrated in FIG. 32C, the push rod 366 advances the end 368 of the closure device 367 out of the hollow needle 364 so that the end 368 curls to engage the flap 362. As illustrated in FIG. 32D, the hollow needle 364 is retracted and the end 369 curls in to engage the flap 363. The curled ends 368, 369 of the closure device draw the flaps 362, 363 together to close the opening 201.

Figure 33A:
Figure 33B:
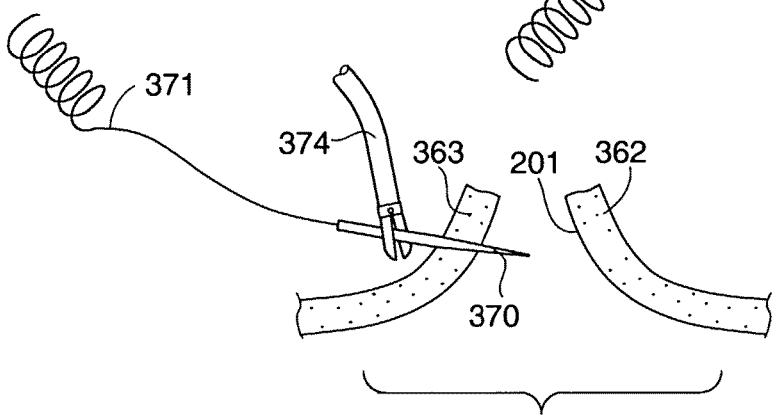
Figure 33C:
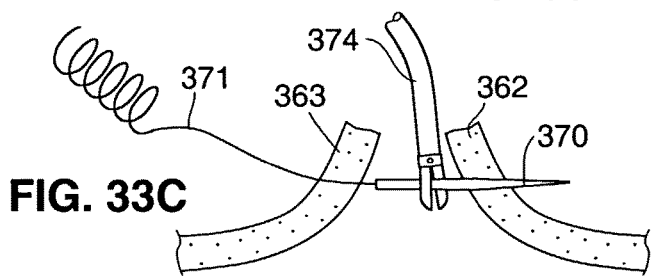
Figure 33D:
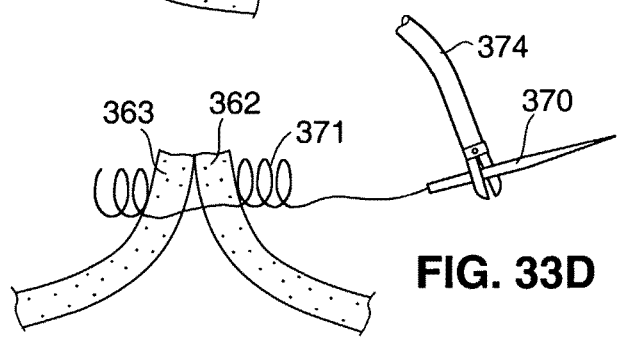
Figure 33E:
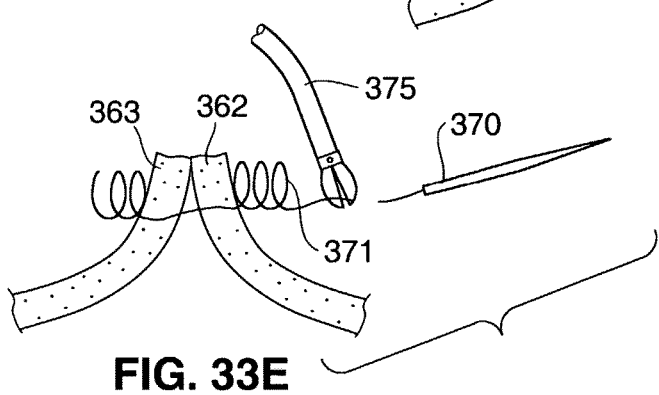

FIGS. 33A-E illustrate an alternative device and method for closing the opening 201 in the stomach wall after the implant has been placed within the submucosal layer 104b. As illustrated in previous FIG. 32A, mucosal flaps 362, 363 are separated and form opening 201 to be closed. FIG. 33A illustrates a needle 370 with a flexible elastic wire 371 attached to the needle 370. The elastic wire 371 is made of a superelastic material, such as a Nickel-Titanium alloy, and tends towards a coiled configuration. As illustrated in FIGS. 33B-C an endoscopic grasping tool 374 grasps the needle 370 and pulls it through flaps 362, 363. As illustrated in FIG. 33D, the wire 371 tends toward its coiled configuration and thus draws the flaps 362, 363 together. As illustrated in FIG. 33E, after the wire 371 is drawn through the flaps 362, 362, an endoscopic cutting instrument 375 cuts the wire from the needle 370, leaving the wire 371 in place closing the flaps 362, 363.

FIGS. 34A-34C illustrate a needle 376 and wire 377 used to join flaps 362,363. The wire 377 is attached to or threaded onto needle 376. The wire 377 is longer that the wire 371 described with respect to FIGS. 33A-E so that it can be sewn through the flaps 362, 363 at multiple points. The wire 377 is sewn through multiple points so that coiled portions 378 of the wire are left at each entry and exit point.

FIG. 35 illustrates a bipolar electrosurgical welding device 380 in use in closing the wound by electrosurgically welding flaps 384, 385 together. The welding device 380 includes articulating distal members 381a and 381b each with interfacing bipolar electrodes 382a and 382b respectively on their tips. The articulating members 381a, 381b are used to grasp and hold the flaps 384, 385 and to provide electrical contact with the electrodes 382a, 382b while electrosurgical energy is delivered through the flaps 384, 385 between the electrodes 382a, 382b. The electrosurgical energy causes the tissue of the flaps to heat and form bonds between the tissue of the flaps 384, 385.

Alternative means for closing the wound or opening 201 may be used, such as, for example, an clip applier, suturing device or a bonding agent such as cyanoacrylate. FIG. 37 illustrates the use of a bioadhesive or filler 391 to fill in the opening 201 and thereby join the flaps 362, 362.

The stimulator or functional device of the present invention may be configured to be implanted in the submucosa of a stomach wall. In addition to the size and rounded shape of the implant, relatively compliant, flexible or softer biocompatible materials may be used. Such materials may be selected so that the hardness of the material is similar to the hardness of the muscle layer of the stomach wall.

The stimulator or functional device of the present invention may be configured to communicate to an external recorder or controller by way of telemetry. They may be battery powered or powered by inductive coupling. A plurality of functional devices may be implanted the stomach wall. The functional devices may be programmed to respond to information or signals delivered by other functional devices whether the signals are delivered from one device to another through conductors, by telemetry or whether the signals are delivered, e.g. through the stomach wall or medium within the stomach.

The device may be implanted using on or more of the steps described herein. The implant may be implanted in an open or laparoscopic procedure as well as endoscopically through the esophagus. The implant is placed by forming an opening in the stomach wall to access the submucosa and the device is then implanted in the submucosa. One or more of the steps of forming a bleb, preparing a pocket and closing the opening may be used in the procedure in any of these types of procedures whether the submucosal layer is accessed form the outside of the stomach or the inside of the stomach.

Various means including but not limited to those specifically described are contemplated for preventing loss of electrical contact of the electrodes with the muscle layer, including various expanding members, suturing and anchoring and implantation means that anchor the electrodes in contact with the muscle layer and device configurations. Portions of the device may remain outside of the stomach wall, particularly for easy access to remove and replace portions of the device such as battery units.

While the invention has been described with reference to certain embodiments, it will be understood that variations and modifications may be made within the scope of the following claims. Such modifications may include substituting elements or components, which perform substantially the same function in substantially the same way to achieve substantially the same result that the invention can be practiced with modification within the scope of the following claims.

What is claimed is:

1. A device for treating obesity of a patient having a stomach and a small intestine, the device comprising:
    an implantable system including an implantable sensor adapted to be implanted in engagement with a tissue of the stomach of the patient so as to sense parameters therefrom and an implantable stimulator configured to be implanted substantially between a mucosal layer and a muscle layer and configured to apply electrical stimulation to the muscle layer of the stomach and delay passage of food or liquid from the stomach to the small intestine so as to create a feeling of satiety for the patient; and
    circuitry coupled to the sensor and the stimulator, the circuitry comprising a processor configured for determining when material has been ingested into the stomach of the patient in response to the sensed parameters, the circuitry comprising implanted circuitry adapted for use within the patient, external circuitry adapted for use outside the patient, and telemetry adapted for wirelessly transmitting signals between the implanted circuitry and the external circuitry during use;
    the implanted circuitry comprising an implanted event memory adapted for storing data in response to the parameters sensed by the sensor;
    the external circuitry comprising an external event memory and an output coupled to the external event memory, the telemetry intermittently sending the signals in response to the data from the implanted event memory for storage of associated data in the external event memory; and
    the output indicating to the patient or a treating practitioner the determination by the circuitry that material has been ingested so as to delay passage of food or liquid from the stomach to the small intestine and wherein the processor of the circuitry controls a therapy to delay movement of food or liquid through the stomach and into the small intestine for the patient by altering electrical stimulation in response to the signals so that effectiveness of the therapy is enhanced.

2. The device of claim 1, wherein the output comprises at least one member selected from the group consisting of:
a display and/or speaker.

3. The device of claim 1, wherein the sensor comprises an electrode and the parameters comprise electrical activity of a stomach wall, wherein the circuitry determines contractions of the stomach wall, and wherein the external circuitry comprises a port coupleable to a computer so as to communicate signals generated in response to the contractions, the port providing bi-directional communication between the computer and the external circuitry.

4. The device of claim 1, wherein the electrical stimulation entrains a slow wave signal of a smooth muscle of the stomach so as to alter contractions.

5. The device of claim 1, wherein the circuitry comprises a memory configured to facilitate observing patterns of the patient over time in response to the data.

6. The device of claim 1, wherein the sensor comprises a temperature sensor, and wherein the parameters comprise temperatures responsive to the ingestion by the patient so that the circuitry is configured to provide the determination in response to the temperatures.

7. The device of claim 1, the device comprising an implantable functional device for providing a diagnostic function to a stomach of the patient, the patient being an obese patient, wherein the implantable circuitry is included in:
    at least one functional component configured for performing the diagnostic function so as to diagnose obesity by transmitting the signals, the signals comprising obesity diagnostic signals;
    and further comprising a power source coupled with the at least one functional component so as to provide power to the at least one functional component; and
    wherein the sensor is coupled with the at least one functional component, and
    wherein the power source is implanted substantially between the mucosal layer and the muscle layer of the stomach in use.

8. The device of claim 1, wherein the muscle layer is a smooth muscle layer.

9. A device for treating obesity of a patient having a stomach and a small intestine, the device comprising:
    an implantable system including an implantable sensor adapted to be implanted in engagement with a tissue of the stomach of the patient so as to sense parameters therefrom and an implantable stimulator configured to be implanted substantially in the submucosal layer and configured to apply electrical stimulation to the muscle layer of the stomach and delay passage of food or liquid from the stomach to the small intestine so as to create a feeling of satiety for the patient; and
    circuitry coupled to the sensor and the stimulator, the circuitry comprising a processor configured for determining when material has been ingested into the stomach of the patient in response to the sensed parameters, the circuitry comprising implanted circuitry adapted for use within the patient, external circuitry adapted for use outside the patient, and telemetry adapted for wirelessly transmitting signals between the implanted circuitry and the external circuitry during use;
    the implanted circuitry comprising an implanted event memory adapted for storing data in response to the parameters sensed by the sensor;
    the external circuitry comprising an external event memory and an output coupled to the external event memory, the telemetry intermittently sending the signals in response to the data from the implanted event memory for storage of associated data in the external event memory;
    wherein the sensor comprises an electrode and the parameters comprise electrical activity of a stomach wall, wherein the circuitry determines contractions of the stomach wall, and wherein the external circuitry comprises a port coupleable to a computer so as to communicate signals generated in response to the contractions, the port providing bi-directional communication between the computer and the external circuitry; and
the output indicating to the patient or a treating practitioner the determination by the circuitry that material has been ingested so as to delay passage of food or liquid from the stomach to the small intestine and wherein the processor of the circuitry controls a therapy to delay movement of food or liquid through the stomach and into the small intestine for the patient by altering electrical stimulation in response to the signals so that effectiveness of the therapy is enhanced.

* * * * *